(12) United States Patent
Ku et al.

(10) Patent No.: US 10,201,425 B2
(45) Date of Patent: Feb. 12, 2019

(54) IMPLANTABLE OPEN VEIN VALVE

(71) Applicant: Georgia Tech Research Corporation, Atlanta, GA (US)

(72) Inventors: David N. Ku, Decatur, GA (US); Daniel Tanner, Flagstaff, AZ (US)

(73) Assignee: Georgia Tech Research Corporation

( * ) Notice: Subject to any disclaimer, the term of this patent is extended or adjusted under 35 U.S.C. 154(b) by 101 days.

(21) Appl. No.: 15/058,617

(22) Filed: Mar. 2, 2016

(65) Prior Publication Data

US 2016/0256277 A1 Sep. 8, 2016

Related U.S. Application Data

(60) Provisional application No. 62/127,100, filed on Mar. 2, 2015.

(51) Int. Cl.
*A61F 2/24* (2006.01)

(52) U.S. Cl.
CPC .......... *A61F 2/2475* (2013.01); *A61F 2/2415* (2013.01); *A61F 2230/0008* (2013.01); *A61F 2240/00* (2013.01); *A61F 2240/002* (2013.01)

(58) Field of Classification Search
CPC ........ A61F 2/24; A61F 2/2475; A61F 2/2415; A61F 2/2463; A61F 2/2412; A61F 2/2418
USPC .............................. 623/1.24, 1.26, 2.14, 2.18
See application file for complete search history.

(56) References Cited

U.S. PATENT DOCUMENTS

| | | | | |
|---|---|---|---|---|
| 15,192 | A * | 6/1856 | Peale | F16K 15/147 |
| | | | | 137/844 |
| 4,904,254 | A * | 2/1990 | Lane | A61B 17/12009 |
| | | | | 606/153 |
| 5,314,473 | A * | 5/1994 | Godin | A61F 2/04 |
| | | | | 623/23.68 |
| 5,500,014 | A * | 3/1996 | Quijano | A61B 17/12 |
| | | | | 623/1.24 |
| 5,609,626 | A * | 3/1997 | Quijano | A61B 17/11 |
| | | | | 606/153 |
| 5,954,766 | A * | 9/1999 | Zadno-Azizi | A61F 2/0009 |
| | | | | 623/1.24 |
| 5,981,826 | A | 11/1999 | Ku et al. | |
| 6,126,686 | A * | 10/2000 | Badylak | A61L 27/3691 |
| | | | | 623/1.24 |
| 6,165,215 | A * | 12/2000 | Rottenberg | A61F 2/2412 |
| | | | | 623/2.12 |
| 6,231,605 | B1 | 5/2001 | Ku | |

(Continued)

OTHER PUBLICATIONS

Alimi, et al. Venous pump of the calf: a study of venous and muscular pressures. J Vasc Surg. Nov. 1994;20(5):728-35.

(Continued)

*Primary Examiner* — Alvin Stewart
(74) *Attorney, Agent, or Firm* — Wilson Sonsini Goodrich & Rosati

(57) ABSTRACT

The invention provides prosthetic venous valves, and method of use thereof, for the effective treatment of individuals with venous reflux in chronic venous insufficiency (CVI). The development of such prosthetic venous valves in the areas of valve design, design specifications, verification and/or validation testing, computational analysis, valve placement and clinician guidance and procedure are provided. Manufacturing the prosthetic venous valves of the invention is also provided.

13 Claims, 21 Drawing Sheets

(56) References Cited

U.S. PATENT DOCUMENTS

| | | | | |
|---|---|---|---|---|
| 6,264,700 B1* | 7/2001 | Kilcoyne | ............ | A61F 2/04 623/23.68 |
| 6,669,724 B2* | 12/2003 | Park | ............ | A61F 2/2418 623/1.24 |
| 6,764,518 B2* | 7/2004 | Godin | ............ | A61F 2/04 623/23.68 |
| 7,316,716 B2* | 1/2008 | Egan | ............ | A61F 2/04 623/23.65 |
| 7,771,467 B2* | 8/2010 | Svensson | ............ | A61F 2/07 623/1.24 |
| 7,837,645 B2* | 11/2010 | Bessler | ............ | A61F 2/07 604/8 |
| 8,029,557 B2* | 10/2011 | Sobrino-Serrano | ....... | A61F 2/04 623/1.24 |
| 8,038,720 B2* | 10/2011 | Wallace | ............ | A61B 17/12036 604/8 |
| 8,251,067 B2* | 8/2012 | Hendricksen | .... | A61B 17/12022 128/200.26 |
| 8,337,545 B2* | 12/2012 | Osborne | ............ | A61F 2/2412 623/1.24 |
| 8,474,460 B2* | 7/2013 | Barrett | ............ | A61B 17/12022 128/207.16 |
| 8,500,821 B2* | 8/2013 | Sobrino-Serrano | ....... | A61F 2/04 604/9 |
| 8,556,960 B2* | 10/2013 | Agnew | ............ | A61F 2/2412 623/1.24 |
| 8,673,020 B2* | 3/2014 | Sobrino-Serrano | ....... | A61F 2/04 604/9 |
| 8,876,800 B2* | 11/2014 | Behan | ............ | A61F 2/0009 604/540 |
| 8,906,083 B2* | 12/2014 | Obermiller | ............ | A61F 2/2418 623/1.24 |
| 9,056,006 B2* | 6/2015 | Edelman | ............ | A61F 2/2412 |
| 9,427,303 B2* | 8/2016 | Liddy | ............ | A61F 2/06 |
| 9,474,638 B2* | 10/2016 | Robinson | ............ | A61F 2/04 |
| 9,498,314 B2* | 11/2016 | Behan | ............ | A61F 2/0009 |
| 9,743,932 B2* | 8/2017 | Amplatz | ............ | A61B 17/12022 |
| 9,814,572 B2* | 11/2017 | Edelman | ............ | A61F 2/2412 |
| 2002/0177894 A1* | 11/2002 | Acosta | ............ | A61F 2/2412 623/1.24 |
| 2003/0009236 A1* | 1/2003 | Godin | ............ | A61F 2/04 623/23.68 |
| 2003/0060875 A1* | 3/2003 | Wittens | ............ | A61F 2/2418 623/1.23 |
| 2003/0069635 A1* | 4/2003 | Cartledge | ............ | A61F 2/2412 623/2.13 |
| 2004/0133267 A1* | 7/2004 | Lane | ............ | A61B 17/12013 623/1.24 |
| 2006/0041189 A1* | 2/2006 | Vancaillie | ............ | A61B 1/00137 600/154 |
| 2006/0111773 A1* | 5/2006 | Rittgers | ............ | A61F 2/2409 623/1.24 |
| 2007/0027528 A1* | 2/2007 | Agnew | ............ | A61F 2/2412 623/1.24 |
| 2007/0027549 A1* | 2/2007 | Godin | ............ | A61F 2/04 623/23.68 |
| 2008/0091261 A1* | 4/2008 | Long | ............ | A61F 2/2412 623/1.24 |
| 2008/0269879 A1* | 10/2008 | Sathe | ............ | A61F 2/2412 623/2.12 |
| 2012/0053676 A1* | 3/2012 | Ku | ............ | A61F 2/2412 623/1.26 |
| 2013/0289711 A1* | 10/2013 | Liddy | ............ | A61F 2/06 623/1.24 |
| 2014/0257461 A1* | 9/2014 | Robinson | ............ | A61F 2/04 623/1.15 |
| 2015/0119970 A1* | 4/2015 | Nakayama | ............ | A61F 2/07 623/1.13 |
| 2017/0196692 A1* | 7/2017 | Kirk | ............ | A61F 2/915 |

OTHER PUBLICATIONS

Anim, Kwaku. Design, development, testing, and evaluation of a prosthetic venous valve. Master of Science Thesis. The University of Akron. May 2010. 203 pages.
Araki, et al. The significance of calf muscle pump function in venous ulceration. J Vasc Surg. Dec. 1994;20(6):872-7.
Badimon, et al. Influence of arterial damage and wall shear rate on platelet deposition. Ex vivo study in a swine model. Arteriosclerosis. May-Jun. 1986;6(3):312-20.
Bark, et al. Correlation of thrombosis growth rate to pathological wall shear rate during platelet accumulation. Biotechnol Bioeng. Oct. 2012;109(10):2642-50.
Barstad, et al. A perfusion chamber developed to investigate thrombus formation and shear profiles in flowing native human blood at the apex of well-defined stenoses. Arterioscler Thromb. Dec. 1994;14(12):1984-91.
Barstad, et al. Collagen induced thrombus formation at the apex of eccentric stenoses—a time course study with non-anticoagulated human blood. Thromb Haemost. Apr. 1996;75(4):685-92.
Beddy, et al. Valsalva and gravitational variability of the internal jugular vein and common femoral vein: ultrasound assessment. Eur J Radiol. May 2006;58(2):307-9.
Beebe-Dimmer, et al. The epidemiology of chronic venous insufficiency and varicose veins. Ann Epidemiol. Mar. 2005;15(3):175-84.
Berger, et al. Flows in Stenotic Vessels. Annual Review of Fluid Mechanics, Jan. 2000, vol. 32, pp. 347-382.
Bia, et al. In vitro model to study arterial wall dynamics through pressure-diameter relationship analysis. Latin American Applied Research, vol. 35, No. 3, pp. 217-224, (2005).
Brookshier, et al. Effect of hematocrit on wall shear rate in oscillatory flow: do the elastic properties of blood play a role? Biorheology. 1991;28(6):569-87.
Cesarone, et al. Improvement of signs and symptoms of chronic venous insufficiency and microangiopathy with Pycnogenol: a prospective, controlled study. Phytomedicine. Sep. 2010;17(11):835-9.
Chiesa, et al. Demographic factors and their relationship with the presence of CVI signs in Italy: the 24-cities cohort study. Eur J Vasc Endovasc Surg. Dec. 2005;30(6):674-80.
Cho, et al. Effects of the non-Newtonian viscosity of blood on flows in a diseased arterial vessel. Part 1: Steady flows. Biorheology. 1991;28(3-4):241-62.
Christopoulos, et al. Air-plethysmography and the effect of elastic compression on venous hemodynamics of the leg. J Vasc Surg. Jan. 1987;5(1):148-59.
Cournane, et al. Assessment of the accuracy of an ultrasound elastography liver scanning system using a PVA-cryogel phantom with optimal acoustic and mechanical properties. Phys Med Biol. Oct. 7, 2010;55(19):5965-83.
Criqui, et al. Chronic venous disease in an ethnically diverse population: the San Diego Population Study. Am J Epidemiol. Sep. 1, 2003;158(5):448-56.
Dalsing, et al. An early experience with endovascular venous valve transplantation. Journal of Vascular Surgery. vol. 24, Issue 5, pp. 703-907 (Nov. 1996).
Danielsson, et al. Deep axial reflux, an important contributor to skin changes or ulcer in chronic venous disease. J Vasc Surg. Dec. 2003;38(6):1336-41.
De Borst, et al. A percutaneous approach to deep venous valve insufficiency with a new self-expanding venous frame valve. J Endovasc Ther. Apr. 2003;10(2):341-9.
DeLaria, et al. Hemodynamic evaluation of a bioprosthetic venous prosthesis. J Vasc Surg. Oct. 1993;18(4):577-84.
Delis, et al. Lower Limb Venous Haemodynamic Impairment on Dependency: Quantification and Implications for the "Economy Class" Position. Thromb Haemost 91(5), 941-950, (2004).
Depp, Michelle McRae. PVA cryogel optimization and diffusion studies. Master of Science Thesis. Georgia Institute of Technology. Sep. 1998. 118 pages.
Dickson, Brendan Craig. Venous Thrombosis: On the History of Virchow's Triad. University of Toronto Medical Journal. vol. 81, No. 3, May 2004, pp. 166-171.

(56) References Cited

OTHER PUBLICATIONS

Dijkstra, et al. Endovenous Valve Transfer for Chronic Venous Hypertension. PS134. Journal of Vascular Surgery. Jun. 2012, vol. 55, Issue 6, Supplement, p. 61S.
Dormandy, J.A. Clinical significance of blood viscosity. Ann R Coll Surg Engl. Oct. 1970;47(4):211-28.
Dotter, Charles T. Interventional radiology—review of an emerging field. Semin Roentgenol. Jan. 1981;16(1):7-12.
Duboeuf, et al. Investigation of PVA cryogel Young's modulus stability with time, controlled by a simple reliable technique. Med Phys. Feb. 2009;36(2):656-61.
Duboeuf, et al. Static mechanical assessment of elastic Young's modulus of tissue mimicking materials used for medical imaging. Conf Proc IEEE Eng Med Biol Soc. 2007;2007:3450-3.
Eberhardt, et al. Chronic venous insufficiency. Circulation. May 10, 2005;111(18):2398-409.
Eriksson, et al. Surgical Reconstruction of Incompetent Deep Vein Valves. Upsala J. Med. Sci. 93, pp. 139-143, (1988).
Farrell, Laura-Lee Amelia Catherine. Prosthetic vein valve: delivery and in vitro evaluation. Master of Science Thesis. May 2007. Georgia Institute of Technology. 107 pages.
Faul, et al. G*Power 3: a flexible statistical power analysis program for the social, behavioral, and biomedical sciences. Behav Res Methods. May 2007;39(2):175-91.
Faul, et al. Statistical power analyses using G*Power 3.1: tests for correlation and regression analyses. Behav Res Methods. Nov. 2009:41(4)1149-60.
Fowkes, et al. Lifestyle risk factors for lower limb venous reflux in the general population: Edinburgh Vein Study. Int J Epidemiol (2001) 30 (4): 846-852.
Fromageau, et al. Characterization of PVA cryogel for intravascular ultrasound elasticity imaging. IEEE Transactions on Ultrasonics, Ferroelectrics, and Frequency Control. vol. 50, Issue 10, Oct. 2003, pp. 1318-1324.
Fromageau, et al. Estimation of polyvinyl alcohol cryogel mechanical properties with four ultrasound elastography methods and comparison with gold standard testings. IEEE Trans Ultrason Ferroelectr Freq Control. Mar. 2007;54(3):498-509.
Fronek, et al. Common femoral vein dimensions and hemodynamics including Valsalva response as a function of sex, age, and ethnicity in a population study. J Vasc Surg. May 2001;33(5):1050-6.
Fukuoka, et al. Prospective evaluation of chronic venous insufficiency based on foot venous pressure measurements and air plethysmography findings. Journal of Vascular Surgery. vol. 38, Issue 4, Oct. 2003, pp. 804-811.
Gale, et al. Percutaneous venous valve bioprosthesis: initial observations. Vasc Endovascular Surg. May-Jun. 2004;38(3):221-4.
Gomez-Jorge, et al. Percutaneous deployment of a valved bovine jugular vein in the swine venous system: a potential treatment for venous insufficiency. J Vasc Interv Radiol. Jul.-Aug. 2000;11(7):931-6.
Gupta, et al. A combined effect of freeze-thaw cycles and polymer concentration on the structure and mechanical properties of transparent PVA gels. Biomed Mater. Feb. 2012;7(1):015006. doi: 10.1088/1748-6041/7/1/015006. Epub Jan. 27, 2012.
Haenen, et al. Venous duplex scanning of the leg: range, variability and reproducibility. Clin Sci (Lond). Mar. 1999;96(3):271-7.
Hellums, J. David. 1993 Whitaker Lecture: biorheology in thrombosis research. Ann Biomed Eng. Sep.-Oct. 1994;22(5):445-55.
Hertzberg, et al. Sonographic assessment of lower limb vein diameters: implications for the diagnosis and characterization of deep venous thrombosis. AJR Am J Roentgenol. May 1997;168(5):1253-7.
Hill, et al. Development of a prosthetic venous valve. J Biomed Mater Res. Sep. 1985; 19(7):827-32.
Hojensgard, et al. Static and dynamic pressures in superficial and deep veins of the lower extremity in man. Acta Physiol Scand. 1952;27(1):49-67.
Holloway, et al. Aging behavior of PVA hydrogels for soft tissue applications after in vitro swelling using osmotic pressure solutions. Acta Biomater. Feb. 2013;9(2):5013-21. doi: 10.1016/j.actbio.2012.09.018. Epub Sep. 25, 2012.
Iafrati, et al. Correlation of venous noninvasive tests with the Society for Vascular Surgery/International Society for Cardiovascular Surgery clinical classification of chronic venous insufficiency. Journal of Vascular Surgery. vol. 19, Issue 6, Jun. 1994, pp. 1001-1007.
Johnston, et al. Non-Newtonian blood flow in human right coronary arteries: steady state simulations. J Biomech. May 2004;37(5):709-20.
Kinsel, David. Design control requirements for medical device development. World J Pediatr Congenit Heart Surg. Jan. 1, 2012;3(1):77-81.
Kistner, et al. Surgery in acute and chronic venous disease. Surgery. Jan. 1979;85(1):31-43.
Ku, David N. New Soft Tissue Implants Using Organic Elastomers. BIOSTEC 2008: Biomedical Engineering Systems and Technologies, pp. 85-95.
Kucher, et al. Endovascular Delivery of Vein Segments with Valves versus Direct Anastomosis. Journal of Endovascular Therapy. Jun. 1, 2005. vol. 12 issue: 3, pp. 366-370.
Labropoulos, et al. Definition of venous reflux in lower-extremity veins. J Vasc Surg. Oct. 2003;38(4):793-8.
Labropoulos, et al. Venous hemodynamic abnormalities in patients with leg ulceration. Am J Surg. Jun. 1995;169(6):572-4.
Lattimer, et al. Saphenous pulsation on duplex may be a marker of severe chronic superficial venous insufficiency. J Vasc Surg. Nov. 2012;56(5):1338-43. doi: 10.1016/j.jvs.2012.04.048. Epub Jul. 12, 2012.
Laurikka, et al. Risk indicators for varicose veins in forty- to sixty-year-olds in the Tampere varicose vein study. World J Surg. Jun. 2002;26(6):648-51. Epub Mar. 1, 2002.
Lee, et al. In vitro testing of venous valves. ASAIO Trans. Jul.-Sep. 1991;37(3):M266-8.
Lee, et al. Lifestyle factors and the risk of varicose veins: Edinburgh Vein Study. J Clin Epidemiol. Feb. 2003;56(2):171-9.
Liu, et al. Fabrication of tissue engineered vein containing valve scaffolds. English-language Abstract. Zhonghua Yi Xue Za Zhi. Apr. 17, 2012;92(15):1054-7.
Lu, et al. The ovine jugular vein as a model for interventional radiology procedures. Radiology and Oncology. vol. 42, Issue 2 (Jun. 2008).
Lurie, et al. Mechanism of venous valve closure and role of the valve in circulation: a new concept. J Vasc Surg. Nov. 2003;38(5):955-61.
Marascalco, et al. Development of standard tests to examine viscoelastic properties of blood of experimental animals for pediatric mechanical support device evaluation. ASAIO J. Sep.-Oct. 2006;52(5):567-74.
Markou, et al. The role of high wall shear rate on thrombus formation in stenoses. ASME-Publications-BED. 1993;26:555.
McCaughan, et al. In vitro observations of greater saphenous vein valves during pulsatile and nonpulsatile flow and following lysis. J Vasc Surg. Mar. 1984;1(2):356-61.
Meissner, et al. The hemodynamics and diagnosis of venous disease. J Vasc Surg. Dec. 2007;46 Suppl S:4S-24S. doi: 10.1016/j.jvs.2007.09.043.
Mühlberger, et al. Venous valves and major superficial tributary veins near the saphenofemoral junction. J Vasc Surg. Jun. 2009;49(6):1562-9. doi: 10.1016/j.jvs.2009.02.241.
Midha, Prem Anand. Long-term patency of a polymer vein valve. Master of Science Thesis. Presented Aug. 2009. Georgia Institute of Technology. 127 pages.
Miyake, et al. New small-caliber antithrombotic vascular prosthesis: experimental study. Microsurgery. 1984;5(3):144-50.
Moriyama, et al. Evaluation of prosthetic venous valves, fabricated by electrospinning, for percutaneous treatment of chronic venous insufficiency. J Artif Organs. Dec. 2011;14(4):294-300. doi: 10.1007/s10047-011-0588-2. Epub Jul. 26, 2011.

(56) References Cited

OTHER PUBLICATIONS

Nash, Thomas. Long term results of vein valve transplants placed in the popliteal vein for intractable post-phlebitic venous ulcers and pre-ulcer skin changes. J Cardiovasc Surg (Torino). Nov.-Dec. 1988;29(6):712-6.
Neglén, et al. Balloon dilation and stenting of chronic iliac vein obstruction: technical aspects and early clinical outcome. J Endovasc Ther. Apr. 2000;7(2):79-91.
Neglén, et al. Detection of outflow obstruction in chronic venous insufficiency. J Vasc Surg. Mar. 1993;17(3):583-9.
Neglén, et al. Hemodynamic and clinical impact of ultrasound-derived venous reflux parameters. J Vasc Surg. Aug. 2004;40(2):303-10.
Nicolaides, et al. Investigation of chronic venous insufficiency: A consensus statement (France, Mar. 5-9, 1997). Circulation. Nov. 14, 2000;102(20):E126-63.
Nuttelman, et al. Attachment of fibronectin to poly(vinyl alcohol) hydrogels promotes NIH3T3 cell adhesion, proliferation, and migration. J Biomed Mater Res. Nov. 2001;57(2):217-23.
Ofenloch, et al. Endoscopic venous valve transplantation with a valve-stent device. Ann Vasc Surg. Jan. 1997;11(1):62-7.
Onuki, et al. A review of the biocompatibility of implantable devices: current challenges to overcome foreign body response. J Diabetes Sci Technol. Nov. 2008;2(6):1003-15.
Para, Andrea N. Preventing rapid platelet accumulation under very high shear stress. Ph.D. Thesis. Georgia Institute of Technology. Aug. 2012. 141 pages.
Para, et al. Rapid Platelet Accumulation Leading to Thrombotic Occlusion. Ann Biomed Eng 39 (7), 1961-1971. Mar. 22, 2011.
Pavcnik, Dusan. Update on Venous Valve Replacement: Long-Term Clinical Results. XXIV.6. Vascular. Nov. 2006, vol. 14, S1, p. S106.
Pavcnik, et al. Percutaneous autologous venous valve transplantation: short-term feasibility study in an ovine model. J Vasc Surg. Aug. 2007;46(2):338-45.
Pavcnik, et al. Percutaneous bioprosthetic venous valve: a long-term study in sheep. J Vasc Surg. Mar. 2002;35(3):598-602.
Pavcnik, et al. Percutaneous management of chronic deep venous reflux: review of experimental work and early clinical experience with bioprosthetic valve. Vasc Med. Feb. 2008;13(1):75-84.
Pavcnik, et al. Percutaneous prosthetic venous valves: current state and possible applications. Tech Vasc Interv Radiol. Sep. 2003;6(3):137-42.
Pavcnik, et al. Percutaneous therapy for deep vein reflux. Seminars in Interventional Radiology. Sep. 2005;22(3):225-232.
Pavcnik, et al. Second-generation percutaneous bioprosthetic valve: a short-term study in sheep. J Vasc Surg. Dec. 2004;40(6):1223-7.
Pavcnik, et al. Significance of spatial orientation of percutaneously placed bioprosthetic venous valves in an ovine model. J Vasc Interv Radiol. Nov. 2005;16(11):1511-6.
Phillips, et al. A study of the impact of leg ulcers on quality of life: financial, social, and psychologic implications. J Am Acad Dermatol. Jul. 1994;31(1):49-53.
Rachel, et al. Percutaneous endovascular abdominal aortic aneurysm repair. Ann Vasc Surg. Jan. 2002;16(1):43-9. Epub Jan. 16, 2002.
Raja, Vidya. Computational Fluid Dynamics Analysis of a Prototypic, Prosthetic Venous Valve. Master of Science Thesis, University of Akron. Aug. 2007. 204 pages.
Raju, et al. Chronic Venous Insufficiency and Varicose Veins. N Engl J Med 2009; 360:2319-2327.
Raju, et al. Valve reconstruction procedures for nonobstructive venous insufficiency: Rationale, techniques, and results in 107 procedures with two- to eight-year follow-up. Journal of Vascular Surgery. Feb. 1988. vol. 7, Issue 2, pp. 301-310.
Rippey, et al. Abdominal compression effectively increases the size of the common femoral vein, as measured by ultrasonography. Ann Emerg Med. Oct. 2008;52(4):446-52.
Rittgers, et al. Physiologically-based testing system for the mechanical characterization of prosthetic vein valves. Biomed Eng Online. 2007; 6: 29. Published online Jul. 13, 2007. doi: 10.1186/1475-925X-6-29.
Sathe, et al. Flexible Prosthetic Vein Valve. Journal of Medical Devices. Copyright 2007 by ASME. Jun. 2007, vol. 1, pp. 105-112.
Sathe, Rahul Dilip. Design and Development of a Novel Implantable Prosthetic Vein Valve. Master of Science Thesis. Georgia Institute of Technology. May 2006. 193 pages.
Savage, et al. Initiation of platelet adhesion by arrest onto fibrinogen or translocation on von Willebrand factor. Cell. Jan. 26, 1996;84(2):289-97.
Sollier, et al. Rapid prototyping polymers for microfluidic devices and high pressure injections. Lab Chip. Nov. 21, 2011;11(22):3752-65.
Sottiurai, Vikrom. Current surgical approaches to venous hypertension and valvular reflux. International Journal of Angiology. Dec. 1996, vol. 5, Issue 1, pp. 49-54.
Sottiurai, V.S. Comparison of surgical modalities in the treatment of recurrent venous ulcer. Int Angiol. Oct.-Dec. 1990;9(4):231-5.
Stammen, et al. Mechanical properties of a novel PVA hydrogel in shear and unconfined compression. Biomaterials. Apr. 2001;22(8):799-806.
Stick, et al. Venous pressure in the saphenous vein near the ankle during changes in posture and exercise at different ambient temperatures. Eur J Appl Physiol Occup Physiol. 1993;66(5):434-8.
Taheri, et al. Experimental prosthetic vein valve. Am J Surg. Aug. 1988;156(2):111-4.
Taheri, et al. Experimental prosthetic vein valve. Long-term results. Angiology. Apr. 1995;46(4):299-303.
Taheri, et al. Indications and results of vein valve transplant. J Cardiovasc Surg. 1986;27:163-168.
Teebken, et al. Preclinical development of tissue-engineered vein valves and venous substitutes using re-endothelialised human vein matrix. Eur J Vasc Endovasc Surg. Jan. 2009;37(1):92-102.
Teebken, et al. Tissue-engineered bioprosthetic venous valve: a long-term study in sheep. Eur J Vasc Endovasc Surg. Apr. 2003;25(4):305-12.
Tripathi, et al. Five-Year Experience of Valvular Reconstructions for Nonhealing Leg Ulceration due to Deep Venous Reflux: Lessons Learned. Perspectives in Vascular Surgery and Endovascular Therapy. vol. 15, Issue 2, 2002. pp. 87-100.
Van Bemmelen, et al. Quantitative segmental evaluation of venous valvular reflux with duplex ultrasound scanning. J Vasc Surg. Oct. 1989;10(4):425-31.
Van Bemmelen, et al. The mechanism of venous valve closure. Its relationship to the velocity of reverse flow. Arch Surg. May 1990;125(5):617-9.
Vasdekis, et al. Quantification of venous reflux by means of duplex scanning. J Vasc Surg. Dec. 1989;10(6):670-7.
Vasquez, et al. Revision of the venous clinical severity score: venous outcomes consensus statement: special communication of the American Venous Forum Ad Hoc Outcomes Working Group. J Vasc Surg. Nov. 2010;52(5):1387-96.
Vasquez, et al. The utility of the Venous Clinical Severity Score in 682 limbs treated by radiofrequency saphenous vein ablation. J Vasc Surg. May 2007;45(5):1008-1014.
Victor, et al. Reflex stimulation of sympathetic outflow during rhythmic exercise in humans. Am J Physiol. Dec. 1989;257(6 Pt 2):H2017-24.
Weaver, et al. Biomaterial testing for covered stent membranes: evaluating thrombosis and restenosis potential. J Biomed Mater Res B Appl Biomater. Jan. 2012;100(1):103-10.
Weaver, et al. Mechanical Evaluation of Polyvinyl Alcohol Cryogels for Covered Stents. Copyright 2010 by ASME. J. Med. Devices 4(3), 031002 (Aug. 31, 2010).
Weaver, Jason David. Development of a polyvinyl alcohol cryogel covered stent. Ph.D. Dissertation. Aug. 2010. Georgia Institute of Technology. 169 pages.
Wilcoxon, Frank. Individual Comparisons by Ranking Methods. International Biometric Society. Biometrics Bulletin. vol. 1, No. 6 (Dec. 1945), pp. 80-83.

(56) References Cited

OTHER PUBLICATIONS

Williams, Stephen. Mechanical testing of a new biomaterial for potential use as a vascular graft and articular cartilage substitute. Master of Science Thesis. Sep. 1998. Georgia Institute of Technology. 128 pages.

Wilson, et al. Repair and replacement of deep vein valves in the treatment of venous insufficiency. Br J Surg. Apr. 1991;78(4):388-94.

Windberger, et al. Whole blood viscosity, plasma viscosity and erythrocyte aggregation in nine mammalian species: reference values and comparison of data. Exp Physiol. May 2003;88(3):431-40.

Xie, et al. Controlled mechanical and swelling properties of poly-(vinyl alcohol)/sodium alginate blend hydrogels prepared by freeze-thaw followed by $Ca^{2+}$ crosslinking. Journal of Applied Polymer Science. vol. 124. Issue 1. Apr. 5, 2012. First published online: Oct. 10, 2011. pp. 823-831.

Zydney, et al. Augmented solute transport in the shear flow of a concentrated suspension. Physicochemical hydrodynamics, vol. 10, No. 1, pp. 77-96, 1988.

\* cited by examiner

IMPLANTABLE OPEN VEIN VALVE

CROSS-REFERENCE TO RELATED APPLICATIONS

This application claims priority to, and the benefit under 35 U.S.C. § 119(e), of U.S. Provisional Patent Application No. 62/127,100, filed Mar. 2, 2015, the entire contents and substance of which are hereby incorporated by reference as if fully set forth below.

FIELD OF THE INVENTION

The invention relates to apparatus, systems, and methods for use in limbs. More particularly to a valve apparatus, systems, and methods for use in the treatment for chronic venous insufficiency (CVI).

BACKGROUND OF THE INVENTION

Chronic Venous Insufficiency (CVI) is characterized by chronic venous hypertension from blood pooling in the lower limbs [1, 2]. In healthy veins, muscle contractions efficiently pump blood back to the heart while venous valves close to prevent reflux [3]. Venous hypertension and CVI can develop in the presence of venous reflux, venous obstruction, and calf muscle pump dysfunction [1]. The resulting symptoms include leg pain, varicose veins, fatigue, venous edema, skin pigmentation, inflammation, induration, and ulceration [4]. The risk of developing CVI increases with age, body mass index, height, family history of CVI, European ancestry, Hispanic ethnicity, pregnancy, prolonged standing, straining during bowel movements, being female, and residing in an industrialized country [5-10].

Treatments for CVI include exercise, compression, medication, vein disabling, venous stenting, surgical correction, and valve replacement. Thus far these treatments have demonstrated varying levels of efficacy in reducing the symptom severity. In practice the most conservative treatment is applied first, typically compression stockings, with more invasive procedures being pursued when symptoms do not significantly improve [30]. The appropriateness of each treatment is further determined by the functionality of the calf muscle pump as well as the presence and location of venous reflux and obstruction [31]. The time spent by an individual caring for an ulcer has been found to be highly correlated with feelings of resentment and anger [11]. Therefore, in addition to symptom relief, the time required of an individual for a given treatment must be considered when evaluating its efficacy.

A prosthetic venous valve has the potential to correct reflux in the deep, superficial, and perforating venous systems. While alternative minimally invasive treatments have the potential to stop reflux in the superficial and perforating venous systems, currently only invasive treatments exist for the correction of deep venous reflux.

Dotter was the first to suggest the concept of a transcatheter venous valve [35]. Such a valve would meet the need for a minimally invasive treatment for deep venous reflux. Three types of replacement valves have been developed by various researchers: mechanical, bioprosthetic, and polymer. For the polymeric replacement valves, Moriyama developed two prosthetic valves made by electrospinning polyurethane fibers onto a stent [63]; Sathe designed a naturally closed prosthetic venous valve composed of Poly(vinyl-alcohol) (PVA) cryogel [62, 64-66]; and Midha developed a naturally open prosthetic venous valve with a lemon shaped orifice made with PVA [66].

While a transcatheter prosthetic venous valve has the potential of being an effective minimally invasive solution to venous reflux, particularly in the deep venous system, an adequate valve has yet to be developed. While venous reflux and outflow obstruction are major contributors to the development of CVI, none of the existing valves have been demonstrated to reduce reflux below that seen in individuals with venous reflux while also not increasing outflow resistance to venous obstruction levels. Of the few valves which have been tested in humans, only one has reported to have remained both patent and competent inside an individual for more than a year, but this valve was deemed unfit to further use for venous implantation [40]. Regarding the recent development of the Midha valve, it was suggested that thrombus had formed in response to elevated shear rates induced by radial buckling of the valves; the base of the valve had a propensity to radially buckle because of the ovular shape of the shoulder; and there is a tendency of the valve's leaflets to prolapse under retrograde pressure. Thus far prosthetic valves tested in animals or humans have commonly reported concerns with: thrombogenicity; biocompatibility; correct sizing, and subsequent fixation and functionality of the valve.

There is a need to develop a novel transcatheter prosthetic venous valve that has low thrombogenicity, is biocompatible, is sized correctly, is sufficiently competent, does not significantly obstruct forward flow, and can function in a distensible vein.

SUMMARY OF THE INVENTION

For a prosthetic venous valve to be developed which is effective in treating individuals with CVI, design specifications must first be determined. Additionally, verification tests must be developed which determine if a prosthetic venous valve meets these specifications. Therefore, the invention provides specify design specifications which are necessary for a prosthetic venous valve to effectively treat individuals with venous reflux. The invention further provides a prosthetic venous valve capable of meeting all design specifications. In certain embodiments, the finite element and computational fluid dynamic simulations, as well as certain verification tests, are performed to analyze the invention valve. The invention also provides validation tests for the invention valve with unique specify valve sizes and configurations that are suitable to be placed in certain locations in animals and humans.

More specifically, the invention provides the design, analysis, pre-clinical testing, and evaluation of a novel prosthetic venous valve. In certain embodiments, design specifications for an effective prosthetic venous valve were created. Verification tests were developed and performed which demonstrated that the valve met every design specification.

In certain embodiments, the invention provides a novel prosthetic venous valve with unique geometry features including, but not limited to, a normally open configuration with slits at the downstream end for rapid closure and a body that is longer than wide. In certain embodiments, the invention provides a prosthetic venous valve comprising two major parts: 1) a base that is cylindrical; and 2) leaflets that extend downstream of the base. The base and leaflets are joined in a transition region defined herein as the "shoulder".

In certain embodiments, the shoulder transition region is thinner than 3 mm in wall thickness.

The cylindrical base preferably has a length greater than its diameter. The wall of the base is thin with a thickness less than 2 mm, preferably less than 1 mm, and even more preferably less than 0.5 mm. The shape of the base is circular when deployed into the vein, but can be of indefinite shape when collapsed into a catheter.

In certain embodiments, the base of the invention valve is composed of only polymer or partially of polymer. In certain embodiment, the base optionally contains metal pieces, which can act as struts to maintain the base in a cylindrical configuration, and/or further expand the base to extert a pressure on the vein walls. In other embodiments, the metal pieces act as a stent and extend below the polymer portion of the base. The polymer covers part or all of the metal stent. In certain embodiments, the polymer in the base further contains a bioactive agent or drug.

In certain embodiments, the leaflets are longer than half the diameter. The leaflets are thin with a thickness less than 1 mm, preferably less than 0.5 mm at the tip. In certain embodiments, the tip of the leaflet assumes an oval or ellipsoidal or "lemon shape" that has a lumenal cross-sectional area less than the lumen of the base. The leaflets circumscribe a minor and major axis in luminal cross-section, with the minor axis diameter being smaller than the major axis diameter. The minimum distance between the tips of the leaflets in the deployed configuration is less than the internal diameter of the base.

In certain embodiments, the leaflets are configured to be joined around the periphery at all points. In other embodiments, the leaflet tips contain one or more slits in the long axis direction. The slits are preferably 0.1 mm wide and greater than 1 mm long.

The prosthetic valve of the invention is made in a range of sizes and lengths. Preferably, the diameter of the base of the valve is less than 40 mm with a corresponding length of base at least 1 mm greater than the diameter.

In other embodiments, the implantable prosthetic valve of the invention is constructed of a polymeric material that is biocompatible. To increase biocompatibility, the valve of the invention is preferably made of a hydrogel material. Biocompatibility is determined by a series of tests required by the US FDA as the International Standard ISO-10993, "Biological Evaluation of Medical Devices Part 1: Evaluation and Testing" (aka "the Tripartite tests"). In certain embodiments, the valve of the invention is made of poly vinyl alcohol (PVA). Detailed descriptions of the poly vinyl alcohol (PVA) cryogel and/or hydrogel can be found in the U.S. Pat. Nos. 5,981,826 and 6,231,605, the entire contents of which are hereby incorporated by reference. In other embodiments, the valve of the invention is made of other biocompatible polymers, including but not limited to, poly urethane or polyester. In certain embodiments, polyurethanes are used to make the venous valve of the invention.

In certain embodiments, the valve of the invention is constructed of a polymeric material with low thrombogenicity upon exposure to whole blood. The valve is designed to limit the shear rates at the wall because the shear rate extrema are thrombogenic. In certain embodiments, finite element and computational fluid dynamics simulations were performed to analyze the valve of the invention. In certain embodiments, the shear rates are greater than 1 $s^{-1}$ on all the walls and less than 100,000 $s^{-1}$ at the leaflet tip. Preferably, the shear rate at the wall is restricted to between 25 $s^{-1}$ and 10,000 $s^{-1}$. In certain embodiments, a maximum shear rate of 2300 $s^{-1}$ was calculated in the valve of the invention during the high forward flow after a Valsalva maneuver. A test of thrombogenicity of the material under static and shear conditions are provided.

The valve leaflets of the invention also have sufficient flexibility to open and close without a hinge. A test of tensile elasticity can be used to identify a polymeric material suitable for sufficient flexibility. An example test is described as: "ASTM E2769—15 Standard Test Method for Elastic Modulus by Thermomechanical Analysis Using Three-Point Bending and Controlled Rate of Loading". In certain embodiments, the modulus of elasticity of the biocompatible polymeric material is less than 10 MPa, preferably less than 1 MPa and even more preferably less than 500 kPa.

The valve leaflets of the invention also have sufficient tensile strength to withstand the backpressures in veins. In certain embodiments, the tensile strength of the polymeric material is greater than 50 kPa, preferably greater than 500 kPa, and even more preferably greater than 700 kPa.

The invention provides that the flexibility and strength are achieved with a PVA hydrogel material with greater than 10% by weight. The PVA hydrogel is further strengthened by a free-thaw cycling process that increases strength.

Further, the venous valve of the invention is designed to be flexible to fit into a hollow catheter for delivery. Thus, the valve of the invention can be fit inside a tube of a specific inside diameter and further be fit in a catheter with inside diameter at least 1 mm smaller than the outside diameter of the base. Preferably, the collapsed valve fits into a 16 Fr catheter.

In certain embodiments, the base of the valve is 1.5 times the diameter of the vein in which it is to be implanted to help correct orientation upon deployment. In other embodiments, the invention provides that the fluid behind the valve's leaflets is ejected with a forward flow rate of 400 mL/min, suggesting that thrombus formation will not occur at this location. In certain embodiments, the invention provides that a stented valve of the invention remained patent in a porcine blood flow loop for 3 hours, and the valve of the invention remains competent without buckling in a constricted vein at rest. In certain embodiments, the invention provides that the valve of the invention can expand to fit a vein with a maximum diameter 1.4 times the valve's initial diameter with low risk of tearing or leaflet prolapse.

Moreover, in certain embodiments, the valve of the invention is designed to resist reflux flow with fluid pressures greater than 30 mmHg and 160 mmHg. In certain embodiments, the valve of the invention has a reflux flow rate of less than 5 ml/min. In other embodiments, the invention provides that, on the average, the valve of the invention allows less than 0.5 mL/min of reflux at low and high retrograde pressures even after 500,000 cycles, indicating that it will reduce the reflux of individuals with venous reflux by more than 99.4%.

The valve of the invention is also designed to allow forward flow with a minimum of outflow resistance. In certain embodiments, the valve of the invention has an outflow resistance of less than 20 mmHg*min/L. In certain embodiments, the invention provides that the valve of the invention increases the outflow resistance an average of 2.3 mmHg*min/L which is much less than obstruction levels, e.g., ≥5 mmHg*min/L.

The invention further provides that the valve of the invention closes in less than 0.07 seconds and allows the distal pressure to rise to an average of 7% of the equilibrium pressure 30 seconds after a simulated ankle flexion.

Comparisons of the valve of the invention with previously developed prosthetic venous valves are also provided. The valve of the invention is the only valve to meet all design specification for an effective prosthetic venous valve, and therefore shows great potential to be a minimally invasive treatment for deep venous reflux.

These and other aspects of the present invention will be apparent to those of ordinary skill in the art in the following description, claims and drawings.

DETAILED DESCRIPTION OF THE INVENTION

Figure 1:
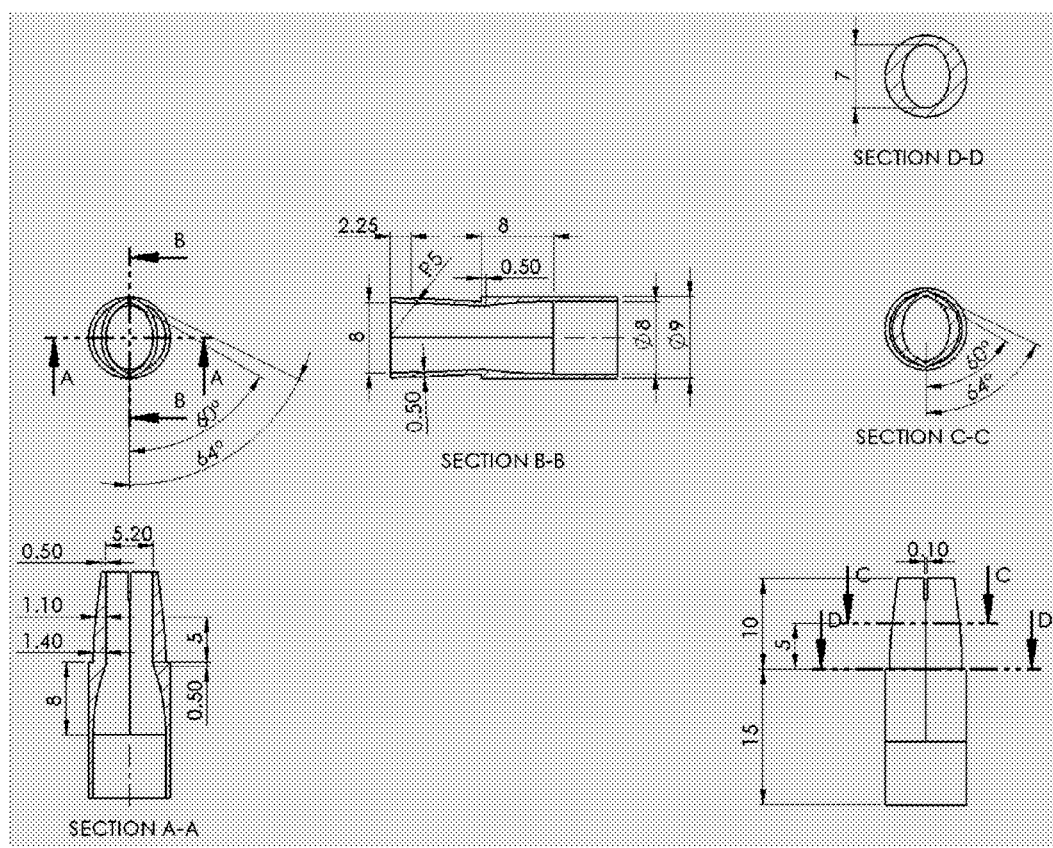
FIG. 1. Drawings and dimensions of the prosthetic venous valve of the invention.

The invention made novel contributions in the field of prosthetic venous valve development in the areas of valve design, design specifications, verification testing, computational analysis, and valve placement.

Valve Design

The invention provides a prosthetic venous valve with novel features that include the slits in the leaflet corners to improve sealing and the shape of the leaflets to help prevent prolapse. In certain embodiments, the invention provides that the transition of the prosthetic venous valve orifice from being elliptical to lemon shaped from the shoulder to half the height of the leaflets, which helps to prevent leaflet prolapsed, and then the remaining lemon shaped, which promotes sealing, is also unique. The invention further provides that the design of a valve can expand from its initial diameter by more than 40%.

Design Specifications and Verification Testing

Previous design specifications for reflux have been based on the volume ejected from the calf muscle pump or the amount of flow through the femoral vein when at rest in the supine position [64, 66]. However, the specification for competency of the invention valve was made relative to the amount of reflux seen in individuals with venous reflux, ensuring that the prosthetic valve of the invention that meets this specification can reduce the amount of reflux below the level that contributes to CVI symptoms. The invention provides measuring the reflux by weight, which increased the precision of the test. Additionally, the invention further provides specifications for the diameter of a constricted vein in which a valve is to remain competent and not buckle.

The invention further provides a unique specification for the closing time of the prosthetic valve of the invention, as well as measuring the closing time using a visual recording. While previous researchers have recorded the rise in distal pressure after a simulated calf flexion, a definitive design specification has not previously been suggested for this test [63]. In certainly embodiments, the invention provides a design specification for outflow resistance, which ensured that the valve of the invention did not impede flow to the level of venous obstruction.

In certain embodiments, a similar washout test was performed for the Midha valve which applied a 75 mmgHg pressure head using water [66]. The resulting forward flow rate in Midha's washout test was approximately 2700 mL/min, which is higher than the maximum flow of 1600 mL/min seen in the femoral vein, which biased the test towards washing out [59, 66, 71]. In certain embodiments, the invention provides a washout test that used a forward flow rate of 400 mL/min, corresponding to the flow rate of a subject in the supine position, being the situation where the valve is most likely to develop stagnant flow. Additionally, a glycerol solution with a similar viscosity as blood was used as the working fluid, further making the washout test of the invention more indicative of flow behind the valve's leaflets in a human vein.

The invention further provides a stented prosthetic venous valve capable of being placed in a porcine blood flow loop. A mathematical model to estimate the minimum catheter size in which the prosthetic venous valve of the invention can be fit is also provided.

Computational Analysis

The invention for the first time provides a finite element simulation to analyze the prosthetic venous valve of the invention. In certain embodiments, the invention provides that the material properties of 20 wt % PVA undergoes 4 freeze-thaw cycles at a slow thawing rate used in the finite element simulation.

While other CFD simulations of prosthetic valves inside the femoral vein have been performed, the invention for the first time provides a use of the deformed geometry of the valve when expanded by a stent in the vein (see FIG. 7), the physiologic maximum flow rate of 1600 mL/min, or a fully developed flow profile at the inlet to decrease the computational burden of the model [59, 60, 66].

Valve Placement

The invention also for the first time provides a method to determine the minimum distance between implanted prosthetic venous valves in the same venous segment, as well as a method to determine the diameters in which a prosthetic venous valve can be placed and maintain full functionality. The invention further provides a set of vein valve sizes which could service the CFV, femoral, and popliteal veins. A guide for surgeons to select the correct valve size is also provided.

EXAMPLES

The invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

Design Specifications

Competency

The primary function of a prosthetic venous valve is to reduce retrograde flow. Greater reflux flow rates have been correlated with increases in symptom severity [19, 67]. Neglén measured the time average reflux flow rate for incompetent CFV (n=47), femoral (n=87), and popliteal (n=103) deep veins to be 3-3357 mL/min [19]. A competent prosthetic venous valve should have a time average reflux flow rate below 3 mL/min to ensure reflux is reduced below pathologic levels.

A valve must remain competent under all of the potential retrograde pressures it may encounter in a vein when an individual is standing. Retrograde pressure in veins is caused primarily by the hydrostatic pressure from the column of blood above it which can range from 30 to 100 mmHg [2, 68-69]. The Valsalva maneuver can increase backpressure up to an additional 30 mmHg [70]. Thus a venous valve could experience retrograde pressures ranging from 30 to 130 mmHg. Applying a safety factor of 1.25 to the maximum pressure, a competent prosthetic valve will have a reflux flow rate less than 3 mL/min under backpressure ranging from 30 to 160 mmHg.

A vein may not be fully distended when the valve is required to close, such as when a Valsalva maneuver is performed in the supine position. The diameter of the average CFV at rest in the supine position is approximately 17% smaller than during a Valsalva maneuver in the 15% reverse Trendelenburg position [71]. Assuming that a valve is sized to fit into a vein when it is fully distended, it will need to remain competent when the vein's diameter is 17% smaller. A valve intended to be inserted in a 10 mm vein would need to remain competent when its leaflets were constrained inside a 8.5 mm tube or smaller. As a lower retrograde pressure is less likely to force a valve closed, this test should be performed under a 30 mmHg pressure head. Determining the smallest diameter in which a prosthetic valve can remain competent will also be helpful to direct surgeons in inserting an appropriately sized valve into a vein.

Fatigue Life

A prosthetic venous valve must remain competent after undergoing extensive cyclical loading. It has been predicted that a prosthetic valve would undergo 9 million cycles over the course of 10 years in a subject, with valves cycling at a rate of 0.67 Hz during walking [64]. It is assumed that a valve produced under good manufacturing practices will have a longer fatigue life than a valve produced in laboratory conditions. Thus if a prototype valve manufactured in a laboratory can function properly after 5% of the expected number of cycles (500,000), then it can be assumed that it would still function after 9 million cycles when produced with good manufacturing practices [64]. Thus a competent and fatigue resistant valve would have a reflux flow rate less than 3 mL/min under 30 and 160 mmHg of retrograde pressure before and after 500,000 cycles.

Closing Time

Healthy native venous valves typically close in less than 0.5 seconds under retrograde pressure, with valves with longer closure times typically being deemed incompetent in clinical practice [17-21]. Thus, in addition to restricting retrograde flow, a prosthetic venous valve should close in less than 0.5 seconds to be deemed competent.

Distal Pressure Rise

Contraction of the calf muscle pumps blood out of veins which decreases venous pressure. Pressure returns to the original level as the vein refills from arterial inflow and valvular reflux. This pressure rise is captured by recording the 90% venous refill time (VFT90), which is measured by recording the time it takes for venous pressure to rise back to 90% of the initial pressure after calf flexion. Individuals with CVI have a VFT90 of less than 30 seconds, while normal individuals have a VFT90 greater than 30 seconds [2, 22-23]. Lower VFT90 measurements have been correlated with increased symptom severity [13, 23]. Assuming that reflux from a healthy venous valve is responsible for 10% or less of the pressure rise, a prosthetic valve should see its distal pressure rise to 10% or less of the original pressure 30 seconds after a simulated calf flexion.

Outflow Resistance

A prosthetic venous valve should not significantly impede venous return to the heart. Flow resistance is calculated by:

$$R = \frac{\Delta p}{Q} \quad (1)$$

Where $\Delta p$ is the pressure difference and Q is the flow rate.

Because veins are distensible, their resistance changes with pressure. Therefore, it is important to compare venous resistance at similar pressures. At a forward pressure difference of 15 mmHg, the average venous resistance in a normal individual calculated by Equation (1) is 10 mmHg*min/L [27]. Four grades of obstruction, each resulting in an increase in venous resistance, have been specified [27]. The lowest grade of obstruction has been reported to increase the average venous resistance by 5 mmHg*min/L at a forward pressure gradient of 15 mmHg [27]. A prosthetic venous valve should not increase venous resistance as much as venous obstruction grade levels do. Thus a prosthetic venous valve should add less than 5 mmHg*min/L to the outflow resistance under a forward pressure difference of 15 mmHg.

Thrombogenicity

A prosthetic venous valve should have low thrombogenicity. While there is no standard method to quantify the degree of a device's thrombogenicity, items that have been shown to promote thrombus formation should be systematically reviewed. Virchow's Triad proposes that thrombus formation in the veins can occur in the presence of stagnant blood, endothelial injury, and blood hypercoagulability [72]. Of these three factors of the triad, a prosthetic venous valve may contribute to the formation of stagnant blood which could result in thrombus formation. In contrast, regions with high shear rates and the material used can increase the risk of thrombus formation. Ultimately, the formation of thrombus when the valve is placed in blood will determine if it is thrombogenic.

Stagnation Zones

Virchow found that stagnant blood increases the risk of thrombosis [72]. Blood behind the leaflets of a prosthetic venous valve has the highest risk of being stagnant and clotting. Stagnation zones behind the leaflets are unlikely to exist while the leaflets are cycling, such as when standing, sitting, or walking. However, when a person is in the supine position, there is typically only prograde pressure, so the leaflets may remain open and motionless for long periods of time [15]. Venous flow rates of an individual resting in the supine position are between 400 to 600 mL/min, which are lower than when standing, further increasing the risk of stagnation zones in this position [59, 73-74]. All of the fluid behind its leaflets can wash out under a forward flow rate of 100 mL/min, preferably 400 mL/min.

Radial buckling of a valve could create stagnant zones and result in clotting. The valve developed by Midha is suspected to have thrombosed for this reason [66]. The average CFV diameter at rest in the supine position is approximately 17% smaller than its diameter during a Valsalva maneuver [71]. Assuming that a valve is sized to fit into a vein when it is fully distended, it must not radially buckle when the vein is at rest and the diameter is smaller. A valve should not radially buckle when placed in a tube with a diameter that is 17% smaller than the diameter size it is designed to fit in. For instance, a valve intended to fit inside a 10 mm vein should not radially buckle in a 8.5 mm tube.

Regions of High Shear

High wall shear rates have been shown to increase platelet activation and binding, ultimately leading to thrombus formation and growth [75-77]. High shear rates also lead to increased platelet transport and deposition rates [78-80]. The maximum thrombus growth rate in human blood occurs at a wall shear rate of roughly 10,000 $s^{-1}$ [81-82]. Physiologic shear rates are generally considered to be below 3500 $s^{-1}$ [83]. The highest shear rate in the valve will occur when flow through it is the highest. The peak flow rate through the femoral vein can be up to 1600 mL/min, which can occur during ankle flexion while standing or after a Valsalva maneuver [59, 71]. To avoid shear induced thrombosis and to have shear rates at physiologic levels, the maximum shear rate of the blood flowing through a prosthetic venous valve at a rate of 1600 mL/min is required to be below 3,500 $s^{-1}$.

Material Biocompatibility

A valve should be composed of a material that has been shown to be biocompatible and have low thrombogenicity. The selected material must demonstrate its biocompatibility by not eliciting inflammation or a foreign body reaction, manifesting as fibrous encapsulation, when placed in the bloodstream, as well as passing the biocompatibility tests specified by ISO and USFDA [84-85]. While there is no standard method to quantify the degree of a material's thrombogenicity, a material that requires at least as much time for thrombus to form on it when exposed to blood as a material currently used in FDA cleared blood contacting devices, such as Dacron™, is assumed to have low thrombogenicity.

Blood Flow Loop

One way to test the short term patency and relative thrombogenicity of a valve is to place it in an in vitro blood flow loop. Porcine blood has a non-Newtonian flow behavior and viscoelasticity similar to human blood [86-88]. Porcine blood will thrombose at low and high shear rates, similar to human blood [77, 86, 89]. In addition to similarity, porcine blood has been found to thrombose faster than human blood [89]. For these reasons, porcine blood can be used to accurately predict a device's performance in human blood and is advantageous to use in a short term test.

Midha demonstrated that his valve was less thrombogenic than Sathe's by placing it in a flow loop with heparinized (3.5 mL/L) porcine whole blood flowing at a rate of 470 mL/min: the Sathe valve occluded in 18 minutes while the Midha valve was still patent after three hours [66]. A prosthetic venous valve should demonstrate that its short term patency in heparinized (3.5 mL/L) porcine blood is no worse than the Midha valve under a similar flow rate. Flow rates of this magnitude can occur when an individual is in the supine position, so a valve should be oriented in the horizontal direction when verifying this specification for the gravitational force to be in the correct direction [59, 73-74].

Deliverability

The demand by patients and surgeons for a prosthetic venous valve that can be percutaneously delivered by a catheter is much greater than one that requires an open surgery. Catheters sized 16 Fr (5.3 mm) and smaller are commonly used by surgeons and have shown better results when used in abdominal aortic aneurysm repair [90]. Thus a prosthetic valve should fit inside a 16 Fr catheter or smaller.

A valve will not function properly if it is placed inside a vein in an incorrect orientation. To promote a stable orientation, the length of the portion of the valve in contact with the vein wall should be at least 1.5 times the diameter. Hence a valve designed to fit inside a 10 mm vein should have a 15 mm long section in contact with the wall.

Summary of the design specifications for the prosthetic venous valve of the invention are summarized in Table 1.

TABLE 1

Summary of design specifications for a prosthetic venous valve.

| | Metric | Units | Specification |
|---|---|---|---|
| 1 | Reflux rate under a 30 mmHg pressure head | mL/min | ≤8 |
| 2 | Reflux rate under a 160 mmHg pressure head | mL/min | ≤8 |
| 3 | Smallest diameter in which the valve remains competent | mm | ≤8.5 |
| 4 | Reflux rate under a 30 mmHg pressure head after 500,000 cycles | mL/min | ≤8 |
| 5 | Reflux rate under a 160 mmHg pressure head after 500,000 cycles | mL/min | ≤8 |
| 6 | Leaflet closing time | s | <0.5 |
| 7 | Distal pressure rise 30 seconds after a simulated calf flexion | % | ≤10 |
| 8 | Outflow resistance added by the valve under a 15 mmHg pressure head | mmHg* min/L | <5 |
| 9 | Fluid behind leaflets washes out under 400 mL/min | Binary | 1 |
| 10 | Smallest diameter in which a valve does not buckle | mm | ≤8.5 |
| 11 | Maximum shear rate on the valve walls with an inlet flow rate of 1600 mL/min | $s^{-1}$ | <3500 |
| 12 | Material does not elicit inflammatory response or foreign body reaction when placed in the bloodstream | Binary | 1 |
| 13 | Material passes biocompatibility tests specified by ISO and USFDA | Binary | 1 |
| 14 | Material is less thrombogenic than Dacron | Binary | 1 |
| 15 | Time to occlusion when running heparinized (3.5 mL/L) porcine blood in a flow loop | Hours | >3 |
| 16 | Minimum catheter size the valve can fit in | Fr | ≤16 |
| 17 | Ratio of the valve length that contacts the vein wall to the vein diameter | NA | ≥1.5 |

Example 2

Valve Design and Fabrication

Material Selection

Prosthetic venous valves are typically mechanical, bioprosthetic, or polymer valves. A polymer valve is desirable because a mechanical valve may not be able to function in a distensible vein, and a bioprosthetic valve would be difficult to manufacture in large quantities.

Poly(vinyl-alcohol) cryogel (PVA) was chosen as one of the polymeric materials used for the prosthetic venous valve of the invention. PVA is a relatively new and promising biomaterial developed by researchers [91-92]. PVA is prepared by combining Poly(vinyl-alcohol) pellets with water to obtain a desired wt %, heating in an autoclave at 120° C. until the pellets have dissolved. At this point the PVA is in a viscous state and can be used to coat solid objects, such as stents, or be injected molded and assume the shape of a desired geometry [62, 66, 93]. The liquid PVA is then solidified by cross-linking which occurs during freeze-thaw cycling.

PVA meets the requirement of being biocompatible. PVA passed the biocompatibility tests specified by ISO and USFDA [85]. When placed in the bloodstream of sheep and rats, inflammatory responses and fibrin encapsulation have not occurred [66, 93-94]. Furthermore, medical devices containing PVA have been implanted in humans for over ten years without any negative reports [93].

PVA meets the requirement of having low thrombogenicity. PVA has been shown to be less thrombogenic than Dacron™ when profused with porcine blood [65, 95]. The thrombogenicity of PVA can be reduced further by its ability to incorporate and elute anticoagulation drugs, such as citrate [66]. Additionally, it is difficult for cells to attach to PVA because the proteins necessary for adhesion do not easily absorb into it [96].

The mechanical properties of PVA can be altered by modifying the solution's wt % and the thermo cycling process [97-108]. Increasing the PVA wt % from 10 to 20 percent has been found to increase the ultimate tensile strength and Young's modulus by up to 192% and 250% respectively [97]. The ultimate tensile strength and Young's modulus have been found to increase for each freeze-thaw cycle, with diminishing increases per cycle after the fourth cycle [99-100, 105-1-7]. For example, Fromageau reported that the mean Young's modulus for a 10 wt % PVA solution increased by 77-104 kPa (57-320%) for cycles 1 through 4 and by 16-20 kPa (6-7%) for cycles 5 and 6 [99]. Decreasing the rate of freezing and thawing has been found to increase the stiffness by up to 340% for the same wt % [98-99]. One study found the Young's Modulus of PVA having undergone 4 freeze-thaw cycles to remain stable for a period of 7 months without significant variation, suggesting that the valve leaflets will remain flexible in the long-term [103].

In the present application, the PVA needs to be flexible enough to close under low pressures, yet stiff enough to resist prolapse under backpressure. To accomplish these goals, prototype valves were made out of 20% PVA and underwent four freeze-thaw cycles. For each cycle valves were frozen at −20° C. for at least three hours. The rate of thawing was decreased by placing valves in a 4° C. refrigerator instead of at room temperature for at least three hours.

Geometry

Figure 2:
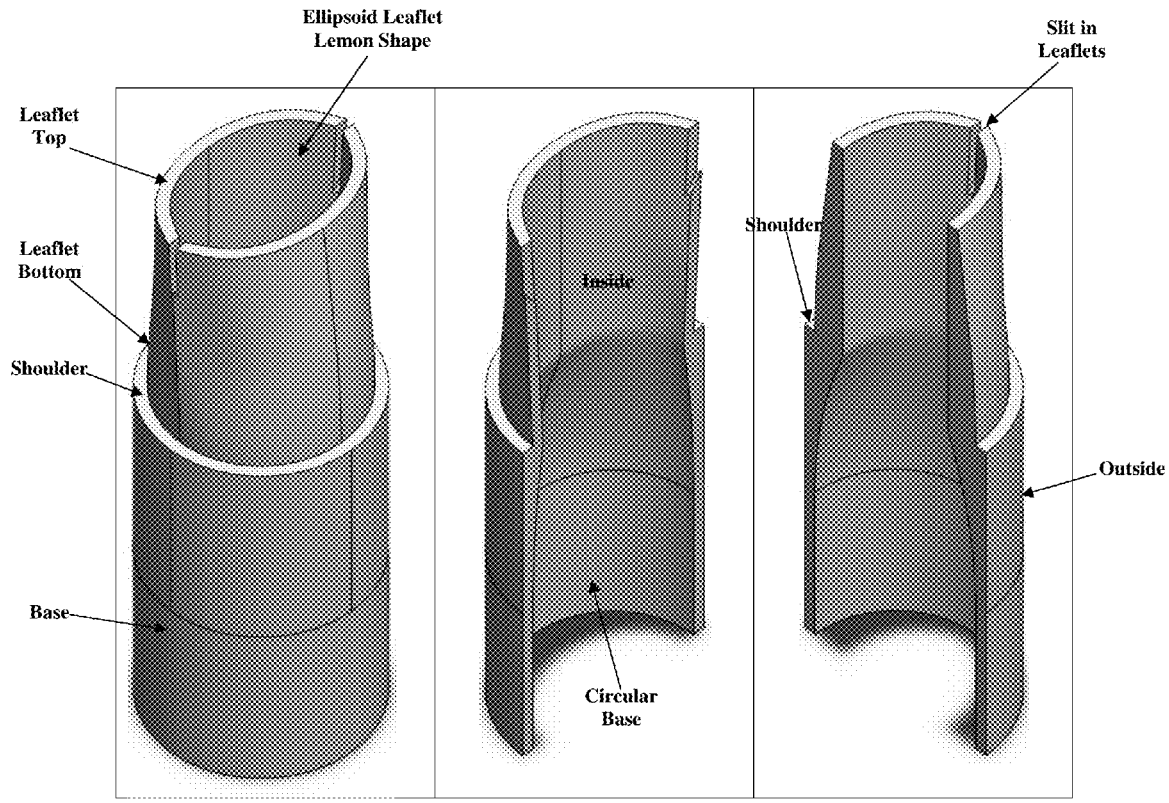
FIG. 2. Isometric views of the inventive prosthetic venous valve geometry (left) and halved along the major (middle) and minor (right) axes.
Figure 3:
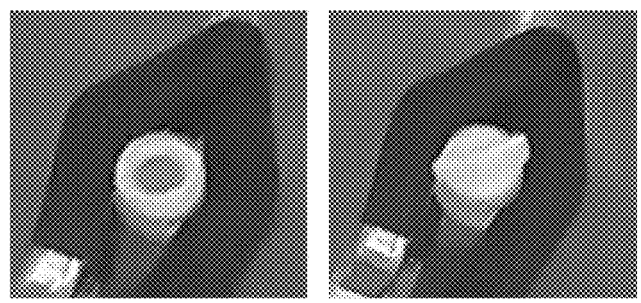
FIG. 3. Proximal views of the prototype valve when open (left) and closed (right).

A prosthetic venous valve of the invention was designed to fit a 10 mm vein and meet the aforementioned design specifications. The valve's geometry is shown in FIGS. 1 and 2. The valve has two general regions: the base, which includes the valve's entry region and shoulder, and the leaflets.

The base of the valve is circular and has an outer diameter slightly smaller than the average diameter of the human femoral vein, which decreases the overall bulk of the valve. The circularity allows a stent to be placed inside the base of the valve during manufacturing. The stent can cause the valve base to expanded inside of a vein and provide the necessary radial pressure to fix its position. This expansion decreases the risk of radial buckling and potential clotting at the inlet while enabling the valve to fit perfectly into a large range of vein sizes. The wall thickness at the base is thick enough to expand with the stent without tearing while keeping the overall bulk of the valve low. The base is 15 mm long, which ensures that there is only one stable orientation for the valve when it is inserted in a vein. The valve shoulder is 0.5 mm wide and encourages washout of blood behind the leaflets. The top of the stent is coincident with the shoulder which supports the base of the leaflets and reduces the risk of prolapse without interfering with leaflet function. Thus the shoulder also helps the stent to be placed correctly inside of the valve mold during manufacturing. The circular orifice at the entrance of the base transitions into an ellipse to allow the base to support the leaflets. This transition happens in a nonlinear manner that keeps the volume of the valve low while not raising the shear rate to critical levels with abrupt changes. The orifice of the valve in its unexpanded state is 29 mm$^2$ at its most constricted point, which occurs at the level of the shoulder, which is 36% of the area of a 10 mm circular vein.

The valve's leaflets are naturally open and are designed to close under retrograde flow. The pressure difference between the fluid on the inside and outside of the leaflets during retrograde flow causes the leaflets to move inward and close. The leaflets remain closed because of the hydrostatic pressure provided by the column of blood above them. Forward flow causes the leaflets to open again.

Several features were incorporated into the leaflet geometry with the intent to enable them to seal during closure while keeping shear rates low when they were open. As shown in FIG. 2, the elliptical orifice at the top of the valve's base linearly transitions from a circular shape at the base into a lemon or ellipsoid shaped orifice by the time it reaches half the height of the leaflets (section C-C in FIG. 1) after which it remains lemon or ellipsoid shaped. The linear transition helps keep the shear rate low while decreasing the risk of prolapse. The lemon shaped orifice with a 120 degree angle encourages the valve to close properly. The tips of the leaflets are 0.5 mm thick which allows the ends of the leaflets to be more flexible and seal better while decreasing the risk of tearing during removal from the mold during manufacturing. The 128 degree angle at the outside corner of the leaflets ensures that the smallest thickness of the leaflets is no less than 0.5 mm to avoid tearing during mold removal.

Various design iterations revealed that a decrease in the leaflet diameter along the minor axis of the orifice strongly correlated with a decrease in the amount of reflux in a valve. Thus the valve of the invention was designed to have this dimension as small as possible to decrease reflux while keeping the shear rates at levels below those that would increase the risk of platelet activation. The length of the orifice along the inner length was set as large as possible to decrease the maximum shear rate.

To further improve the sealing of the valve, 0.1 mm wide and 2.25 mm high slits are present at the top of the leaflets at the corners of orifice. These slits enable the leaflets to seal better by eliminating any gaps that would otherwise exist at the corners of the leaflets during closure. The slits were not made wider or longer because doing so could result in the leaflets not lining up correctly during closure. By including these slits in the original geometry, there is no need to later create the slits by cutting which could result in a crack at the bottom of the slit that would likely propagate during cycling. The leaflets along the major axis of the orifice flare out to ensure that the slits do not lie in the path of high velocity fluid flow, even when the valve base is expanded by the stent, which would otherwise result in a spike in the shear rate and increase the risk of platelet activation.

Additional features were incorporated into the leaflet geometry to reduce the risk of prolapse. As shown in FIG. 2, the bottoms of the leaflets along the minor axis of the orifice (shown in the second panel of FIG. 2) are the thickest portion of the geometry and resist over bending. The leaflets are 10 mm long which is intended to provide a friction force great enough to prevent the leaflets from sliding down each other. The internal leaflets along the minor axis of the orifice are vertical which was found to help the leaflets seal better and be less likely to prolapse than when angled. In particular, each valve leaflet tapers uniformly from a region at the transition from the base to the leaflet along the minor axis (as shown in the third panel of FIG. 2) which is thicker than the base to the leaflet along the major axis (as shown in the second panel of FIG. 2). The thickness of the leaflets at the top is uniform over the entire periphery (as shown in the second panel of FIG. 2).

Manufacturing

Physical valve prototypes of the invention valve design with and without stents were fabricated by injecting 20 wt % PVA into a two-part mold and then temperature cycling for four cycles. For valves combined with a stent, the stents were prepared and inserted into the mold prior to PVA injection. Details of the mold creation, stent preparation, and subsequent valve fabrication are as follows.

Mold Creation

The invention valve's geometry was modeled using Solid-Works® v 2012 CAD software (Dassault Systèmes Solid-works Corporation, Wltham, Mass.). The cylindrical base of the valve was extruded an additional 5 mm which would later assist in the manufacturing process without changing the length of the valve. Rigid rapid prototypes of the modified geometry composed of FullCure®720 were created using an Objet Eden250™ 3 D printer (Stratasys Ltd., Edina, Minn.). The prototypes were then placed in a container of the desired mold size and shape, with the cylindrical base of each prototype flush against the base of the container. A steel shim measuring 10 mm in diameter and 0.1 mm thick was placed in the leaflet slits of each prototype. The steel shims could later ensure the dimensional accuracy of each valve's slits during manufacturing.

A two part mold was chosen to make the valves to ensure that the valves could be removed from the molds without tearing or deflection of the stent. At this point in mold creation, four to six toothpicks were placed in the container which would later help align the two mold halves during valve fabrication.

Polydimethylsiloxane (PDMS) was chosen as the material for the mold primarily for its ability to accurately capture the small features of the proposed valve design. After curing, PDMS retains its shape in the presence of water and has a high melting point, allowing it to be in contact with PVA or cleaned in an autoclave without deforming [109]. PDMS is transparent which allows visual detection of unwanted air bubbles during PVA injection. PVA does not adhere to PDMS, enabling fabricated valves to be easily removed from the mold [62, 66].

PDMS was made from mixing a 10:1 ratio of parts A and B of Sylgard 184® (Dow Corning, Midland, Mich.) and then poured into the container around the outside of the rapid prototypes until the bottom 10-15 mm was filled. The container was then degassed in a vacuum chamber until all bubbles had been expelled from the PDMS. The container was then placed in an oven at 45° C. for at least two hours, allowing the top surface of the PDMS to solidify. A thin layer of Evercoat 105685 mold release (Evercoat, Cincinnati, Ohio) was poured on top of the PDMS around the outside of the rapid prototypes and allowed to dry at room temperature for at least 6 hours. The inside of the rapid prototypes and the remainder of the container were then filled with PDMS and degassed in a vacuum chamber until all bubbles had been removed. The container was then placed in an oven at 45° C. for at least four hours, allowing all of the PDMS to fully cure.

The solidified mold was then removed from the container. Water was used as a lubricant as the two halves of the mold were gently pulled away from each other and separated along the parting line. The toothpicks were cut at the level of the parting line and removed from the mold, allowing the two mold halves to be separated; the rapid prototypes remaining lodged inside the top mold half. The top half of the mold was then placed in a beaker of water at 100° C. The hot water served to soften the rapid prototypes allowing them to be removed from the mold using forceps without tearing the PDMS. Flutes for the leaflets were created by poking holes through the PDMS using a blunt needle.

5 mm tall cylindrical spacers having the same dimensions as the valve's base made of FullCure®720 were created using an Objet Eden250™ 3 D printer (Stratasys Ltd., Edina, Minn.). During valve fabrication, spacers were placed in the bottom of each valve cavity to help the cylindrical mold geometries be concentric. This also eliminated the presence of a parting line inside of the valves, decreasing the risk of clotting inside of the valves due to coagulation of blood caught in this region or a jump in the shear rate due to the sharp change in geometry. During valve fabrication, toothpicks were reinserted to help align the two mold halves correctly.

Stent Preparation

When the valve of the invention is implanted in an animal or human it is fixed in place by a stent. The risk of material related thrombosis increases if the metal stent is in direct contact with the blood. Weaver proposed coating a stent with PVA as a way to reduce the risk of material related thrombosis [93]. To ensure that each valve's stent was completely covered by PVA, stents were coated with PVA prior to mold insertion by following Weaver's method [93]. A 20 wt % PVA solution was prepared and autoclaved at 120° C. for 25 minutes. Stents were expanded with a balloon to 8.5 mm and then dip coated in 20 wt % PVA. Excess PVA inside each stent was manually removed using a wire. The stents were then placed in the freezer at −20° C. and thawed in the fridge at 4° C. three times to solidify the PVA.

The prosthetic venous valve of the invention is used to correct venous reflux in individuals with chronic venous insufficiency.

Example 3

Computational Analysis

Finite Element Model

A finite element model was created to obtain the geometry of the invention valve after being expanded by a stent into a 10 mm vein. The deformed geometry was then used in the computational fluid dynamics simulation.

Material Properties

As the strain in a PVA valve during its expansion by a stent is expected to be small, the material of the valve in this model is linearly elastic and isotropic. The Young's modulus of the PVA can be estimated from its manufacturing conditions. Fromageau reported that 10 wt % PVA undergoing four freeze-thaw cycles with slow temperature transitions had a mean Young's modulus of 286 kPa [99]. Weaver reported that increasing from a 10 to 20 wt % solution can increase the Young's modulus by 250%, suggesting that the stiffness of the PVA used in this application to be approximately 1000 kPa [97]. PVA is nearly incompressible, having a Poisson's ratio between 0.42 and 0.499 [98-99]. The Poisson's ratio used for this simulation was 0.45. The influences of the stent could be accounted for by the boundary conditions so the simulation assumed the material to be homogenous.

Model Creation

Figure 4:
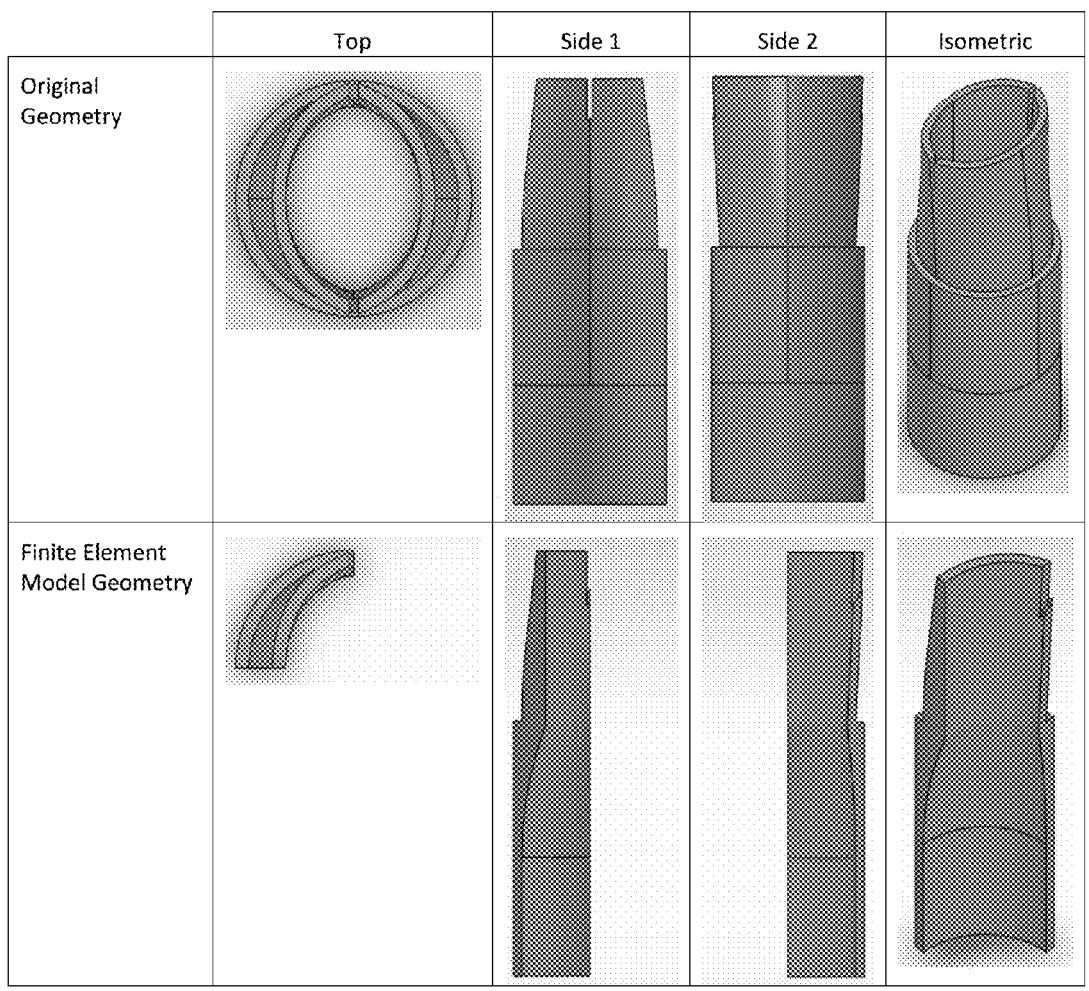
FIG. 4. Views of the original and finite element model geometry.

The original geometry of the invention valve was halved along its two planes of symmetry to reduce the geometry to a quarter of the original (FIG. 4). This symmetry was later utilized in the finite element simulation to reduce the computational burden without losing accuracy. The modified geometry was then exported into COMSOL and used in the finite element simulation.

Boundary Conditions

The following boundary conditions were applied to the model to simulate a stent expanding the base of the valve to fit inside a circular vein with a 10 mm inner diameter. The outer wall of the valve's base was constrained to displace 0.5 mm in the direction normal to its surface. The bottom of the valve's base was also constrained to not move vertically. Symmetry was enforced by constraining the portions of the valve on the planes of symmetry to not displace in the normal direction.

Mesh Refinement and Convergence

Eight meshes for the quarter model were created using COMSOL Multiphysics® v 4.2a with characteristics listed in Table 2. The smallest dimension on the vein valve is 0.5 mm so the smallest element size for the initial mesh was 0.5 mm. Additional meshes with element densities 2 to 8 times greater than the first mesh were also created. Each mesh used a moderate element growth rate of 1.5, a high resolution of curvature of 0.2, and a high resolution of narrow regions of 1. The convergence criteria for the iterative solver were 10E-6.

The simulation was performed and the resulting maximum total displacement magnitude was recorded for each mesh. The mesh with elements size six times as dense as the original mesh had the same total displacement as higher density meshes, indicating that this mesh was sufficiently refined.

TABLE 2

Element characteristics of meshes constructed during
mesh refinement for the finite element model.

| Relative Mesh Density | Max Element Size (mm) | Min Element Size (mm) |
|---|---|---|
| 1 | 2.5 | 0.5 |
| 2 | 1.25 | 0.25 |
| 3 | 0.833 | 0.167 |
| 4 | 0.625 | 0.125 |
| 5 | 0.5 | 0.1 |
| 6 | 0.417 | 0.083 |
| 7 | 0.357 | 0.071 |
| 8 | 0.313 | 0.063 |

Results

Figure 5:
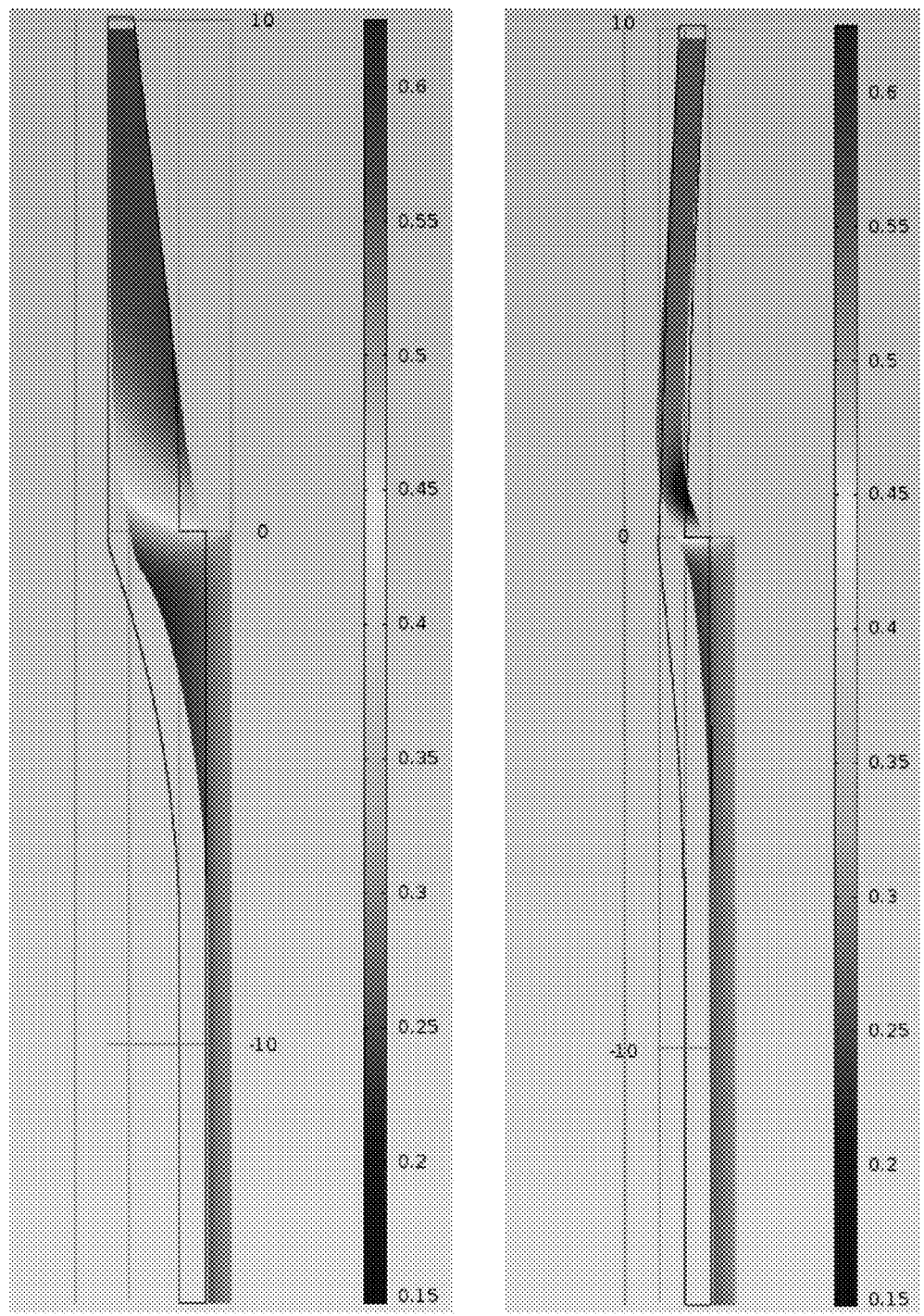
FIG. 5. 2D plots of total displacement magnitude on the first (left) and second (right) planes of symmetry of the finite element model with the valve's base displaced in the normal direction by 0.5 mm. Black wireframe lines indicate the original geometry.
Figure 6:
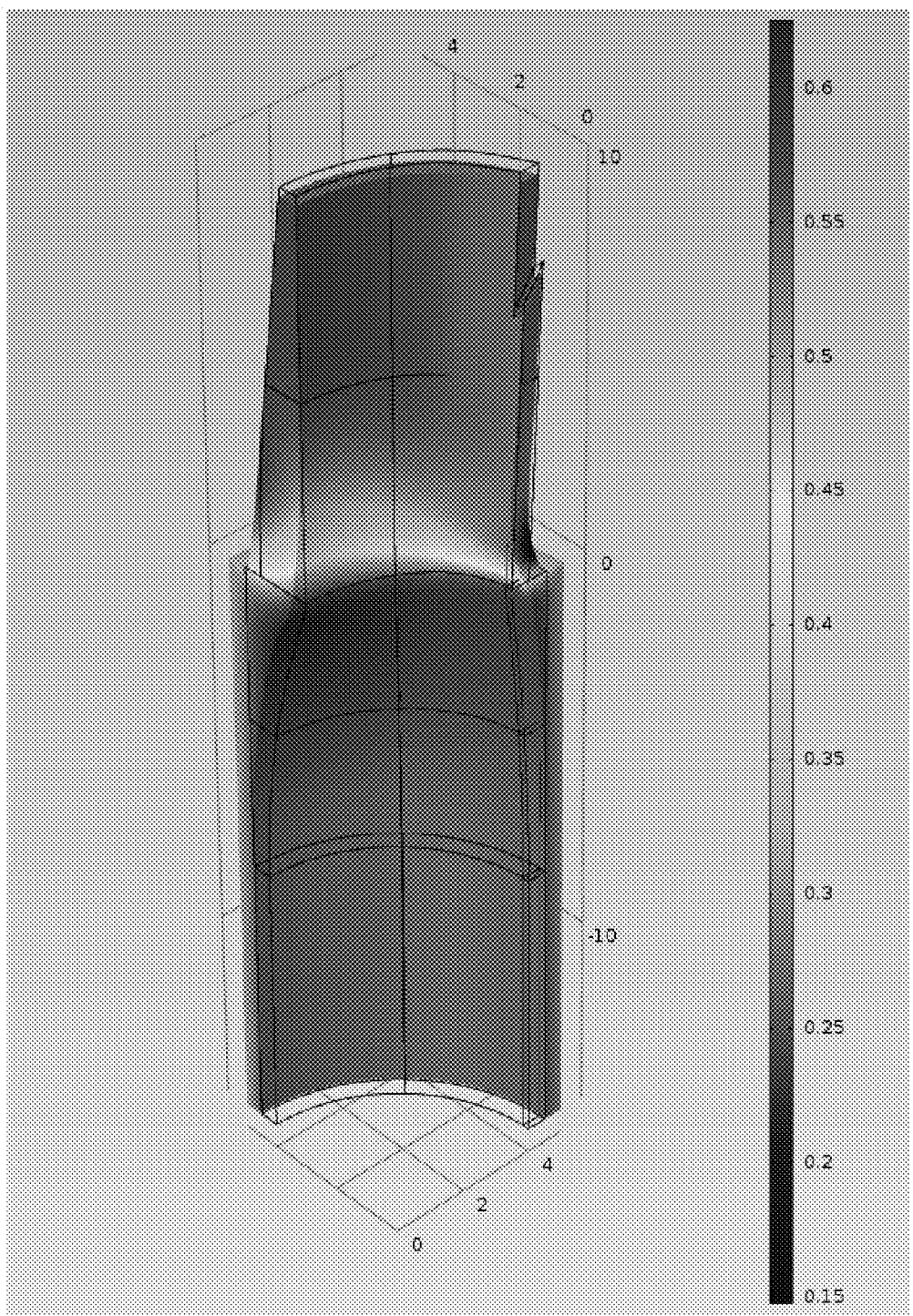
FIG. 6. 3D plot of total displacement magnitude in of the finite element model with the valve's base displaced in the normal direction by 0.5 mm. Black wireframe lines indicate the original geometry.

The deformed geometry of the finite element model with the valve's base displaced in the normal direction by 0.5 mm, simulating the expansion of the valve by a stent into a 10 mm vein, is shown in FIGS. 5 and 6. The maximum principle strain in the valve was 0.473, suggesting that the original linear elastic modulus was valid for this simulation. The leaflets expanded with the shoulder at their base and gradually transitioned back to their original geometry 4 mm above the shoulder (see Table 3). After expanding, the minimum orifice area of the valve remained approximately 28.4 mm$^2$, which is 36.1% of the cross-sectional area of the vein. This is within the stenosis range of 30-70% caused by native valves [14, 16].

TABLE 3

Orifice area of the original and deformed valve geometries
at specified distances above the shoulder.

| Distance Above Shoulder (mm) | Original Geometry: Orifice Area (mm$^2$) | Deformed Geometry: Orifice Area (mm$^2$) | % Increase |
|---|---|---|---|
| 0 | 28.6 | 36.9 | 29.0 |
| 1 | 28.7 | 32.2 | 12.1 |
| 2 | 28.6 | 29.8 | 4.2 |
| 3 | 28.5 | 28.8 | 0.9 |
| 4 | 28.4 | 28.4 | 0.0 |

Computational Fluid Dynamics Model

A steady state computational fluid dynamics (CFD) model was created to quantify the maximum shear rate of blood flowing through the proposed valve when expanded into a 10 mm vein at a rate of 1600 mL/min (2.67E-5 m$^3$/s) [59, 71]. The maximum shear rate is required to be less than 3,500 s$^{-1}$ with this forward flow rate for the valve to meet the design specification and to reduce the risk of shear induced thrombosis.

Material Properties

The working fluid in the simulation was blood, which was assumed to be homogenous and incompressible. While blood is inherently non-Newtonian, its viscosity becomes nearly constant above a shear rate of 100 s$^{-1}$ [110-112]. As the shear rates encountered in veins in this simulation are to be above 100 s$^{-1}$, blood was modeled as a Newtonian fluid with a viscosity of 0.00345 Pa-s and density of 1056 kg/m$^3$ [113].

The deformed geometry of the valve was assumed to be rigid because the deflection of the leaflets with forward flowing fluid observed during experimental testing was small. The vein wall was also assumed to be perfectly rigid. Both of these assumptions served to decrease the computational burden of the model while still obtaining meaningful results.

Model Creation

Figure 7:
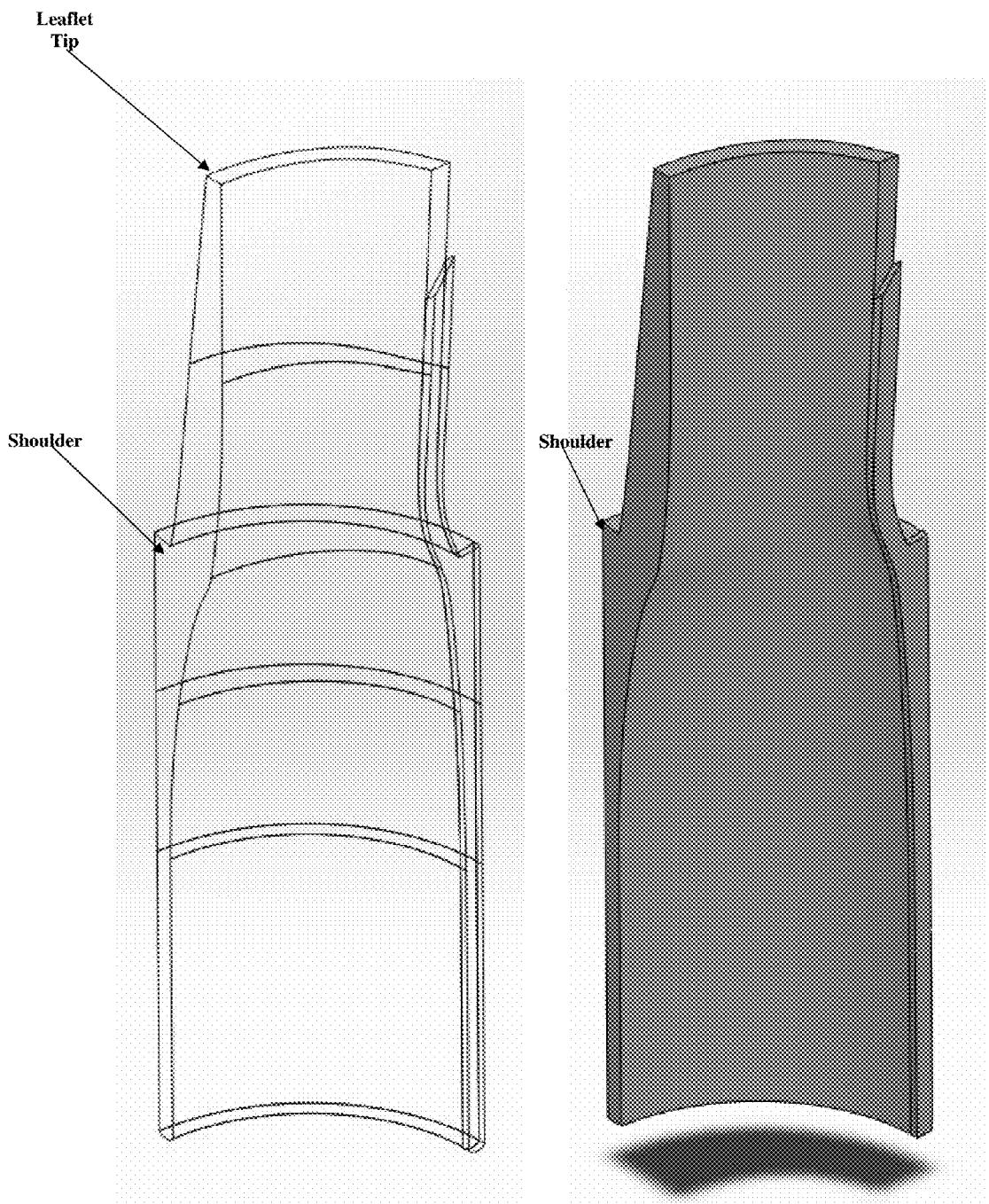
FIG. 7. 3D plot of points extracted from the deformed finite element simulation (left). CAD model of the expanded valve created from the extracted points (right).

The 3D locations necessary to create a wireframe of the surface of the expanded valve were extracted from the deformed geometry of the finite element simulation (see FIG. 7). SolidWorks® v 2012 was used to create surfaces from these points which were then lofted together by guide curves. The CAD model of the expanded valve is shown in FIG. 7.

A CAD model of the fluid domain of a circular 10 mm vein was created by modeling a 10 mm diameter cylinder 80 mm long. Two planes of symmetry were used to reduce this cylinder to a quarter of the original geometry. The fluid domain of a vein with the expanded valve inside of it was created by subtracting the geometry of the expanded valve from the quarter cylinder geometry (see FIG. 8). As flow through the inlet was programmed to be fully developed, the entry region was 5 mm. The exit region was 5 diameters (50 mm) to prevent any flow abnormalities at the outlet from influencing the flow through the valve.

Boundary Conditions

A no-slip condition was imposed on the valve and vein walls. Symmetry was enforced by constraining the velocity of the fluid on the planes of symmetry to be 0 m/s in the normal direction.

The Reynolds number is defined as:

$$Re = \frac{\rho \bar{u} D}{\mu} \quad (2)$$

Where Re is the Reynold's number, ρ is the density of blood (1056 kg/m$^3$), D is the vein diameter (0.01 m), μ is the viscosity of blood (0.00345 Pa-s), and $\bar{u}$ is the average velocity which can be stated in terms of the inlet flow rate:

$$\bar{u} = \frac{Q}{A} \quad (3)$$

Where Q is the inlet flow rate (2.67E-5 m$^3$/s), and A is the cross sectional area of the vein (7.85E-5 m$^2$). Equation (3) evaluates to 0.34 m/s, which is the average velocity at the inlet. By combining Equations (2) and (3), the Reynolds number at the inlet was found to be 1040, signifying that the flow will be laminar [114].

Poiseuille flow was assumed with a velocity profile in a circular tube of [114]:

$$u = \frac{r^2 - R^2}{4\mu} \frac{dp}{dx} \quad (4)$$

Where u is the fluid velocity, r is the radial distance from the centerline, and R is the radius of the vein (5 mm), and $$\frac{dp}{dx}$$

is the pressure drop. Poiseuille flow through a rigid circular tube can be described as [114]:

$$Q = -\frac{\pi R^4}{8\mu}\frac{dp}{dx} \quad (5)$$

Equations (4) and (5) can be combined to find the velocity profile in terms of the flow rate:

$$u = \frac{2Q(R^2 - r^2)}{\pi R^4} \quad (6)$$

Figure 8:
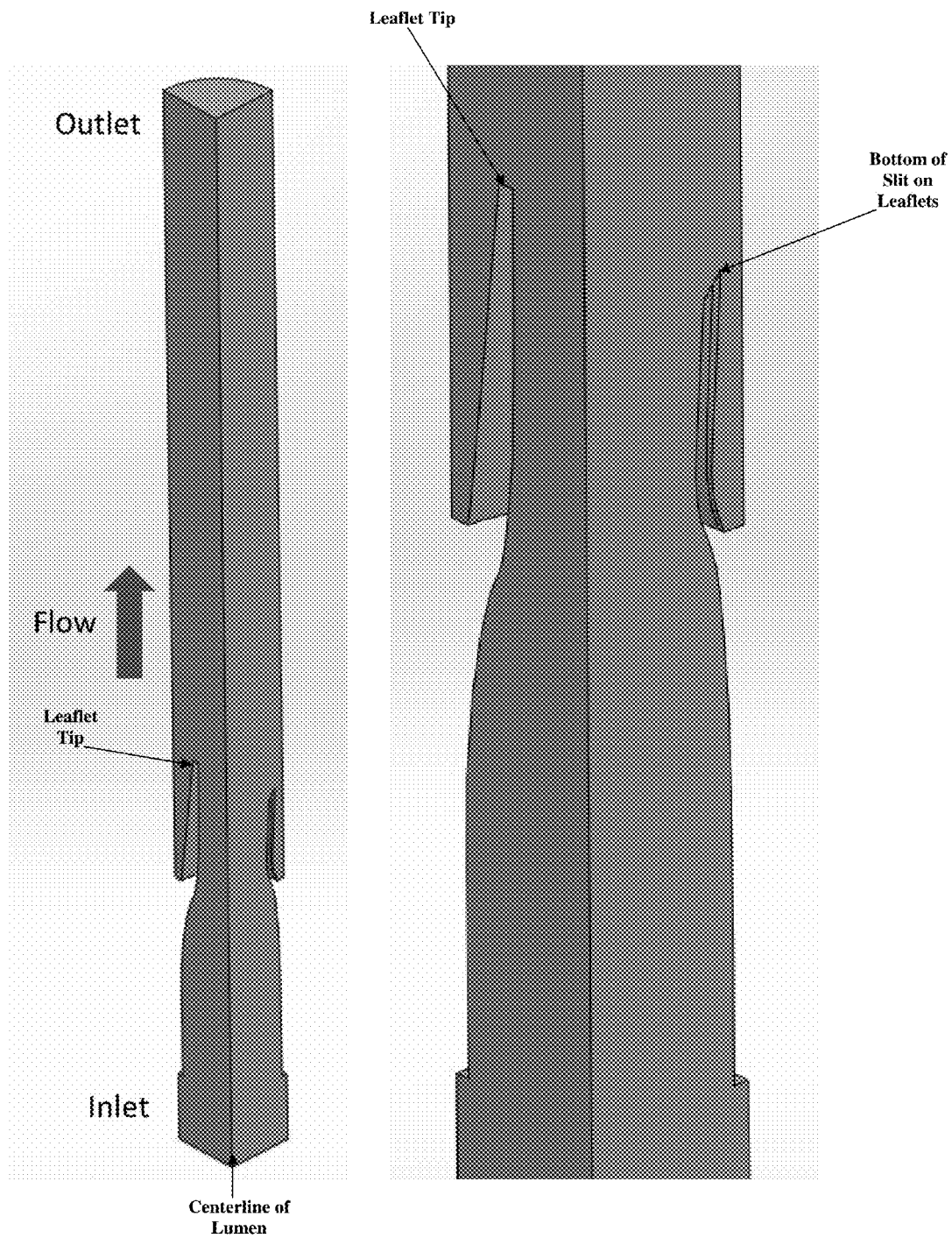
FIG. 8. View of entire fluid domain used in the CFD simulation (left). Zoomed in view of the portion of the fluid domain inside the deformed valve (right).

Equation (6) was used to impose Poiseuille flow on the inlet of a 10 mm diameter vein with a 1600 mL/min flow rate (see FIG. 8). A pressure of 0 Pa was imposed on the outlet (see FIG. 8).

Mesh Refinement and Convergence

Six meshes for the fluid domain of the expanded valve were created using COMSOL Multiphysics® v 4.2a with characteristics listed in Table 4. A similar approach used in meshing the finite element model was used, with the exception that the smallest element sizes were no smaller than those used in the finite element mesh. Each mesh used a moderate element growth rate of 1.5, a low resolution of curvature of 1, and a moderate resolution of narrow regions of 0.5. The convergence criteria for the iterative solver were 10E-6.

The simulation was performed and the resulting maximum velocity magnitude was recorded for each mesh. The mesh with elements five times as dense as the least refined mesh had a velocity magnitude within 3% of the highest density mesh, suggesting that this mesh was sufficiently refined.

TABLE 4

Element characteristics of meshes constructed during mesh refinement for the CFD simulation.

| Relative Mesh Density | Max Element Size (mm) | Min Element Size (mm) |
|---|---|---|
| 1 | 2.5 | 0.5 |
| 2 | 1.25 | 0.25 |
| 3 | 0.833 | 0.167 |
| 4 | 0.625 | 0.125 |
| 5 | 0.5 | 0.1 |
| 6 | 0.417 | 0.083 |

Results

Figure 9:
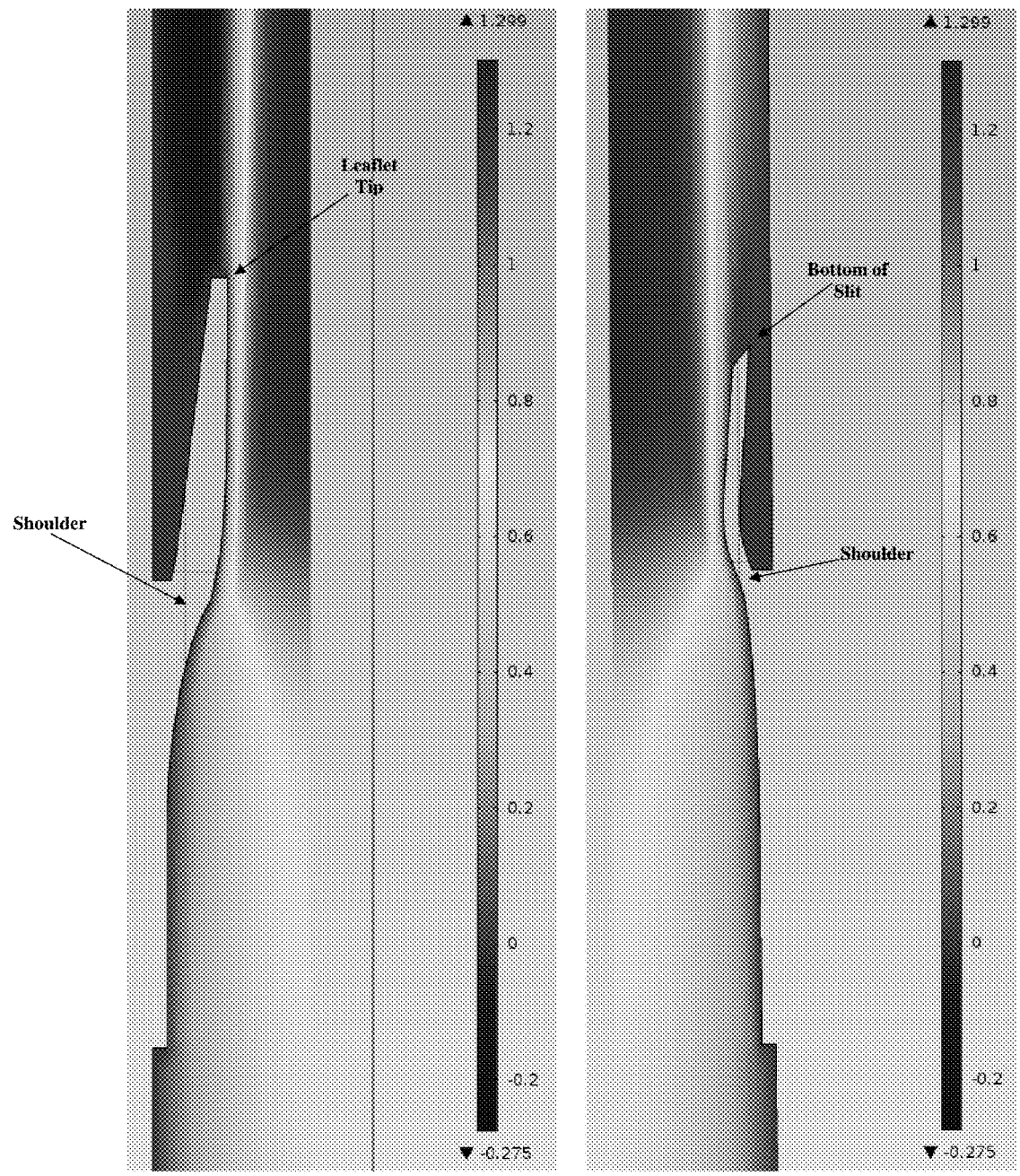
FIG. 9. 2D Contour plots of y velocity on the first (left) and second (right) planes of symmetry.
Figure 10:
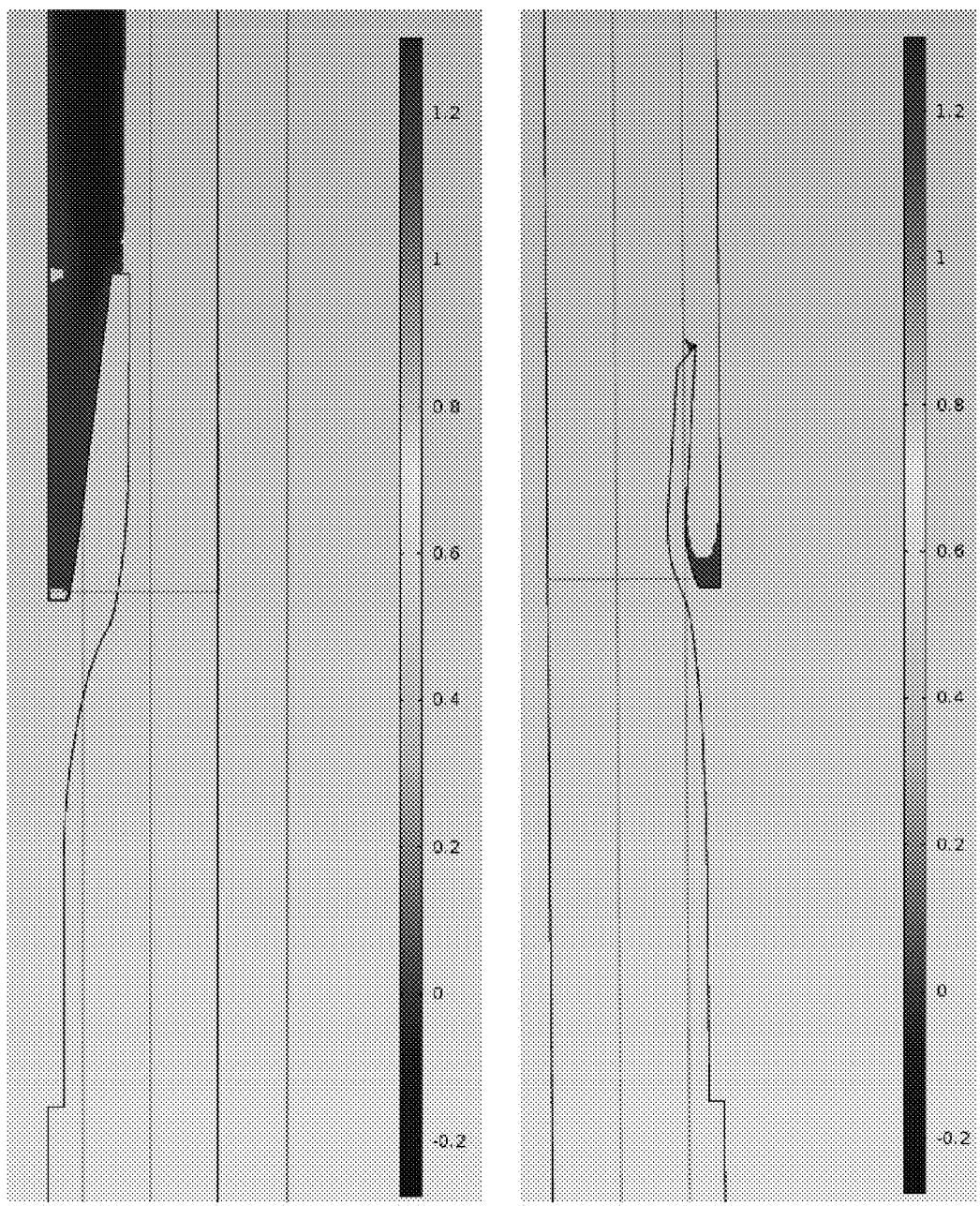
FIG. 10. 2D Contour plots of y velocity on the first (left) and second (right) planes of symmetry. Only regions of reverse flow are shown.
Figure 11:
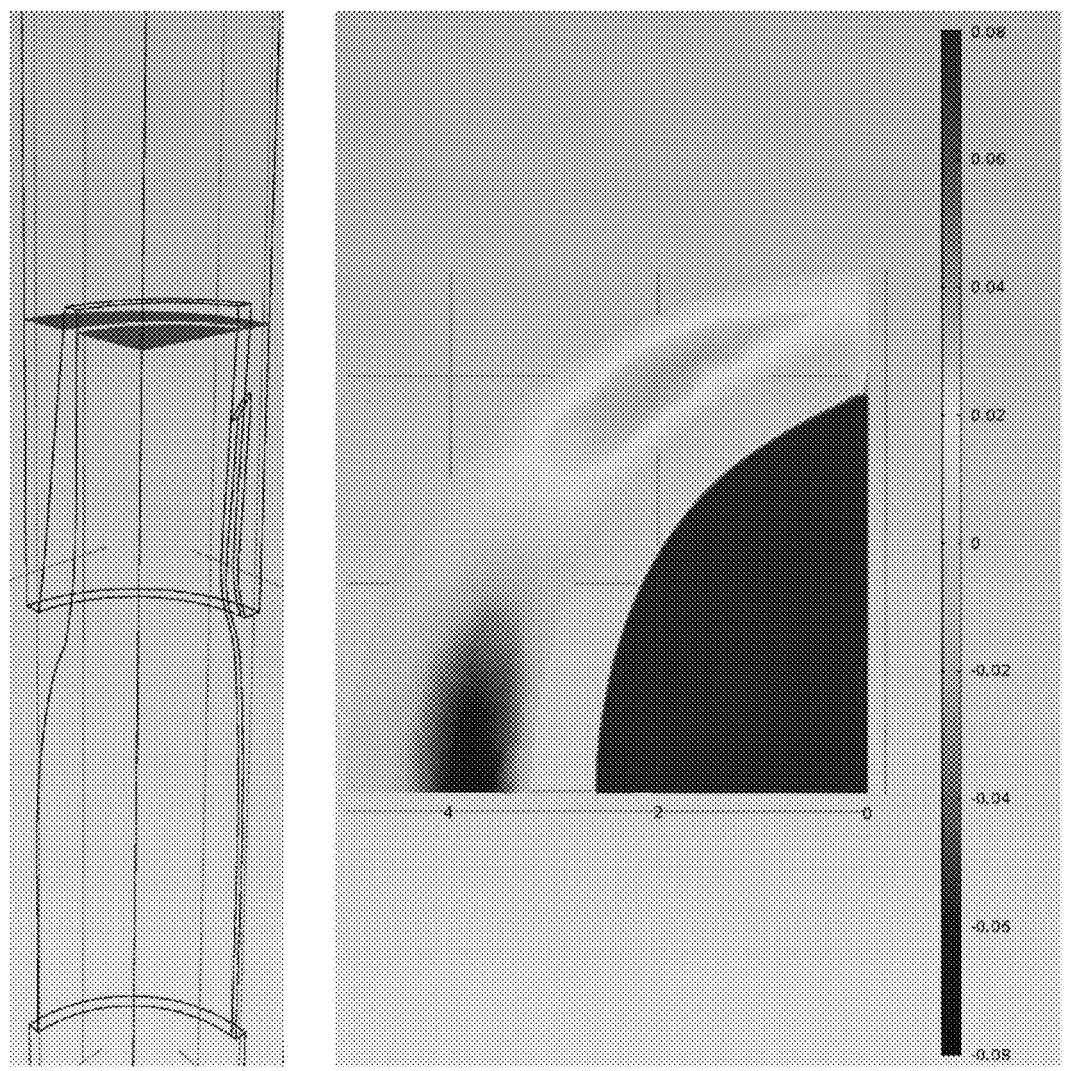
FIG. 11. Wireframe view of fluid domain with a horizontal plane, marked in red, intersecting the domain 9 mm above the valve's shoulder (left). 2D contour plot of y velocity on this plane (right); reversed flow, indicated by shades of blue, is into the page.
Figure 12:
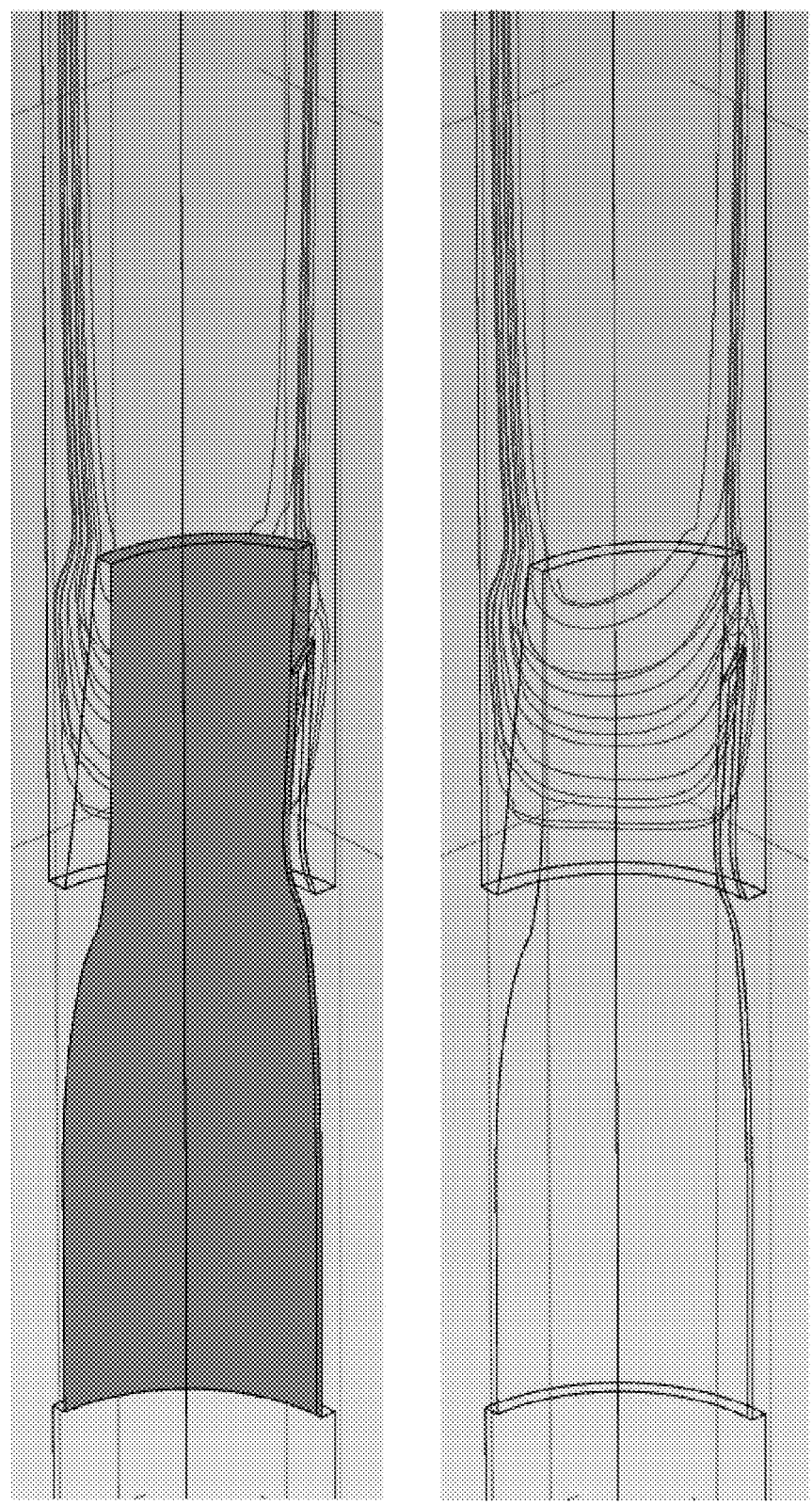
FIG. 12. 3D plot of streamlines behind the valve's leaflets with (left) and without (right) the valve's internal orifice wall and leaflet slit shaded gray. Streamlines indicate that flow is circulating behind the leaflets.

Fully developed flow entered the inlet of the valve and transitioned into a jet inside the leaflets (see FIG. 9). The centerline velocity increased from 0.679 to 1.299 m/s inside the valve. Reversed flow up to −0.08 m/s was observed behind the thicker leaflet (see FIGS. 10 and 11). Streamlines revealed that flow was circulating behind the leaflets (see FIG. 12).

Figure 13:
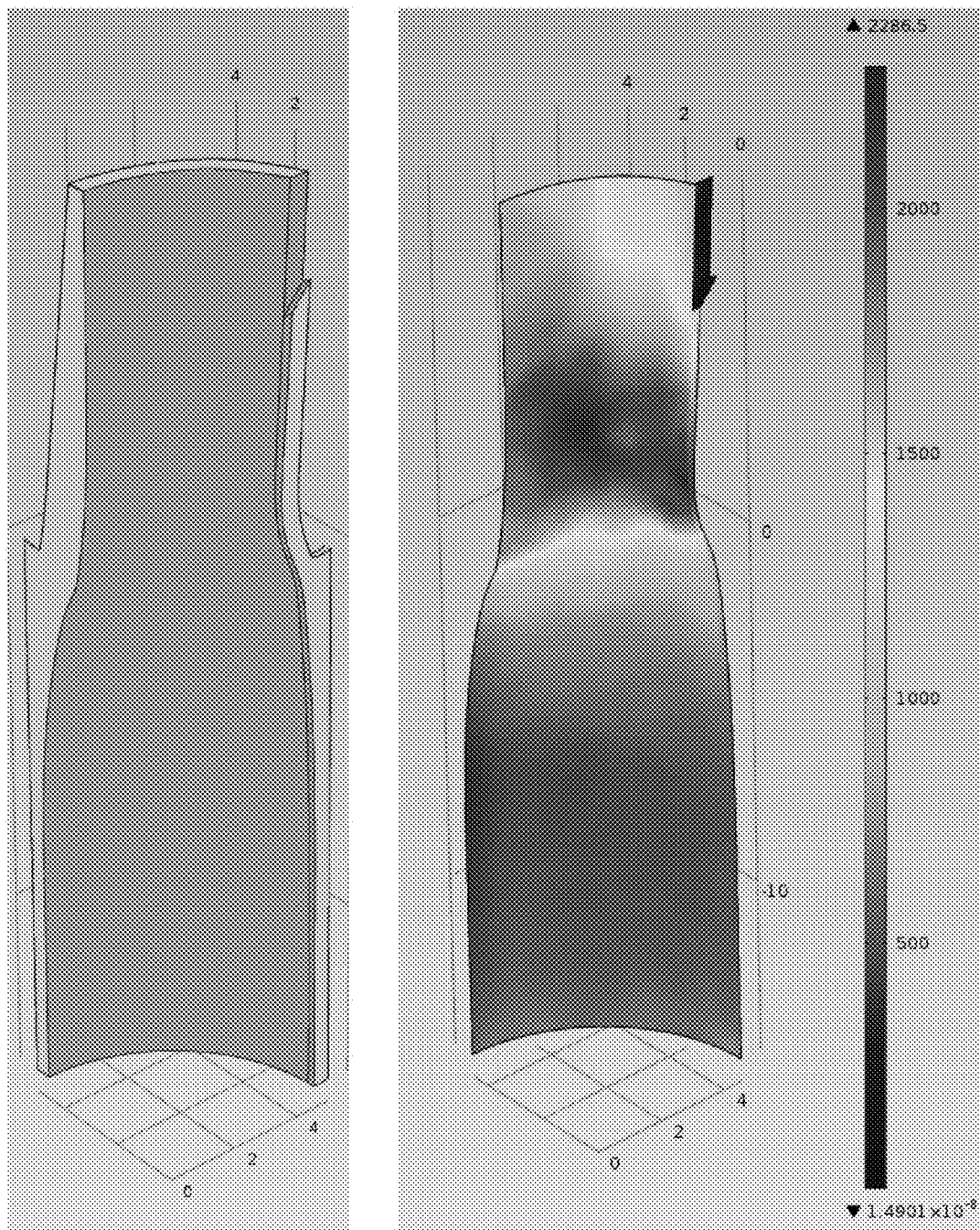
FIG. 13. 3D view of deformed valve's geometry with the inner walls and leaflet slit highlighted in purple (left). 3D contour plot of shear rate on the valve's inner walls and leaflet slit (right).

The maximum shear rate inside the proposed valve was 2300 s$^{-1}$, which was located on the internal wall of the leaflets (see FIG. 13). This meets the design specification of having a maximum shear rate less than 3500 s$^{-1}$.

Figure 14:
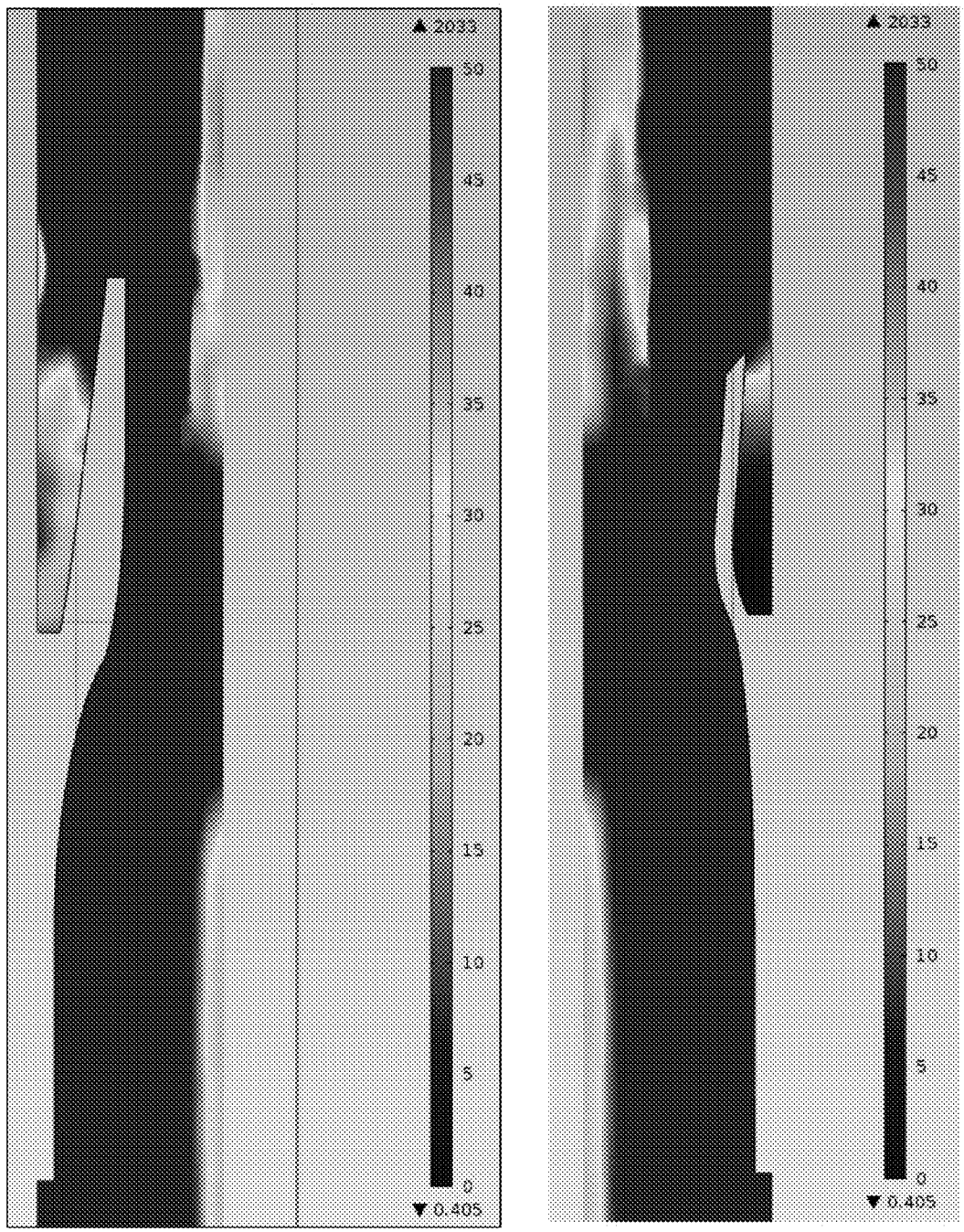
FIG. 14. 2D contour plots of shear rate on the first (left) and second (right) planes of symmetry emphasizing regions of low shear. Shear rates higher than 50 $s^{-1}$ are dark red.

Regions of shear rates below 50 s$^{-1}$ were found behind both leaflets (see FIG. 14). The shear rate behind the leaflets may increase upon leaflet closure, and blood may be washed out or clot in this region. High and low shear rates were not observed in or adjacent to the leaflet's slit, suggesting that this design feature may not increase the device's thrombogenicity (see FIGS. 13 and 14).

Example 4

Verification Testing

Preparation
PVA Tube Fabrication and Valve Fixation

15% PVA tubes, similar to those used by Sathe, were fabricated to simulate veins during the reflux flow rate, smallest competent diameter, distal pressure rise, and outflow resistance tests [62]. These tubes were 7 mm long, 1 mm thick and had 10 mm inner diameters. Like veins, these tubes distend under pressure and mimic the expansion seen in the sinus region of a native valve when the valve inside of them is closed [64].

The PVA tubes were created by injecting 15 wt % PVA in a mold made of two cylinders held concentric by two end caps. The mold then underwent three thermo cycles in a −20° C. freezer and a 20° C. room for at least three hours at each temperature. The tubes were removed from the molds after they were done cycling.

Valves without stents were then placed inside PVA tubes and fixed with Loctite liquid super glue (Düsseldorf, Germany) to simulate a valve being fixed inside a vein. After the glue had dried, the tubes with valves joined inside were then placed in water in preparation for testing.

Glycerol Solution Preparation and Properties

A 40 wt % glycerol solution was prepared to mimic the viscosity of human blood. The viscosity of the glycerol solution was measured to be 0.00349 Pa-s by a viscometer. This is within 1% of the generally accepted Newtonian viscosity of blood, 0.00345 Pa-s [194]. The density of the solution was measured to be 1088 kg/m$^3$ using a 100 micropipette and a scale. This solution was used to enhance the accuracy of the reflux flow rate, smallest competent diameter, distal pressure rise, outflow resistance, and washout tests.

Reflux Flow Rate
Methods

Figure 15:
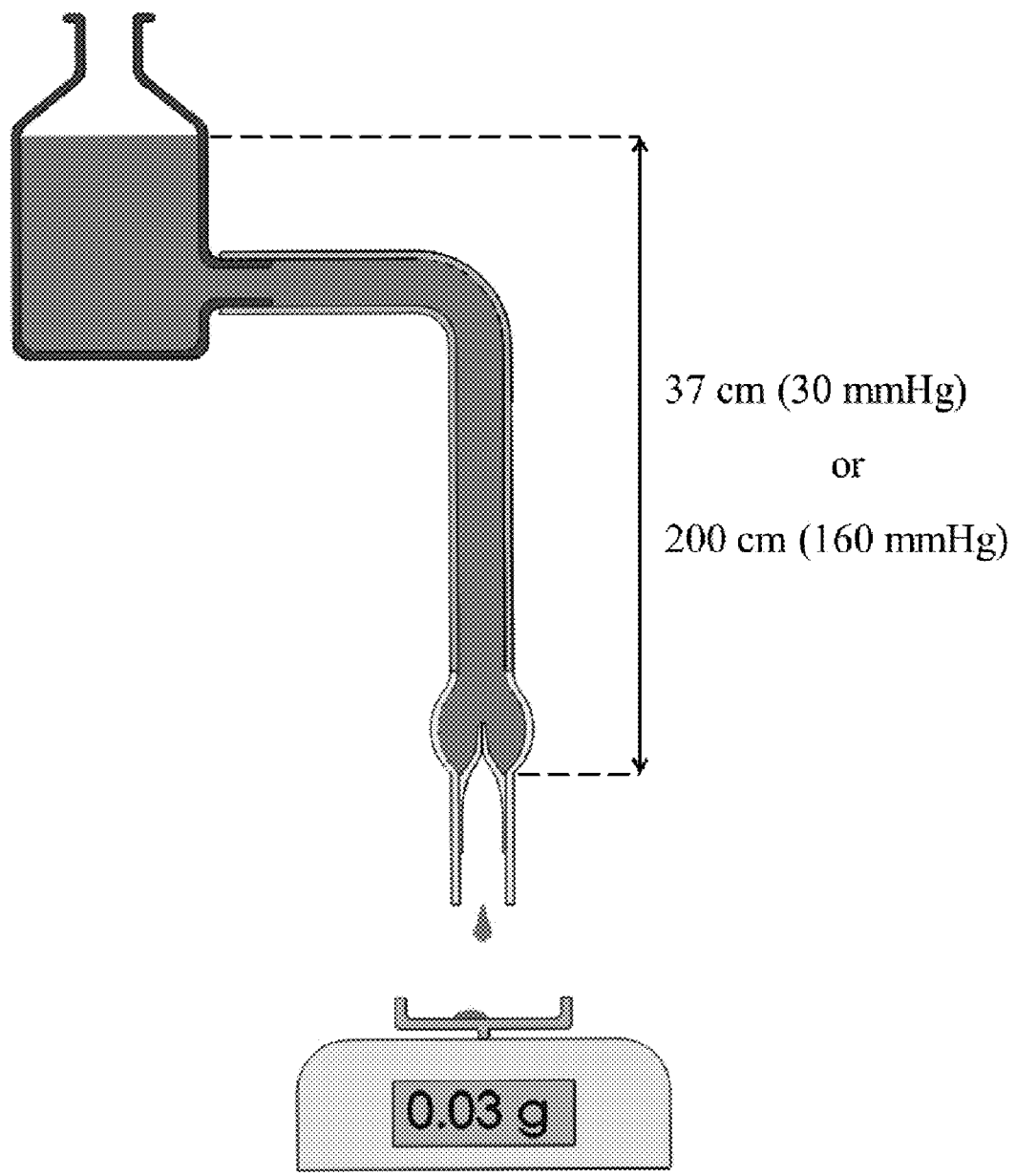
FIG. 15. Schematic of test setup to measure reflux flow rate. A column of glycerol induces a pressure to close the valve. The reflux flow rate is then measured using a scale and a stopwatch.

A test was developed to determine the average reflux rate of a prosthetic valve under 30 mmHg and 160 mmHg of retrograde pressure (see FIG. 15). The proximal end of a PVA tube with a valve glued inside was tied to 9 mm inner diameter Tygon tubing. The tubing was connected to a reservoir filled with a 40% glycerol solution which was elevated 37 cm above the valve's shoulder to create a retrograde pressure gradient of 30 mmHg. When testing the Midha valve, it was discovered that the rate of pressure increase, caused by variations in the time taken to get the reservoir to its elevated position, influenced the valve's competency, with faster rates raising the likelihood of leaflet prolapse. To decrease the variation of the pressure application rate, the distal end of the tube was manually squeezed closed after the reservoir was elevated. Entrapped air in the tube was then forced through the valve causing its leaflets to open. The tube was then released and the full pressure head was immediately applied to the leaflets.

The average reflux flow rate of the valve over time was then measured using a scale and a stopwatch. The scale weighed the amount of reflux with a resolution of 0.01 g. The density of the glycerol solution was used to convert grams to mL with the following relation:

$$\text{Volume} = \text{Mass} * 0.92 \frac{\text{mL}}{\text{g}} \quad (7)$$

The volume calculated using Equation (7) was then divided by the amount of time taken to expel it to find the time average reflux flow rate. Each valve was tested five times to find the mean and standard deviation of its reflux flow rate. Each test lasted for at least 1 minute.

The reservoir was then elevated to 200 cm above the valve's shoulder to create a retrograde pressure gradient of 160 mmHg. The test was repeated as outlined previously, and the mean and standard deviation of the reflux flow rate were found for each valve at this higher pressure head.

Results

Figure 16:
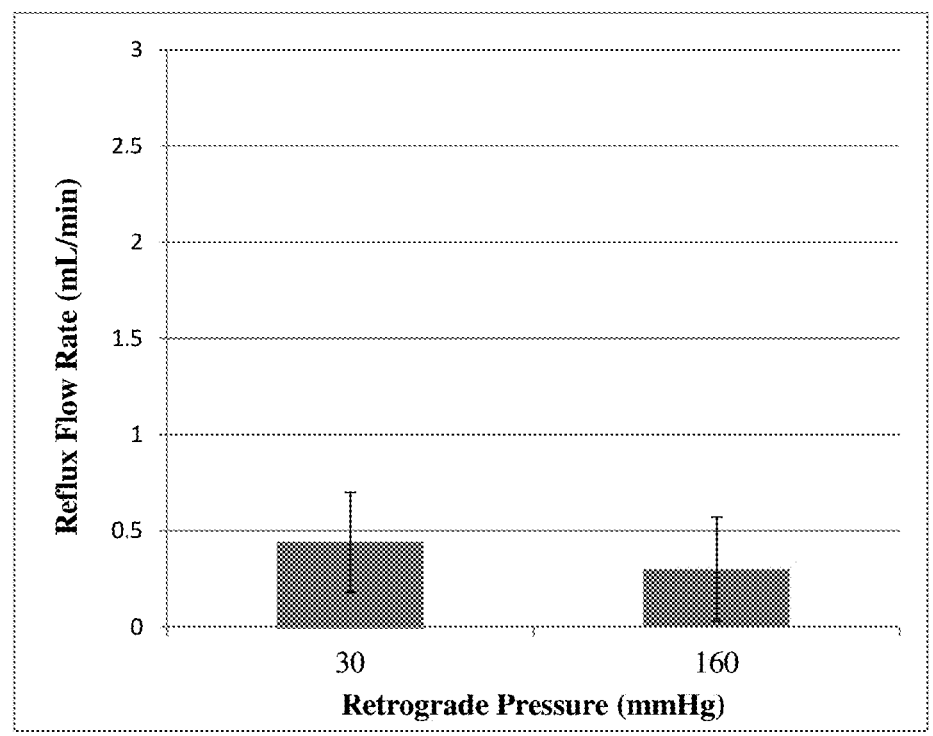
FIG. 16. Average reflux flow rate for the proposed valve at low (30 mmHg) and high (160 mmHg) retrograde pressures. The valve meets the specification of having a reflux flow rate of less than 3 mL/min.

The average reflux rate for five valve prototypes was found to be 0.44±0.26 and 0.30±0.27 mL/min under 30 and 160 mmHg pressure heads respectively (see Table 5 and FIG. 16). This corresponds to a 99.98-99.99% reduction in the average reflux flow rate compared to that without a valve. This suggests that the average reflux rate of the valve is from 0.30 to 0.44 mL/min along the entire pressure range of 30-160 mmHg, meeting the design specification of less than 3 mL/min.

Neglen measured the median reflux flow rate of incompetent CFV, femoral, and popliteal venous segments to be 318, 162, and 131 mL/min respectively [19]. Thus the invention valve would reduce the reflux flow rate in a typical incompetent CFV, femoral, or popliteal vein segment by more than 99.63% [19].

TABLE 5

Measured time average reflux flow rates for five valve prototypes at 30 and 160 mmHg.

| Valve | Time Average Reflux Flow Rate (mL/min) ± stdev | |
|---|---|---|
| | 30 mmHg | 160 mmHg |
| None | 2390 ± 70 | 3950 ± 270 |
| A | 0.19 ± 0.05 | 0.09 ± 0.11 |
| B | 0.69 ± 0.40 | 0.20 ± 0.10 |
| C | 0.40 ± 0.32 | 0.63 ± 0.07 |
| D | 0.72 ± 0.20 | 0.52 ± 0.03 |
| E | 0.18 ± 0.14 | 0.04 ± 0.07 |
| Average | 0.44 ± 0.26 | 0.30 ± 0.27 |

Smallest Competent Diameter

Methods

To determine the smallest diameter in which the invention valve can be remain competent, a set of 25 mm long rigid tubes comprised of FullCure®720 were created using an Objet Eden250™ 3 D printer (Stratasys Ltd., Edina, Minn.) with inner diameters ranging from 6.5 to 10.0 mm in increments of 0.5 mm. A rigid tube was placed around the leaflets of a valve glued inside a PVA tube. A 30 mmHg pressure head from the 40% glycerol solution was created using the same setup as the reflux flow rate test. A valve was deemed competent if its leaflets still closed in spite of the constriction of the rigid tube around them. If the valve was still competent, the rigid tube was removed and a smaller diameter replaced it. The largest diameter at which the valve leaflets did not close was recorded and the diameter 0.5 mm larger was assumed to be the smallest diameter in which a valve could remain competent.

Results

The leaflets of the valve did not close when constricted by the 7.5 mm rigid tube. This suggests that the smallest diameter in which the valve remains competent is 8 mm. This meets the specification of being 8.5 mm or less.

Fatigue

Methods

Figure 17:
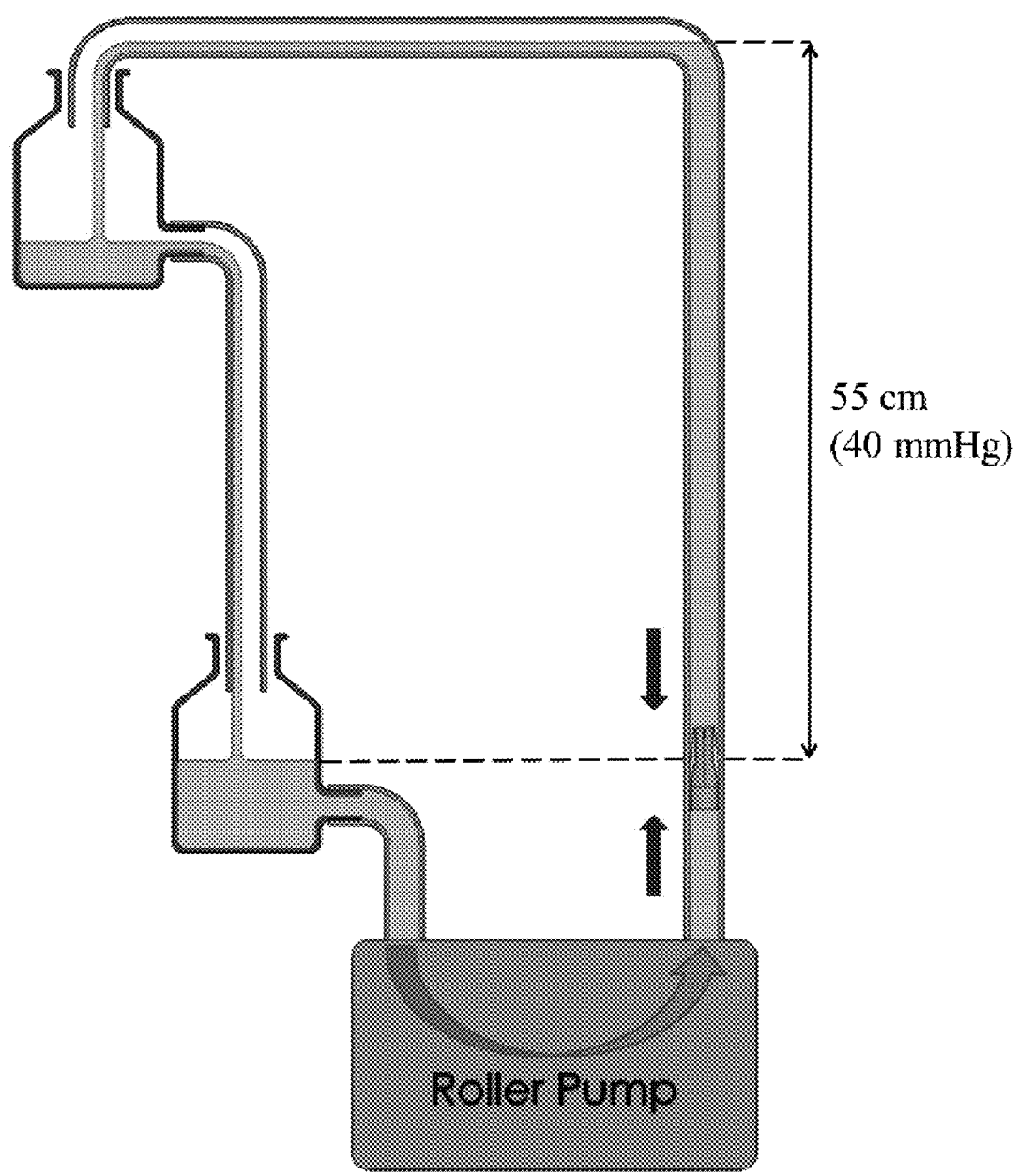
FIG. 17. Schematic of fatigue test. Pulsatile flow is created by a column of water creating a 40 mmHg retrograde pressure head which closes the valve and a roller pump which induces forward flow to open the valve. The valve closes whenever the roller pump is not inducing full forward flow.

A flow loop was created to cycle a valve open and closed (see FIG. 17). A valve was placed on a connector having a 7 mm inner diameter and 9 mm outer diameter at its most constricted point. The valve on the connector was then placed inside transparent tubing having an inner diameter of 10 mm. This segment of tubing was then connected to the rest of the flow loop. The loop was then filled with water. A column of water 55 cm above the valve provided a 40 mmHg retrograde pressure to close the valve. A roller pump (Cobe 043605-000, Cardiovascular Inc., Avada, Colo.) caused flow through the inlet of the valve to open the leaflets at a specified frequency. The pump rollers only partially displaced the tubing, allowing retrograde flow to close the valve whenever the rollers were not inducing full forward flow. Any overflow out of the tube above the valve was channeled into a reservoir which had the same elevation as the valve. The reservoir then fed back into the roller pump.

While a venous valve is expected to cycle at approximately 0.67 Hz in an individual when walking, an accelerated fatigue test is desirable to reduce the time required to perform the test [64]. As increasing the cycling frequency of polymers can reduce their elastic modulus and lead to early cycle failure, two accelerated fatigue frequencies were used in this test, 3 Hz and 6 Hz [116].

The time average reflux flow rate of each valve at 30 and 160 mmHg was measured before and after undergoing 500,000 cycles. The protocol for the competency test was followed with the exception of having the valves secured inside transparent 10 mm inner diameter tubing with the connectors mentioned previously instead of PVA tubes. This change was made to allow the valves to be visually inspected during cycling to confirm that they were fully opening and closing.

Results

Two valves without any visible defects were selected for the fatigue test. Their time average reflux flow rates at 30 and 160 mmHg were measured (see Table 6). The first valve was placed in the fatigue flow loop and cycled at 6 Hz for 500,000 cycles. After 500,000 cycles the valve was removed from the flow loop and inspected for defects. A crack had formed at the base of one leaflet slit which had propagated down the entire length of the leaflet. Reflux testing of this valve revealed that it was no longer competent, having a reflux flow rate greater than 3 mL/min under 30 and 160 mmHg of retrograde pressure (see Table 6).

The cycling frequency was halved for the second valve, which was fatigued at 3 Hz for 500,000 cycles. After 500,000 cycles the valve was removed from the flow loop and no visible fatigue damage was present. Reflux testing showed that this valve was still competent, having a reflux flow rate less than 3 mL/min at 30 and 160 mmHg pressure heads (see Table 6).

The difference in outcome between the two valves is likely due to the difference in fatigue frequencies. Hysteretic heating from the elevated cycle speed of the valve fatigued at 6 Hz likely reduced the elastic modulus of the PVA and led it to fail at fewer cycles than if cycled at the rate of the valve in actual use, approximately 0.67 Hz [62, 116]. This also suggests that the valve that underwent accelerated fatigue testing at 3 Hz would have remained competent for more than 500,000 cycles if cycled at the rate of the valve in actual use. While it is encouraging that the valve cycled at 3 Hz remained competent after 500,000 cycles, more extensive fatigue testing is required to determine if this valve design remains competent for the expected 9 million cycles in a patient.

TABLE 6

Time average reflux flow rates for valves
before and after 500,000 cycles.

| Valve (Cycle Speed) | Pressure | Time Average Reflux Flow Rate (mL/min) ± stdev | | Change (mL/min) |
| --- | --- | --- | --- | --- |
| | | 0 Cycles | 500,000 Cycles | |
| A (6 Hz) | 30 mmHg | 0.73 ± 0.41 | 4.61 ± 1.32 | 3.88 |
| | 160 mmHg | 0.40 ± 0.65 | 32.17 ± 7.06 | 31.77 |
| B (3 Hz) | 30 mmHg | 0.01 ± 0.01 | 0.03 ± 0.06 | 0.02 |
| | 160 mmHg | 0.08 ± 0.14 | 0.04 ± 0.05 | −0.04 |

Closing Time
Methods

To determine the average closing time of the invention valve, it was placed in a pulsatile flow loop and video recorded. The valve was constrained in the loop by a tubing connector placed inside of its base just below the shoulder. A column of water above the valve provided 40 mmHg of pressure to close it, as measured by a pressure transducer proximal to the valve's shoulder. A roller pump (Cobe 043605-000, Cardiovascular Inc., Avada, Colo.) induced forward flow which caused the valve to open at a rate of 3 Hz. A video recording was taken of the valve cycling open and closed at a speed of 30 frames per second, a resolution of 0.033 seconds per frame. The video recording was then reviewed frame by frame. The number of frames the valve took to close was recorded and converted into a closing time. The mean closing time for an individual valve was found by averaging the closing time for three different cycles. To meet the design requirement of closing in less than 0.5 seconds a valve would need to close in less than 15 frames.

Results

The average number of frames three valves took to close and the corresponding closure time are recorded in Table 7. Each valve took 2 frames for the leaflets to close which equates to a closing time of 0.067 seconds. This suggests that the invention valve design meets the design requirement of closing in less than 0.5 seconds.

TABLE 7

Valve closure time results for three valves.

| Valve | Number of Frames to Valve Closure ± stdev | Closing Time (s) ± stdev |
| --- | --- | --- |
| A | 2 ± 0 | 0.067 ± 0 |
| B | 2 ± 0 | 0.067 ± 0 |
| C | 2 ± 0 | 0.067 ± 0 |
| Average | 2 ± 0 | 0.067 ± 0 |

Distal Pressure Rise Test
Methods

A test was developed to determine the distal pressure rise of the invention prosthetic valve after a simulated calf flexion. Both ends of a PVA tube with a valve glued inside were tied to 9 mm inner diameter Tygon tubing. A pressure transducer was located distal to the valve. Reservoirs were connected to the Tygon tubing upstream and downstream of the valve. The reservoirs were filled with the 40 wt % glycerol solution and elevated 120 cm above the valve to create an equilibrium pressure of 95 mmHg, which is a typical venous equilibrium pressure near the calf [2]. The pressure transducer was calibrated to read 95 mmHg when the system was in equilibrium.

The ejection of blood out of the calf by contraction of the calf muscle was simulated by lowering the reservoir connected to the proximal end of the valve until the pressure transducer read 0 mmHg. This reservoir was then quickly raised back to its original height. The reading on the pressure transducer was recorded after 30 seconds. As the results of this test are highly dependent on the diameter of the tubing used, the valve was tested in tubing slightly smaller than the femoral vein to determine the worst case scenario results.

Results

The distal pressure rise test was performed with and without a valve present. 30 seconds after the simulated ankle flexion, the system without a valve present had returned to the equilibrium pressure of 95 mmHg. This showed that the system could mimic the quick rise in distal pressure seen in individuals with incompetent valves.

The invention valve was then tested in this system three times. The average distal pressure rise 30 seconds after the simulated ankle flexion was 7±1 mmHg, which was approximately 7% of the equilibrium pressure, which satisfies the specification of rising 10% or less.

Outflow Resistance
Methods

Figure 18:
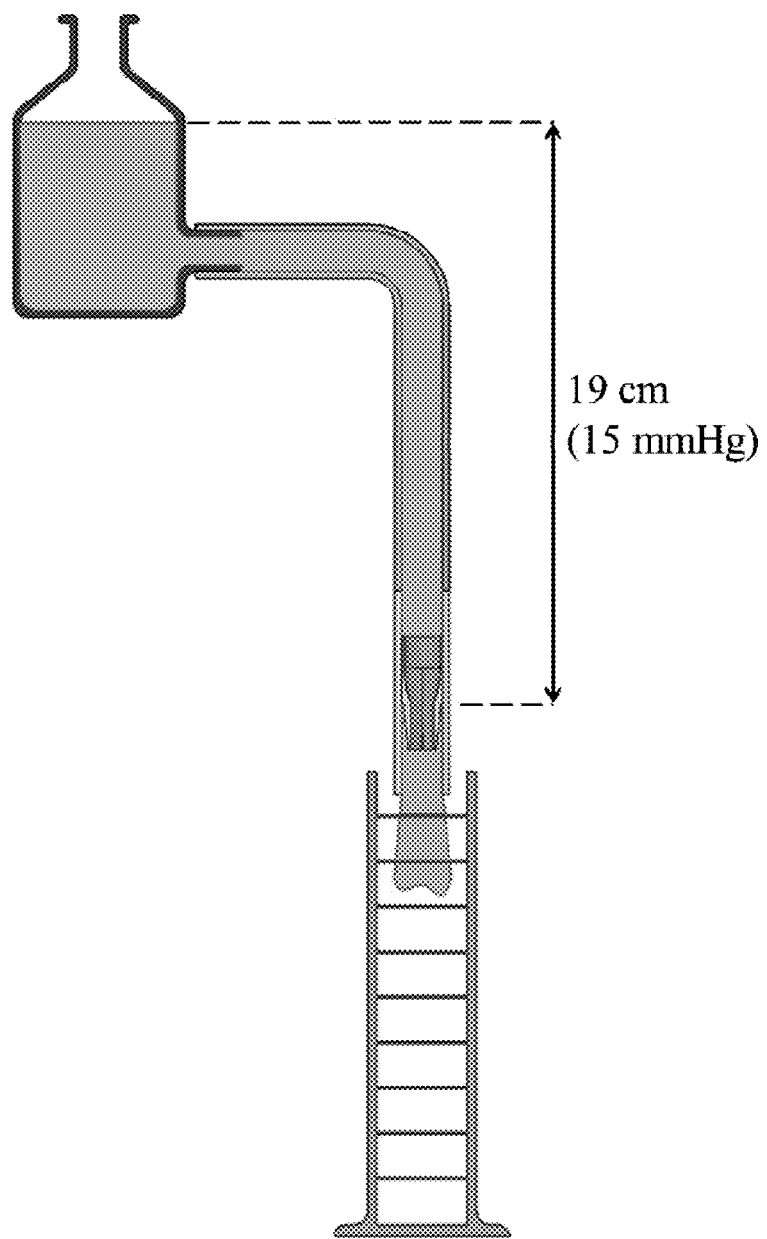
FIG. 18. Schematic of outflow resistance test. A 15 mmHg pressure head is induced by a column of glycerol solution 19 cm above the valve's shoulder. Flow rate is measured visually using a graduated cylinder and a stopwatch.

A test was created to measure a valve's outflow resistance (see FIG. 18). The distal end of a PVA tube with a valve glued inside was tied to 9 mm inner diameter tubing. The tubing was connected to a reservoir filled with 40% glycerol which was quickly elevated 19 cm above the valve's shoulder to create a forward pressure gradient of 15 mmHg. A stopwatch and a graduated cylinder were used to measure the average forward flow rate through the valve. The amount of fluid dispelled through the valve into the graduated cylinder was determined visually, as the 2 second response time of a scale was too slow to provide an accurate measurement.

The total outflow resistance was calculated by dividing the pressure gradient by the measured flow rate. This test was performed without a valve to determine the resistance inherent in the system. The resistance added by the valve was calculated by subtracting the resistance inherent in the system from the total outflow resistance.

Results

Figure 19:
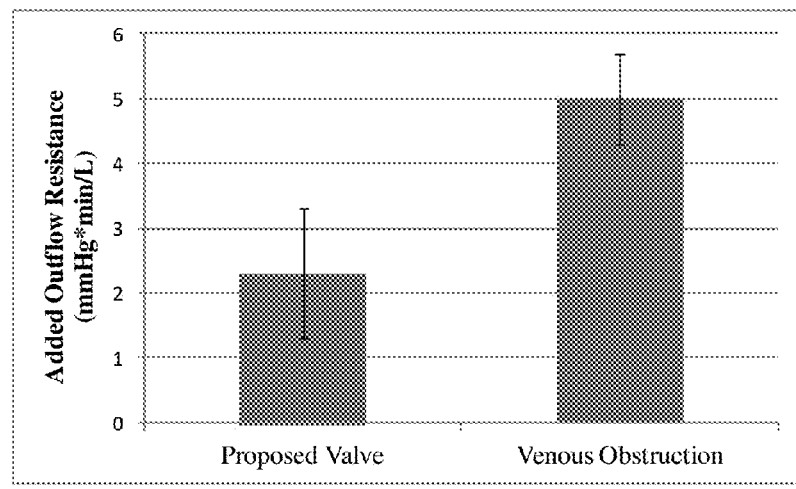
FIG. 19. Comparison of outflow resistance added by the valve and venous obstruction Grade 1 at 15 mmHg (obstruction data from [27]).

The measured flow rates, total outflow resistances, and resistance added by the valves were found for five individual valves and are shown in Table 8. The outflow resistance inherent in the system was 9.1 mmHg*min/L, which is similar to the resistance of a healthy vein at this pressure gradient, 10 mmHg*min/L [27]. The average resistance added by the valves was 2.3±1.0 mmHg*min/L. This suggests that the valve will not significantly impede blood flow back to the heart and that it meets the design specification of increasing the outflow resistance by less than 5 mmHg*min/L (see FIG. 19).

TABLE 8

Measured average flow rates, total outflow resistances,
and resistance added by the valves results.

| | Average Flow Rate (mL/min) ± stdev | Total Outflow Resistance (mmHg*min/L) ± stdev | Outflow Resistance Added by Valve (mmHg*min/L) ± stdev |
| --- | --- | --- | --- |
| No Valve | 1651 ± 76 | 9.1 ± 0.42 | NA |
| A | 1161 ± 65 | 13.0 ± 0.7 | 3.9 ± 0.7 |
| B | 1426 ± 37 | 10.5 ± 0.3 | 1.4 ± 0.3 |
| C | 1417 ± 53 | 10.6 ± 0.4 | 1.5 ± 0.4 |

TABLE 8-continued

Measured average flow rates, total outflow resistances, and resistance added by the valves results.

| | Average Flow Rate (mL/min) ± stdev | Total Outflow Resistance (mmHg*min/L) ± stdev | Outflow Resistance Added by Valve (mmHg*min/L) ± stdev |
|---|---|---|---|
| D | 1333 ± 46 | 11.3 ± 0.4 | 2.2 ± 0.4 |
| E | 1281 ± 66 | 11.7 ± 0.6 | 2.6 ± 0.6 |
| Average | 1323 ± 109 | 11.4 ± 1.0 | 2.3 ± 1.0 |

Washout Test
Methods

A closed flow loop was created to determine if all of the fluid behind the valve's leaflets washes out under a flow rate of 400 mL/min. The invention valve was placed on a connector and fixed inside a transparent tube with a 10 mm tube similar to the fatigue test. This segment of tubing was then connected to the rest of the flow loop. The loop was then filled with a 40% glycerol solution. To visualize the flow of the fluid behind the valve's leaflets, a green hydrophilic dye, McCormick Green Food Color (McCormick & Company, Sparks, Md.), was injected behind the valve's leaflets. A roller pump (Cobe 043605-000, Cardiovascular Inc., Avada, Colo.) caused an average flow rate of 410 mL/min through the inlet of the valve. The pump rollers displaced the tubing enough to prevent any retrograde flow. The fluid then flowed into a closed reservoir, which fed back into the roller pump. If the dye is completely washed out from behind the leaflets then the valve is considered to have passed this test.

Results

The dye washed out from behind the leaflets in a few seconds when the roller pump was turned on. This suggests that flow behind the valve leaflets does not become stagnant under the low flow rate encountered in the supine position.

Buckling Test
Methods 25 mm long rigid tubes comprised of FullCure®720 were created using an Objet Eden250™ 3D printer (Stratasys Ltd., Edina, Minn.) with inner diameters ranging from 6.5 to 10.0 mm in increments of 0.5 mm. These tubes were used to determine the smallest diameter a valve could be inserted into without radially buckling for a prototype valve without a stent. The valve was inserted into a tube and then expanded with a 10 mm balloon. The balloon was then removed and the base of the valve was visually inspected for radial buckling. The largest diameter at which the valve buckled was recorded and the diameter 0.5 mm larger was assumed to be the smallest diameter a valve could be in without buckling.

Result

A prototype valve without a stent was able to decrease in diameter from 9 to 7 mm (22%) without radially buckling. 7 mm was the smallest diameter the valve could be inserted into without buckling as it radially buckled in a 6.5 mm tube. This is 1.5 mm smaller than the 8.5 mm required by the specification. A 10 mm Midha valve was found to radially buckle in a 9.5 mm tube, so it would not have met this specification.

Blood Flow Loop Test
Methods

A blood flow loop similar to that used by Midha was erected [66]. A stented valve was placed inside a section of 10 mm inner diameter transparent tubing. A 10 mm balloon was inflated to expand the stent to fit the tubing. Clamps constrained this section of tubing to ensure that the valve was oriented horizontally. Whole porcine blood was heparinized (3.5 mL/L) and put into the flow loop. A roller pump (Cobe 043605-000, Cardiovascular Inc., Avada, Colo.) caused the blood to flow through the inlet of the valve at an average of 510 mL/min. The blood then dispensed into an open reservoir which fed into the roller pump. Blood flowed through the loop for three hours. At this point the section of tubing containing the valve was removed and inspected for clots. The cessation of flow from the tubing into the reservoir indicates that a clot had formed in the flow loop and would signal that the test should be stopped prematurely.

Results

A stented valve was placed in the blood flow loop for three hours. The section of tubing containing the valve was removed and lightly rinsed with water to drain it of blood. No clots were present inside the valve or behind its leaflets. Small clots were beginning to form around the tubing connectors, demonstrating that clot formation was possible in this system with the porcine blood used. This test demonstrated the short term patency of the invention valve to be at least equivalent to the Midha valve and meets the design specification.

Deliverability
Methods

The minimum catheter size a valve can fit in can be estimated as follows. If a prosthetic valve is crimped and perfectly fits into a cylindrical catheter without any gaps or lengthening of the valve, the volume of the valve in terms of its crimped radius and length would be:

$$V = \pi r^2 L \tag{8}$$

Where V is the volume of the valve in mm$^3$, r is the crimped radius of the valve, and L is the length of the valve. The relationship between French size and the internal radius of a catheter in mm is:

$$F = 3*(2r) \tag{9}$$

Where F is the French size of the catheter and r is the radius of a catheter in mm. Equation (9) can be manipulated to find the radius in terms of French gauges:

$$r = \frac{F}{6} \tag{10}$$

As the radius of the catheter is the same as the crimped radius of the valve, Equation (10) can be substituted into Equation (8) to obtain:

$$V = \pi \left(\frac{F}{6}\right)^2 L \tag{11}$$

Equation (11) can be rearranged to find the French size in terms of the volume and length of the valve:

$$F = 6\sqrt{\frac{V}{\pi L}} \tag{12}$$

Equation (12) can be used to estimate the minimum French size of a catheter that a valve can be placed into. As the direct calculation likely includes a fractional part, a more realistic estimate would be the result rounded up to the next whole number.

To verify that the valve meets the specification of fitting inside of a 16 Fr (5.3 mm) catheter, a 25 mm long rigid tube made of FullCure®720 was created using an Objet Eden250™ 3D printer (Stratasys Ltd., Edina, Minn.) with an inner diameter of 5.3 mm. A valve could then be placed inside this tube to verify that it can fit inside a 16 Fr catheter.

Results

The CAD model of the invention valve was analyzed and its volume and length were found to be 438 mm$^3$ and 25 mm, respectively. The minimum French size the valve could fit into was calculated using Equation (12) to be 14.2, making 15 Fr its actual estimate when rounded up to the next whole number. A prototype valve was placed inside the 16 Fr tube to verify that it meets the specification.

Summary

Table 9 summarizes the design specifications and the results of the verification testing that was performed. The valve of the invention met every design requirement for which verification testing was performed.

thrombus formation, neointimal hyperplasia, fibrous encapsulation, and inflammation developing within 12 weeks [12, 33, 37-41, 43-44, 47, 51, 53-55, 58, 66]. In animal studies longer than 12 weeks, complications did not develop or worsen after 12 weeks [41, 53, 56].

The ovine external jugular vein (EJV) is a potential site of implantation to test the invention valve. This vein has an average diameter of 12.0 with a standard deviation of 1.4 mm, which is comparable to the average size of the human femoral vein, 11.84 mm [41, 71]. Valves are naturally present in the sheep EJV and close to prevent peripheral venous hypertension when hydrostatic or central venous pressure increases [118]. Thus a prosthetic venous valve placed in this location is expected to periodically cycle, such as when the sheep drops its head below its heart while eating.

Methods

A study was designed to evaluate the patency, fixation, and biocompatibility of the invention prosthetic venous valve in the external jugular veins (EJV) of sheep. In studies where replacement valves remained patent for 12 weeks,

TABLE 9

Summary of design specifications and verification testing results for the proposed venous valve.

| | Metric | Units | Specification | Valve Performance* |
|---|---|---|---|---|
| 1 | Reflux rate under a 30 mmHg pressure head | mL/min | ≤8 | 0.44 ± 0.26 |
| 2 | Reflux rate under a 160 mmHg pressure head | mL/min | ≤8 | 0.30 ± 0.27 |
| 3 | Smallest diameter in which the valve remains competent | mm | ≤8.5 | 8$^Ψ$ |
| 4 | Reflux rate under a 30 mmHg pressure head after 500,000 cycles | mL/min | ≤8 | 0.03 ± 0.06$^Ψ$ |
| 5 | Reflux rate under a 160 mmHg pressure head after 500,000 cycles | mL/min | ≤8 | 0.04 ± 0.05$^Ψ$ |
| 6 | Leaflet closing time | s | <0.5 | 0.067 ± 0 |
| 7 | Distal pressure rise 30 seconds after a simulated calf flexion | % | ≤10 | 7 ± 1 |
| 8 | Outflow resistance added by the valve under a 15 mmHg pressure head | mmHg*min/L | <5 | 2.3 ± 1.0 |
| 9 | Fluid behind leaflets washes out under 400 mL/min | Binary | 1 | 1$^Ψ$ |
| 10 | Smallest diameter in which a valve does not buckle | mm | ≤8.5 | 6.5$^Ψ$ |
| 11 | Maximum shear rate on the valve walls with an inlet flow rate of 1600 mL/min | s$^{-1}$ | <3500 | 2300 |
| 12 | Material does not elicit inflammatory response or foreign body reaction when placed in the bloodstream | Binary | 1 | 1 |
| 13 | Material passes biocompatibility tests specified by ISO and USFDA | Binary | 1 | 1 |
| 14 | Material is less thrombogenic than Dacron | Binary | 1 | 1 |
| 15 | Time to occlusion when running heparinized (3.5 mL/L) porcine blood in a flow loop | Hours | >3 | >3$^Ψ$ |
| 16 | Minimum catheter size the valve can fit in | Fr | ≤16 | 16 |
| 17 | Ratio of the valve length that contacts the vein wall to the vein diameter | NA | ≥1.5 | 1.5 |

*Mean ± Standard Deviation
$^Ψ$N = 1

Example 5

Validation Testing and Sizing

Purposes

While verification testing confirmed that the proposed valve met all the design specifications for an effective prosthetic venous valve, validation testing is needed to confirm that the valve meets the needs of the user with its intended use [117].

Animal Testing

The long term safety, patency, and relative thrombogenicity of the invention valve in a human can be inferred by testing it in an animal model. Replacement venous valves have historically been tested in sheep, pigs, dogs, and goats with complications, if occurring, such as valve migration, 9-16 sheep were used [47, 56]. For this study to be comparable to these studies, 12 sheep were used to account for potential biologic variance.

Each sheep has two valves surgically implanted, one in each EJV. Each sheep is anesthetized prior to surgery. To implant the valves, approximately 2 inches of each EJV are exposed by a longitudinal incision. A stented valve is inserted into each vein through a small venotomy and expanded by a balloon until fixed in position. Each venotomy and longitudinal incision are closed with sutures. Each sheep then recovers from the anesthesia and is given local analgesics to minimize pain and discomfort.

To decrease the risk of thrombosis during and after surgery, the following regiment of anticoagulation is given to each sheep. During manufacturing valves are impregnated with less than 5 mL of 3.2% sodium citrate which is slowly expelled after implantation. During surgery, each sheep receives 100 U/kg of heparin. After surgery, 325 mg of buffered aspirin is daily administered to each sheep.

Valve patency and position, and biocompatibility are the primary endpoints of the study. The study lasts for a maximum of 12 weeks. The position of and flow through each valve are evaluated every two weeks by venogram, as described by Midha [66]. The sheep is anesthetized during each venogram. Sheep is euthanized after 12 weeks or when both of its implanted valves are no longer patent. The valve is deemed biocompatible if inflammation or fibrin encapsulation does not occur. Each sheep is observed daily for any signs of discomfort or abnormal behavior. If a sheep loses more than 20% of its baseline weight prior to surgery it is euthanized to prevent unnecessary distress.

After a sheep is sacrificed, the vein segments containing the implanted valves are removed. Each segment is gently washed with saline to decrease the risk of post-mortem clotting and placed in formalin for preservation. The valves are examined by gross sectioning and histology performed as described by Midha [66].

Protocol 2002062-102415BA, which details the above procedures, was approved by the Institutional Animal Care and Use Committee of Emory University on Oct. 24, 2012.

Human Testing

If the invention valve meets the primary endpoints of animal testing, the valve is then ready for human testing. The following describes the protocol to implant and evaluate the valve in human subjects.

Location

Minimum Distance Between Valves

The minimum distance between two prosthetic valves placed in the same vein segment is determined by the minimum pressure needed to close an individual valve. The invention valve is flutter open and closed when a low level of backpressure is applied, resulting in a pulsing sensation. As flow pulsation in the saphenous vein has been correlated with increased symptom severity in individuals with CVI, leaflet fluttering is avoided [119].

The average minimum closing pressure of the invention valve was found by visually measuring the minimum height of water needed to close the valve and calculating the applied hydrostatic pressure. Three valves each underwent this procedure three times and the mean and standard deviation for the minimum water height and corresponding hydrostatic pressure required to close each valve is shown in Table 10. The mean minimum closing pressure for three valves was approximately 10 mmHg, which would occur under a column of blood (density=1056 kg/m$^3$) 13 cm high [113]. This suggests that valves of this design should be implanted at least 13 cm apart.

Potential Vein Segments and Implantation Sites

Labropoulos recorded the number of refluxing segments in the deep veins for 94 patients with venous ulcers (see Table 11) [25]. Reflux in the Popliteal vein accounted for the largest percentage of refluxing segments (42%), followed by the CFV (29%), calf veins (17%), and the femoral vein (12%). The deep veins in the calf are approximately 2-3 mm in diameter and are much smaller than the other deep veins which are roughly 9-14 mm in diameter [129]. To reduce the number of different valve sizes to be produced and keep manufacturing costs low, the CFV, femoral, and popliteal veins are the sites of implantation for the invention prosthetic valve. Valves that fit in these three veins are able to correct 83% of the refluxing deep venous segments for individuals with venous ulcers.

In the surgical correction of deep venous valves, usually only one incompetent valve is corrected with sites of repair being the most proximal valve in the CFV, femoral, or popliteal vein [130-131, 34, 132-135]. While the majority of valve repairs have been in the CFV, surgical correction of the popliteal vein is becoming more popular among surgeons [74]. However, Tripathi found a statistically significant increase in ulcer healing rate when the surgical correction of deep venous valves was performed in multiple venous segments compared to singular valve repair, irrespective of the site of valve repair (see Table 12) [26]. This suggests that reflux should be corrected in each refluxing vein segment to achieve the greatest symptom improvement. However, it may be prudent to implant valves only in the CFV for the initial clinical trial to avoid the development of significant complications in the event of valve occlusion. If validation testing shows that the invention valve is unlikely to clot in the CFV, valves may also be placed in incompetent femoral and popliteal veins.

A functioning valve in the most proximal end of an incompetent vein would likely restore competence to a greater portion of the vein than when placed in a more distal location. Native valves are typically located 0.5-2 cm distal to junctions with other veins and periodically in between [120]. Assuming validation testing shows that the invention valve is unlikely to clot in the CFV, it is suggested that the replacement valve be placed 0.5-2 cm below the most proximal end of each refluxing CFV, femoral, and popliteal vein. After the initial valve is placed, Doppler ultrasound may be used to determine if additional valves need to be implanted distal to the initial valve. When reflux greater than 3 mL/min is present during a Valsalva maneuver, additional valves may be placed between vein junctions within the same vein segment with a minimum of 13 mm between valves to ensure that these additional valves can close. Prior to implantation, a specific implantation site for the most proximal valve in each incompetent vein segment should be determined by venogram or ultrasound.

TABLE 10

Experimental results of the minimum height of water required to close a valve. The applied hydrostatic pressure and the height of blood needed to cause this pressure (equivalent to the minimum distance between valves in a vein) were calculated.

| Valve | Minimum Water Height Needed to Close the Valve (cm) (mean ± stdev) | Hydrostatic Pressure (mmHg) (mean ± stdev) | Minimum Distance Between Valves in a vein (cm) |
|---|---|---|---|
| A | 13.7 ± 0.6 | 10.1 ± 0.4 | 13 ± 1 |
| B | 13.3 ± 0.6 | 9.8 ± 0.4 | 13 ± 1 |
| C | 13.3 ± 0.6 | 9.8 ± 0.4 | 13 ± 1 |
| Average | 13.4 | 9.9 | 13 |

TABLE 11

Occurrence of reflux in deep vein segments in ulcerated limbs (data from [42]).

| Vein | Number of Refluxing Segments | Percent |
|---|---|---|
| CFV | 26 | 29 |
| Femoral | 11 | 12 |
| Popliteal | 37 | 42 |
| Calf Veins | 15 | 17 |

TABLE 12

Comparison of ulcer healing rates for the surgical correction of single and multiple deep venous valves with primary and secondary incompetence (data from [45]).

| Incompetence Type | % Ulcer Healing | | |
|---|---|---|---|
| | Single valve repaired | Valves repaired in 2-3 incompetent venous segments | Change |
| Primary | 57 | 72.9 | 15.9 |
| Secondary | 46 | 54.7 | 8.7 |

Methods
Sample Size

As the data to be analyzed is paired and is not normal, the Wilcoxon signed-rank statistic for paired data may be used to determine statistical significance compared to baseline values [121-122]. This statistic is commonly used to determine significance in VCS scores and hemodynamic parameters [24, 28].

G*Power was used to determine the sample size with the following inputs [123-124]: The significance level, also referred to as the type 1 error alpha, was set to 0.05. As the VCS score changes in discrete increments of 1, the effect size to be discerned in the test was set to 1. The desired power of the test is 0.95. With the aforementioned criteria, the suggested sample size is 15 subjects. As there is a risk of losing contact with some subjects, the actual number of subjects recruited for the study may be more than 15 to ensure that enough subjects remain in contact for statistical significance to be determined.

Inclusion Criteria

Subjects selected for the study are having a severe case of CVI that is resistant to conservative treatment, specifically compression stockings, with a VCS score of 7 or higher. Each has the presence of deep venous reflux, with reflux lasting more than 2 seconds in the CFV and have a VFI 10 mL/s or greater.

Exclusion Criteria

Potential subjects are excluded based on the following criteria: The presence of venous obstruction of any grade level, as manifested by an outflow resistance 15 mmHg*min/L or greater, as venous stenting is a more appropriate procedure [27]. Occurrence of thrombosis in the last 24 months, as this would increase the likelihood of thrombosis occurring in the valve clotting. Individuals with the presence of another disease requiring treatment such as diabetes or another cardiovascular disease. Individuals with a high risk of developing complications from heparin or aspirin.

Implantation

Prior to implantation, subjects are having their VCS score, VFI, AVP, EF, and outflow resistance measured. Prior to the procedure, the diameter of the CFV where the valve is implanted may be measured using Doppler ultrasound. The guidelines regarding valve sizing are followed to determine the size of valves to be implanted. Patients are given local anesthesia and 5000 units of heparin in preparation for the procedure [32]. Guided by ultrasound, the valve is percutaneously delivered by catheter 0.5-2 cm below the most proximal end of the CFV and expanded with a balloon. Additional valves are implanted in the CFV at least 13 cm apart at locations where Doppler ultrasound reveals reflux to exceed 3 mL/min when patients perform a Valsalva maneuver. Patients take 81 mg of Aspirin daily indefinitely after implantation to reduce the risk of thrombus formation [32].

Endpoints

Primary endpoints to evaluate the safety and functionality of the invention valve after being implanted in a human are as follows:

valve patency, which is determined by Doppler ultrasound in the supine position. A few prosthetic venous valves implanted into humans have been reported, with most failing to demonstrate long term competency and patency [40, 42, 50, 52]. Of these valves, the longest reported to remain competent and patent was 16 months, which serves as a benchmark for other prosthetic venous valves [52].

valve competency, which is determined by Doppler ultrasound during a Valsalva maneuver with the subject in the 15% reverse Trendelenburg position. Valves taking longer than 0.5 seconds to close are typically deemed incompetent in clinical practice, thus the valve is deemed competent if it closes in less than 0.5 seconds [17-21]. The benchmark for competency is 16 months [52].

valve position, as determined by ultrasound. A valve that is not fixed in position after implantation has the risk of migrating to the lungs.

valve biocompatibility, as determined by the absence of inflammation or fibrin encapsulation.

Secondary endpoints to evaluate the valve's impact on a subject's symptoms and vein hemodynamics, and to allow comparison to other treatments of CVI are as follows:

VCS score, which quantifies the change in severity of a subject's symptoms and allow comparison with other treatments for CVI. For example, Cesarone reported the average VCS score in 31 individuals with CVI to decrease from 8.4 to 5.7 after eight weeks when treated with compression therapy [29]. As VCS scores are discrete, the invention valve is as effective for treating CVI as compression stockings if the average VCS score in the human study is 6 or less after 8 weeks.

AVP, which is determined by needle in the dorsal foot vein during tiptoe exercises with the methods used by Nicolaides [13]. This quantifies any changes in a subject's venous hypertension, which is the primary characteristic of individuals with CVI.

VFI, which is measured by PG with the methods used by Araki [22]. This quantifies the effectiveness of the proposed valve to reduce venous reflux.

EF, which is determined by PG with the methods used by Araki [22]. This determines if the valve influences the effectiveness of the calf muscle pump, which is one of the main contributing factors to venous hypertension in CVI.

Outflow resistance, which may be determined by PG and a needle in the dorsal foot vein with the methods used by Neglen [27]. This will detect if an outflow obstruction, another contributor to the venous hypertension seen in individuals with CVI, has developed in a subject. An outflow resistance above 15 mmHg*min/L would indicate that something, such as the valve or DVT, has obstructed venous outflow and that additional corrective procedures, such as venous stenting, may need to be proscribed.

Primary and secondary endpoints are measured at baseline, 8 weeks, as well as 6, 12, and 18 months after implantation.

Valve Sizing
Determining Vein Diameter for Sizing

To determine the range of vein sizes in which the invention valve can fit, a baseline reference for the vein diameter must first be defined because veins are distensible. Sizing the valve in terms of a vein's fully distended diameter is advantageous so that fixation by stent expansion can be ensured. In the following descriptions, D* refers to the fully distended diameter of the vein.

Minimum Vein Diameter

The smallest diameter in which a valve can remain competent determines the minimum diameter, $D^*_{min}$, it can be implanted into. The distensibility of a vain, $\alpha$, can be quantified by dividing a vein's $D^*$ by the diameter of the vein at rest, $D_{rest}$:

$$\alpha = \frac{D^*}{D_{rest}} \tag{13}$$

The $D^*_{min}$ a valve can be placed in is $$D^*_{min} = \alpha * SCD \tag{14}$$

Where SCD is the smallest diameter in which the valve can remain competent. The SCD of the 9 mm valve design that underwent verification testing was 8 mm. Assuming the ratio of valve diameter to SCD remains constant when the valve is scaled in size, Equation (14) can be stated in terms of the original outer diameter of the valve, $V_{Di}$:

$$D^*_{min} = 0.9\alpha V_{Di} \tag{15}$$

Equation (15) can be used to find the smallest $D^*$ in which a valve can be placed and remain competent and is a function of the vein's distensibility and the initial diameter of the valve.

Maximum Diameter

The largest diameter in which a valve can remain competent without tearing during stent expansion determines the maximum vein diameter, $D^*_{max}$, it can be placed in. Weaver defined the stretch ratio of a circular test section as [97]:

$$\lambda = \frac{C_f}{C_i} \tag{16}$$

Where $C_f$ is the final circumference of the test section and $C_i$ is its initial circumference. Equation (16) can be rewritten as:

$$\lambda = \left(\frac{D_f}{D_i}\right)^2 \tag{17}$$

Where $D_f$ is the final diameter of the circular test section and $D_i$ is its initial diameter. Solving Equation (17) for the final diameter yields:

$$D_f = D_i\sqrt{\lambda} \tag{18}$$

For the present application, $D_f$ would be equal to $D^*_{max}$, $D_i$ the valve's unexpanded diameter $V_{Di}$, and $\lambda$ the allowable stretch ratio. Weaver determined that a cylindrical 20 wt % PVA section opened at a slow rate fails at an average stretch ratio of 3.08 [97]. Dividing by a safety factor of 1.25 yields a safe stretch ratio of 2.46. It is assumed that a stented valve needs to be capable of expanding to a diameter at least 15% larger than the vein it is inserted into to be fixed in place [31]. These constraints can be imposed on Equation (18):

$$1.15 D^*_{max} = V_{Di}\sqrt{2.46} \tag{19}$$

Solving for $D^*_{max}$, Equation (19) becomes:

$$D^*_{max} = 1.4 V_{Di} \tag{20}$$

Equation (20) is only a function of the initial diameter of the valve and can be used to find the largest $D^*$ a valve can be placed into and remain fixed in position with low risk of tearing.

The risk of leaflet prolapse increases the larger the valve expands. An experimental test was performed to ensure that the leaflets of a valve do not prolapse when expanded to 1.4 times its initial diameter. Using Equation (20), $D^*_{max}$ for a 9 mm valve was calculated to be 12.6 mm. A stented 9 mm valve was then expanded inside a 13 mm tube, the nearest available sized tubing larger than its $D^*_{max}$. A pressure head of 160 mmHg was applied proximal to the valve with a column of water 220 cm above the valve's shoulder. The leaflets closed without prolapsing. This suggests that $D^*_{max}$ is limited more by the risk of tearing than by prolapse for this valve design and that the leaflets do not prolapse if Equation (20) is followed.

Stent Size

It is assumed that a stented valve needs to be capable of expanding to a diameter at least 15% larger than the vein it is inserted into to be fixed in place [31]. Thus the fully expanded diameter of a valve's stent, $D_{stent}$, needs to be 15% larger than the valve's $D^*_{max}$, which can be found by modifying Equation (20):

$$D_{stent} = 1.15 * 1.4 V_{Di} \tag{21}$$

Which simplifies to:

$$D_{stent} = 1.6 V_{Di} \tag{22}$$

Valve Sizing for Sheep

Bia measured the mean cross sectional area of the sheep EJV to increase by 2%, which corresponds to a diameter change of less than 1%, as the internal pressure increased from 75 to 130 mmHg [125]. This suggests that the distensibility of the sheep EJV can be neglected. Thus $D^*$ for a sheep EJV is the diameter of the pressurized vein at rest which can be measured, such as by venogram, prior to implantation.

The mean sheep EJV diameter is 12.0 mm and has a standard deviation of 1.4 mm [41] Assuming the diameters of this vein have a normal distribution, 95.5% of these veins are within two standard deviations of the mean, 9.2-14.8 mm. The smallest sheep EJV diameter, $D^*_{min,sheep}$, in which a valve can remain competent can be found by substituting $\alpha=1$, which corresponds to a non-distensible vein, into Equation (15):

$$D^*_{min,sheep} = 0.9 V_{Di} \tag{23}$$

Equation (20) regulates the largest sheep EJV diameter, $D^*_{max,sheep}$, a valve can be safely placed in.

A single valve size which is capable of fitting into most sheep EJV diameters is desirable to reduce the number of stents to be acquired and valves to be manufactured. A valve which can fit in the highest percentage of sheep EJV diameters has its minimum and maximum $D^*$ be the same distance away from the mean:

$$12.0 \text{ mm} - D^*_{min,sheep} = D^*_{max,sheep} - 12.0 \text{ mm} \tag{24}$$

Substituting Equations (20) and (23) into Equation (24) yields:

$$12.0 \text{ mm} - 0.9 V_{Di} = 1.4 V_{Di} - 12.0 \text{ mm}$$

Solving for $V_{Di}$:

$$V_{Di} = 10.4 \text{ mm}$$

Figure 20:
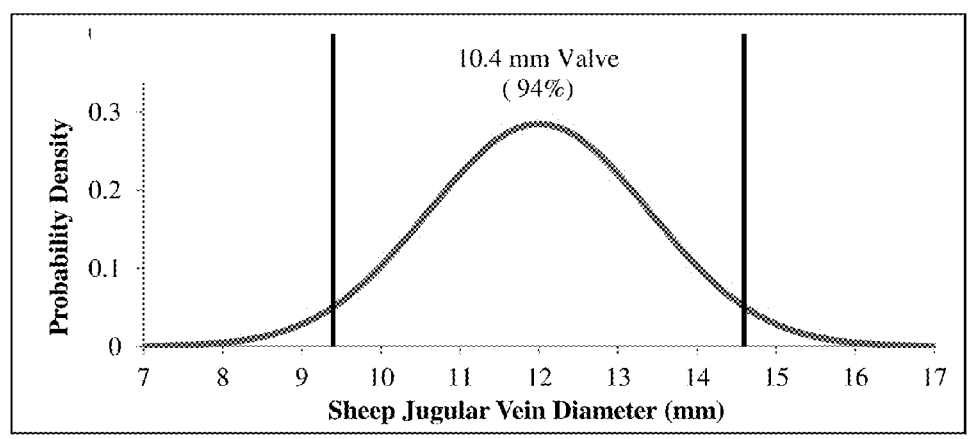
FIG. 20. Probability density, assuming normality, of the sheep jugular vein diameter. A 10.4 mm diameter valve would fit into diameters ranging from 9.4 to 14.6 mm, which covers 94% of the expected diameter sizes.

This suggests that a valve with the design specifications scaled to have an outer diameter of 10.4 mm would fit the highest percentage of sheep EJV diameters. Equations (20) and (23) indicate that a 10.4 mm valve would fit into sheep EJVs with diameters ranging from 9.4 to 14.6 mm which accounts for 94% of the expected vein diameters, assuming normality (see FIG. 20). Equation (22) indicates that a stent capable of expanding to 17 mm stent would need to be placed in a 10.4 mm valve.

Valve Sizing for Humans

In humans, the Valsalva maneuver can be used to cause veins to distend, with greater dilation occurring when the individual is inclined in the reverse Trendelenburg position than in the supine position [71, 126-127]. The diameter of a human vein in the 15% reverse Trendelenburg position during a Valsalva maneuver is assumed to be $D^*$, the fully distended diameter of the vein. The vein diameter may be visualized and measured by venogram or ultrasound. The methods used by Fronek are an example of using duplex ultrasound to take this measurement [71].

Fronek measured the mean diameter of the CFV of individuals at rest in the supine position and during a Valsalva maneuver in the 15% reverse Trendelenburg position ($D^*$) [71]. On the average, $D^*$ was 21% larger than the diameter of the vein at rest and had a mean diameter of 14.27 mm with a standard deviation of 2.49 mm [71]. Hertzberg measured the popliteal vein of individuals at rest in the supine position to be 6.8 mm with a standard deviation of 2.11 mm [128]. Assuming that the diameter of the popliteal vein also distends from rest by 21% during a Valsalva maneuver in the 15% reverse Trendelenburg position, the popliteal vein's mean $D^*$ is 8.2 mm. The standard deviation of $D^*$ for the popliteal vein is assumed to remain the same as when resting, 2.11 mm. Assuming a normal distribution, 95.5% of the $D^*$s of the CFV and popliteal veins are within two standard deviations of their means, 9.3-19.3 mm and 4.0-12.4 mm respectively.

The smallest vein diameter, $D^*_{min,human}$, in which a valve can remain competent can be found by substituting $\alpha=1.21$, which corresponds to a 21% distention from rest, into Equation (15):

$$D^*_{min,human}=1.1 V_{Di} \quad (25)$$

Equations (25) and (20) can be used to find the $D^*$ range for a stented valve of the invention design of any scale for a human. From this information, a set of valve sizes can be specified which fit into the CFV, femoral, and popliteal veins of the general population. As the femoral vein is typically smaller than the CFV and larger than the popliteal vein in an individual, it is assumed that a set of valves that fits at least 90% of the CFV and popliteal veins in the general population can also service the femoral veins encountered.

A set of 5 valve sizes is shown in Table 13 which covers 90-96% of the probable range of CFV and popliteal vein diameters of the general population. This set was developed by attempting to satisfy the following criteria:

1) Service at least 90% of both the CFV and the popliteal veins to ensure adequate coverage of the general population.

2) Offer continuous size coverage throughout the entire set to ensure that valves within the set also fit the femoral veins of the general population.

3) Each individual valve size is to service at least 15% of at least one vein type to warrant its production.

4) Have the overlap of two valve $D^*$ ranges occur in multiples of 0.5 mm to make it easier for a surgeon to discern which valve size to use.

Figure 21:
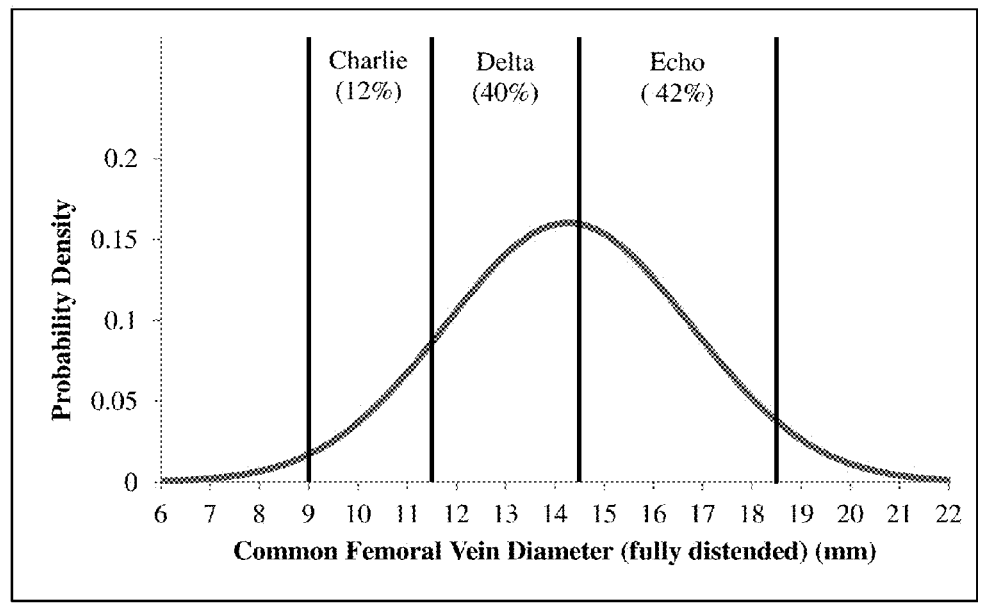
FIG. 21. Probability density, assuming normality, of the CFV's fully distended diameter. The percent probability of a diameter falling in the range of selected valve sizes is indicated.
Figure 22:
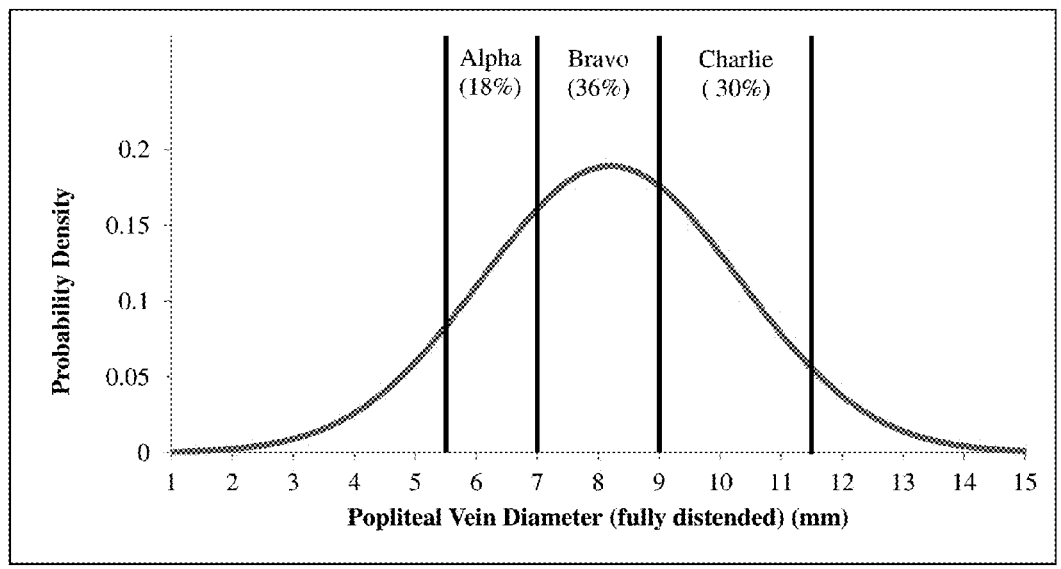
FIG. 22. Probability density, assuming normality, of the popliteal vein's fully distended diameter. The percent probability of a diameter falling in the range of selected valve sizes is indicated.

To simplify the selection process, each valve was named from the NATO phonetic alphabet, with Alpha corresponding to the smallest valve size and Echo the largest valve size (see Table 13). Assuming normality, the probability of each vein's $D^*$ occurring in the range of each valve was calculated using Minitab v 13.2 (Minitab, Inc, State College, Pa.) and is shown in Table 13 and FIGS. 21 and 22. The CFV is primarily serviced by the largest three valves, and the popliteal by the smallest 3 valves (see Table 13 and FIGS. 21 and 22).

A guide for surgeons to select the appropriately sized valve is shown in Table 14. In the event of a measurement for $D^*$ being on the boundary of two valve sizes, it is recommended that the larger valve size be chosen to ensure the correct fixation and to keep the shear rates low. For example, it is recommended that a vein with a $D^*$ of 14.5 mm have the Echo valve placed inside of it. The guide in Table 14 also displays the maximum expanded diameter of the stent to be housed inside each valve, indicating the size of balloon for surgeons to use during insertion. These stent sizes were found using Equation (22).

The flow rate through the popliteal vein is approximately 30% of that through the CFV [136]. While the valves best suited to fit inside the popliteal vein are much smaller than the one analyzed in the CFD simulation described above, an elevated shear rate does not likely occur because of the lower flow rate.

TABLE 13

Suggested set of valve sizes with the calculated minimum and maximum $D^*$ of each.

| Valve Name | Valve Diameter (mm) | Min Diameter* (mm) | Max Diameter* (mm) | % of CFV diameters serviced | % of Popliteal diameters serviced |
|---|---|---|---|---|---|
| Alpha | 5 | 5.5 | 7.0 | 0 | 18 |
| Bravo | 6.4 | 7.0 | 9.0 | 2 | 36 |
| Charlie | 8.2 | 9.0 | 11.5 | 12 | 30 |
| Delta | 10.4 | 11.4 | 14.6 | 40 | 6 |
| Echo | 13.2 | 14.5 | 18.5 | 42 | 0 |
| Entire Set | | 5.5 | 18.5 | 96 | 90 |

TABLE 14

Sizing guide for the suggested valve set.

| Diameter* (mm) | Valve | Fully Expanded Stent Diameter (mm) |
|---|---|---|
| 5.5-7 | Alpha | 8 |
| 7-9 | Bravo | 10 |
| 9-11.5 | Charlie | 13 |
| 11.5-14.5 | Delta | 17 |
| 14.5-18.5 | Echo | 21 |

*Diameter measured by ultrasound during a Valsalva maneuver in the 15% reverse Trendelenburg position. In the event of the diameter falling on the boundary of two valve sizes, the larger size should be selected.

Clinician Procedure

Figure 23:
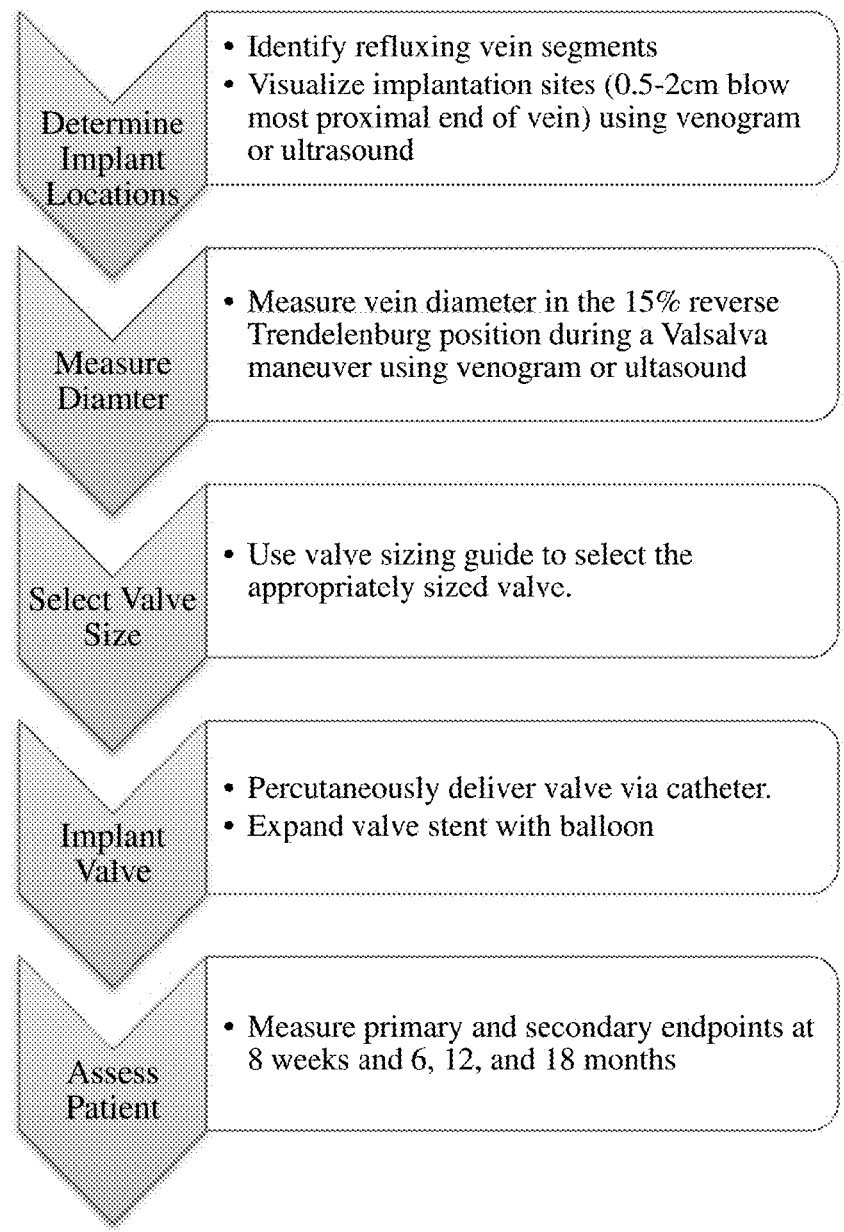
FIG. 23. Flow chart for clinicians for human testing.

A flow chart for the role of clinicians in implantation and evaluation of the invention valve is shown in FIG. 23. Clinicians identify where valves should be implanted by identifying refluxing vein segments and then visualizing implantation sites using venogram or ultrasound. The diameter at the implantation site of each vein is measured in the 15% reverse Trendelenburg position using venogram or ultrasound. Table 14 is used to select the appropriate valve size to be implanted in each location. The valves may then be percutaneously delivered via catheter and the valve's stents are then expanded by balloon. After the procedure the primary endpoints are assessed for each implanted valve, and the secondary endpoints are measured for each limb at 8 weeks and 6, 12, and 18 months.

Example 6

Evaluation and Discussion

Valve Design Evaluation

The invention prosthetic valve met every design specification for an effective prosthetic venous valve. On the average, the valve allows less than 0.5 mL/min of reflux at low and high retrograde pressures even after 500,000 cycles, suggesting that it reduces the reflux of individuals with venous reflux by more than 99.6% [19]. The valve closes in less than 0.07 seconds and allows the distal pressure to rise to an average of 7% of the equilibrium pressure 30 seconds after a simulated ankle flexion. The valve increases the outflow resistance an average of 2.3 mmHg*min/L which is much less than venous obstructions which increase the outflow resistance by at least 5 mmHg*min/L [27]. The valve can fit in a 16 French catheter and is capable of percutaneous delivery. The base of the valve is 1.5 times the diameter of the vein it is to be implanted which will help it to be oriented correctly upon deployment.

Thus far the valve has demonstrated that it has low thrombogenicity. The maximum shear rate in the valve after a Valsalva maneuver is approximately 2300 $s^{-1}$, which puts it at low risk for shear induced thrombosis. Fluid behind the valve's leaflets is ejected with a forward flow rate of 400 mL/min, suggesting that thrombus formation does not occur at this location when an individual is at rest in the supine position. The material of the valve, PVA, has passed the ISO and USFDA biocompatibility tests and has been shown to be less thrombogenic than Dacron in previous testing [65, 85, 95]. PVA is also capable of drug delivery and can elute anticoagulation drugs, such as citrate [66]. A stented valve remained patent in a porcine blood flow loop for 3 hours, demonstrating that its short term patency is at least equivalent to the Midha valve which had previously held the record for the longest occlusion time in such a loop.

Valves of the invention with the design specifications can function and expand into veins with fully distended diameters that are 1.1-1.4 times the valve's initial diameter. With this versatility, a 10.4 mm valve is fit in 94% of sheep EJVs, and a set of 5 valves is fit in 90-96% of the CFV, femoral, and popliteal veins.

Figure 24:
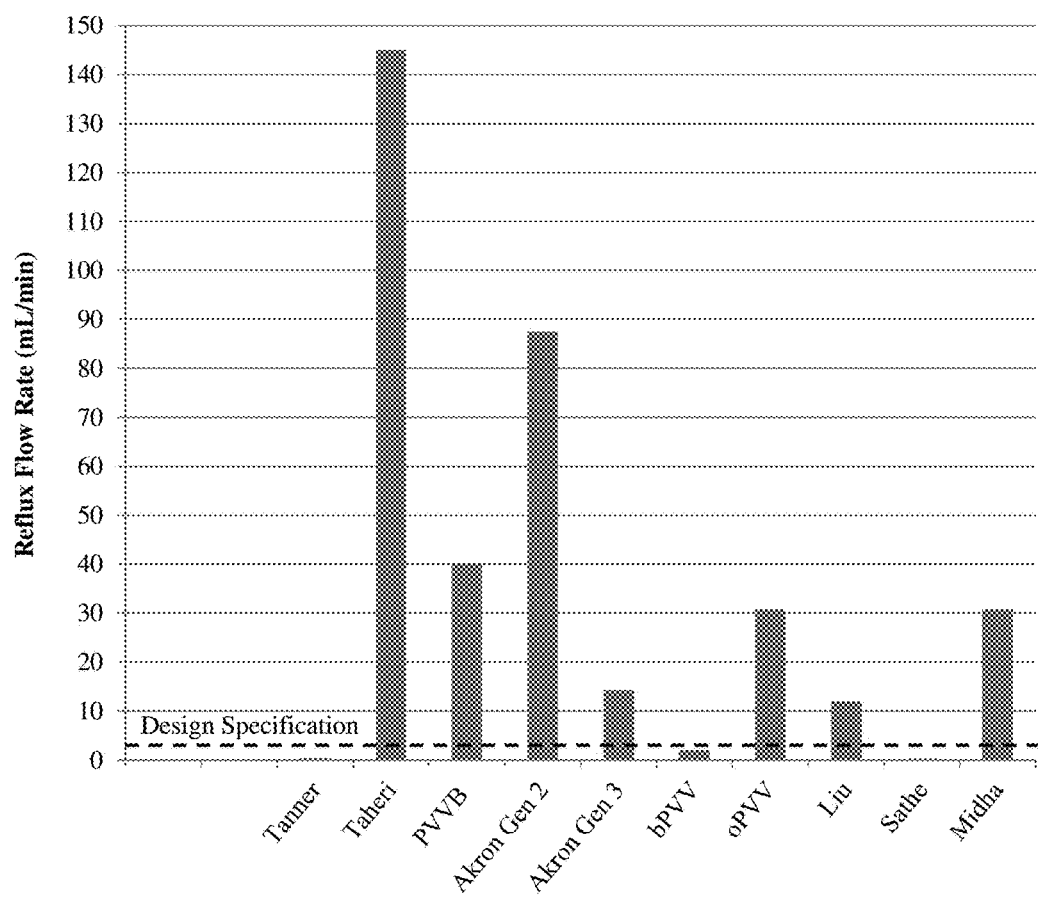
FIG. 24. Comparison of reflux flow rate of prosthetic venous valves which underwent experimental testing (data extracted from [34, 45, 46, 55, 58-61, 63]). The valve of the invention is also referred to as "Tanner" valve.

While many prosthetic venous valves have been developed, only a handful has reported experimental testing results. While the experimental methods for testing these valves have differed, an attempt has been made to briefly compare their performances (see Table 15) [36, 49, 57, 59, 61, 63, 64, 66]. Only three valves, the Sathe valve, Moriyama valve, and the valve of the invention, have demonstrated their ability to reduce reflux below 3 mL/min (see FIG. 24); however, only the prosthetic valve of the invention did not increase the outflow resistance to venous obstruction levels [63-64]. While the maximum shear rate during forward flow has not been calculated for most valves, shear induced platelet aggregation is a common failure mode for many previously developed prosthetic venous valves due to their relatively small orifices or sharp changes in geometry.

As the prosthetic venous valve of the invention is the only valve to meet every design specification for an effective prosthetic venous valve, this valve shows the most potential to be a minimally invasive treatment for deep venous reflux.

TABLE 15

Performance comparison of prosthetic venous valves which underwent experimental testing (data extracted from [36, 48-49, 57, 59, 61, 63-64, 66]). The valve of the invention is referred to as "Tanner" valve.

| Metric | Specification | Tanner | Taheri | PVVB | Akron Gen 2 | Akron Gen 3 | bPVV | oPVV | Liu | Sathe | Midha |
|---|---|---|---|---|---|---|---|---|---|---|---|
| Reflux rate (mL/min) | ≤8 | 0.3-0.4 | 145 | 40-120 | 87.5 | 14.25 | 2.04 | 30.8 | 12.16 | <0.3 | 30.8 |
| Reflux rate after fatigue (mL/min) | ≤8 | <0.1 | — | — | — | — | — | — | — | <0.3 | 41.1 |
| Leaflet closing time (s) | <0.5 | 0.067 | — | 0.43-0.49 | 1.38** | — | — | — | — | — | — |
| Distal pressure rise 30 seconds after a simulated calf flexion (%) | ≤10 | 7 | — | — | — | — | ~10 | 100 | — | — | — |
| Increased outflow resistance by the valve (mmHg * min/L) | <5 | 2.3 | 333* | 322* | 1.37-2.33 | 1.15-4.66 | >372 | >46 | — | 324.6 | 7.3 |
| Fluid behind leaflets washes out under forward flow | Yes | Yes | — | — | — | — | Yes*** | No*** | — | — | Yes*** |
| Smallest diameter valve can be placed in without buckling (mm) | ≤8.5 | 6.5 | — | — | — | — | — | — | — | — | 10 |
| Maximum shear rate during forward flow ($s^{-1}$) | <3500 | 2300 | — | — | 7600 | — | — | — | — | >10E3 | 3000 |
| Time to occlusion when running heparinized (3.5 mL/L) porcine blood in a flow loop (Hours) | >3 | >3 | — | — | — | — | — | — | — | 0.3 | >3 |

*Resistance of the testing system not reported so the total resistance of the valve and the esting system are presented.
**Only the results for a 2:1 scale mockup of the prototype valve were reported
***Applied flow rate was higher than 400 mL/min Additional fatigue testing of the invention valve may be performed to determine if the valve fails from fatigue before 9 million cycles, the expected number of cycles the valve undergoes in its lifetime, at a frequency of 0.67 Hz [64].

After stents of the appropriate size are obtained the animal study can be performed. If animal testing indicates that the valve is successful in human testing, an IRB protocol to test the valve in humans should be prepared. After IRB approval, the human study could then be performed.

While a set of valves for the CFV, femoral, and popliteal veins was provided, a set of valves which can service the superficial and perforating veins could be developed which would allow the valve to treat multisystem reflux. Human testing using the valve to correct multisystem reflux could then be pursued. A stented valve also has the potential to treat outflow obstruction in addition to venous reflux in subjects.

While the shoulder of the invention valve provided a visual cue to align a stent inside the valve correctly during manufacturing, it did not act as a ledge to stop the stent from protruding into the leaflets. Another method to help align the stent during manufacturing could likely be found, and the shoulder should be removed. The removal of the shoulder would reduce the bulk of the valve and potentially allow the valve to fit into a smaller catheter size. However, the removal of the shoulder would likely change the smallest diameter in which the valve can remain competent and the verification test would need to be performed again.

REFERENCES

1. Nicolaides, A. N., *Investigation of Chronic Venous Insufficiency: A Consensus Statement*. Circulation, 2000. 102 (20): p. e126-e163.
2. Meissner, M. H., et al., *The hemodynamics and diagnosis of venous disease*. J Vasc Surg, 2007. 46 Suppl S: p. 4S-24S.
3. Sherwood, L., *Human physiology: from cells to systems* 2012: Brooks/Cole Publishing Company.
4. Vasquez, M. A., et al., *Revision of the venous clinical severity score: venous outcomes consensus statement: special communication of the American Venous Forum Ad Hoc Outcomes Working Group*. J Vasc Surg, 2010. 52(5): p. 1387-96.
5. Lee, A. J., et al., *Lifestyle factors and the risk of varicose veins: Edinburgh Vein Study*. Journal of clinical epidemiology, 2003. 56(2): p. 171.
6. Fowkes, F., et al., *Lifestyle risk factors for lower limb venous reflux in the general population: Edinburgh Vein Study*. International journal of epidemiology, 2001. 30(4): p. 846-852.
7. Laurikka, J. O., et al., *Risk indicators for varicose veins in forty-to sixty-year-olds in the Tampere varicose vein study*. World journal of surgery, 2002. 26(6): p. 648-651.
8. Chiesa, R., et al., *Demographic factors and their relationship with the presence of CVI signs in Italy: the 24-cities cohort study*. European journal of vascular and endovascular surgery: the official journal of the European Society for Vascular Surgery, 2005. 30(6): p. 674.
9. Beebe-Dimmer, J. L., et al., *The epidemiology of chronic venous insufficiency and varicose veins*. Ann Epidemiol, 2005. 15(3): p. 175-84.
10. Criqui, M. H., et al., *Chronic Venous Disease in an Ethnically Diverse Population The San Diego Population Study*. American journal of epidemiology, 2003. 158(5): p. 448-456.
11. Phillips, T., et al., *A study of the impact of leg ulcers on quality of life: financial, social, and psychologic implications*. Journal of the American Academy of Dermatology, 1994. 31(1): p. 49-53.
12. Taheri, S. A. and R. O. Schultz, *Experimental prosthetic vein valve long-term results*. Angiology, 1995. 46(4): p. 299-303.
13. Nicolaides, A. N., et al., *The relation of venous ulceration with ambulatory venous pressure measurements*. Journal of Vascular Surgery, 1993. 17(2): p. 414-419.
14. McCaughan, J. J., et al., *In vitro observations of greater saphenous vein valves during pulsatile and nonpulsatile flow and following lysis*. Journal of Vascular Surgery, 1984. 1(2): p. 356-361.
15. van Bemmelen, P. S., et al., *The mechanism of venous valve closure: its relationship to the velocity of reverse flow*. Archives of Surgery, 1990. 125(5): p. 617.
16. Lurie, F., et al., *Mechanism of venous valve closure and role of the valve in circulation: a new concept*. Journal of Vascular Surgery, 2003. 38(5): p. 955-961.
17. van Bemmelen, P. S., et al., *Quantitative segmental evaluation of venous valvular reflux with duplex ultrasound scanning*. Journal of Vascular Surgery, 1989. 10(4): p. 0425-0431.
18. Labropoulos, N., et al., *Definition of venous reflux in lower-extremity veins. Journal of Vascular Surgery*, 2003. 38(4): p. 793-798.
19. Neglen, P., et al., *Hemodynamic and clinical impact of ultrasound-derived venous reflux parameters*. J Vasc Surg, 2004. 40(2): p. 303-10.
20. Danielsson, G., et al., *Deep axial reflux, an important contributor to skin changes or ulcer in chronic venous disease*. Journal of Vascular Surgery, 2003. 38(6): p. 1336-1341.
21. Iafrati, M. D., et al., *Correlation of venous noninvasive tests with the Society for Vascular Surgery/International Society for Cardiovascular Surgery clinical classification of chronic venous insufficiency*. Journal of vascular surgery: official publication, the Society for Vascular Surgery, 1994. 19(6): p. 1001-1007.
22. Araki, C. T., et al., *The significance of calf muscle pump function in venous ulceration*. Journal of Vascular Surgery, 1994. 20(6): p. 872-879.
23. Fukuoka, M., T. Sugimoto, and Y. Okita, *Prospective evaluation of chronic venous insufficiency based on foot venous pressure measurements and air plethysmography findings*. Journal of Vascular Surgery, 2003. 38(4): p. 804-811.
24. Christopoulos, D., et al., *Air-plethysmography and the effect of elastic compression on venous hemodynamics of the leg*. Journal of Vascular Surgery, 1987. 5(1): p. 148-159.
25. Labropoulos, N., et al., *Venous hemodynamic abnormalities in patients with leg ulceration*. The American journal of surgery, 1995. 169(6): p. 572-574.
26. Tripathi, R., M. Abbas, and N. Durrani, *Five-Year Experience of Valvular Reconstructions for Nonhealing Leg Ulceration due to Deep Venous Reflux: Lessons Learned*. Perspectives in vascular surgery and endovascular therapy, 2002. 15(2): p. 87-100.
27. Neglen, P. and S. Raju, *Detection of outflow obstruction in chronic venous insufficiency*. Journal of Vascular Surgery, 1993. 17(3): p. 583-589.
28. Vasquez, M. A., et al., *The utility of the Venous Clinical Severity Score in 682 limbs treated by radiofrequency saphenous vein ablation*. J Vasc Surg, 2007. 45(5): p. 1008-1014; discussion 1015.
29. Cesarone, M. R., et al., *Improvement of signs and symptoms of chronic venous insufficiency and microangiopathy with Pycnogenol: a prospective, controlled study*. Phytomedicine, 2010. 17(11): p. 835-9.
30. Raju, S. and P. Neglén, *Chronic venous insufficiency and varicose veins*. New England Journal of Medicine, 2009. 360(22): p. 2319-2327.

31. Eberhardt, R. T. and J. D. Raffetto, *Chronic venous insufficiency*. Circulation, 2005. 111(18): p. 2398-2409.
32. Neglén, P. and S. Raju, *Balloon dilation and stenting of chronic iliac vein obstruction: technical aspects and early clinical outcome*. Journal Information, 2000. 7(2).
33. Ofenloch, J. C., et al., *Endoscopic Venous Valve Transplantation with a Valve-Stent Device*. Ann Vasc Surg, 1997. 11(1): p. 62-67.
34. Taheri, S., et al., *Indications and results of vein valve transplant*. The Journal of cardiovascular surgery, 1986. 27(2): p. 163.
35. Dotter, C. T. *Interventional radiology—review of an emerging field*. in *Seminars in roentgenology*. 1981.
36. Taheri, S. A., et al., *Experimental prosthetic vein valve*. The American journal of surgery, 1988. 156(2): p. 111-114.
37. Hill, R., et al., *Development of a prosthetic venous valve*. Journal of biomedical materials research, 1985. 19(7): p. 827-832.
38. Dalsing, M. C., et al., *An early experience with endovascular venous valve transplantation*. Journal of vascular surgery: official publication, the Society for Vascular Surgery [and] International Society for Cardiovascular Surgery, North American Chapter, 1996. 24(5): p. 903.
39. Gomez-Jorge, J., A. C. Venbrux, and C. Magee, *Percutaneous Deployment of a Valved Bovine Jugular Vein in the Swine Venous System: A Potential Treatment for Venous Insufficiency*. Journal of Vascular and Interventional Radiology, 2000. 11(7): p. 931-936.
40. Pavcnik, D., et al., *Percutaneous management of chronic deep venous reflux: review of experimental work and early clinical experience with bioprosthetic valve*. Vascular Medicine, 2008. 13(1): p. 75-84.
41. Pavcnik, D., et al., *Percutaneous bioprosthetic venous valve: a long-term study in sheep*. Journal of Vascular Surgery, 2002. 35(3): p. 598-602.
42. Pavcnik, D., et al., *Percutaneous prosthetic venous valves: current state and possible applications*. Techniques in Vascular and Interventional Radiology, 2003. 6(3): p. 137-142.
43. Pavcnik, D., et al., *Second-generation percutaneous bioprosthetic valve: a short-term study in sheep*. Journal of Vascular Surgery, 2004. 40(6): p. 1223-1227.
44. Pavcnik, D., et al., *Significance of spatial orientation of percutaneously placed bioprosthetic venous valves in an ovine model*. J Vasc Interv Radiol, 2005. 16(11): p. 1511-6.
45. Pavcnik, D., *Update on Venous Valve Replacement: Long-Term Clinical Results*. Vascular, 2006. 14(Suppl 1): p. S106.
46. Pavcnik, D., et al. *Percutaneous Therapy for Deep Vein Reflux*. in *Seminars in Interventional Radiology*. 2005. Thieme Medical Publishers.
47. Pavcnik, D., et al., *Percutaneous autologous venous valve transplantation: short-term feasibility study in an ovine model*. J Vasc Surg, 2007. 46(2): p. 338-45.
48. Lee, D., et al., *In vitro testing of venous valves*. ASAIO transactions/American Society for Artificial Internal Organs, 1991. 37(3): p. M266.
49. DeLaria, G. A., et al., *Hemodynamic evaluation of a bioprosthetic venous prosthesis*. Journal of Vascular Surgery, 1993. 18(4): p. 577-586.
50. Serino, F., *Preliminary clinical experiences with VenPro PVVB*. Updating course in vascular pathology of surgical interest. In deep venous surgery and new technologies. Pisa, Italy, 2002.
51. de Borst, G. J., et al., *A percutaneous approach to deep venous valve insufficiency with a new self-expanding venous frame valve*. Journal of Endovascular Therapy, 2003. 10(2): p. 341-349.
52. Gale, S. S., et al., *Percutaneous venous valve bioprosthesis: initial observations*. Vascular and endovascular surgery, 2004. 38(3): p. 221-224.
53. Kucher, T., et al., *Endovascular delivery of vein segments with valves versus direct anastomosis*. Journal Information, 2005. 12(3).
54. Teebken, O., et al., *Tissue-engineered bioprosthetic venous valve: a long-term study in sheep*. European journal of vascular and endovascular surgery, 2003. 25(4): p. 305-312.
55. Teebken, O. E., et al., *Preclinical development of tissue-engineered vein valves and venous substitutes using re-endothelialised human vein matrix*. Eur J Vasc Endovasc Surg, 2009. 37(1): p. 92-102.
56. Dijkstra, M. L., et al., *PS134. Endovenous Valve Transfer for Chronic Venous Hypertension*. Journal of Vascular Surgery, 2012. 55(6): p. 61S.
57. Liu, C., et al., *Fabrication of tissue engineered vein containing valve scaffolds*. Zhonghua yi xue za zhi, 2012. 92(15): p. 1054.
58. Uflacker, R. *Percutaneously introduced artificial venous valve: experimental use in pigs*. in *The 1993 Annual Meeting of the Western Angiographic & Interventional Society*. 1993.
59. Rittgers, S. E., M. T. Oberdier, and S. Pottala, *Physiologically-based testing system for the mechanical characterization of prosthetic vein valves*. Biomed Eng Online, 2007. 6: p. 29.
60. Raja, V., *Computational Fluid Dynamics Analysis of a Prototypic, Prosthetic Venous Valve*, 2007, University of Akron.
61. Anim, K., *Design, Development, Testing, and Evaluation of a Prosthetic Venous Valve*, 2010, University of Akron.
62. Sathe, R. D., *Design and development of a novel implantable prosthetic vein valve*. 2006.
63. Moriyama, M., et al., *Evaluation of prosthetic venous valves, fabricated by electrospinning, for percutaneous treatment of chronic venous insufficiency*. J Artif Organs, 2011. 14(4): p. 294-300.
64. Sathe, R. D. and D. N. Ku, *Flexible Prosthetic Vein Valve*. Journal of Medical Devices, 2007. 1(2): p. 105.
65. Farrell, L. L. A. C., *Prosthetic Vein Valve: Delivery and In Vitro Evaluation*. 2007.
66. Midha, P. A., *Long-term patency of a polymer vein valve*. 2009.
67. Vasdekis, S. N., G. H. Clarke, and A. N. Nicolaides, *Quantification of venous reflux by means of duplex scanning*. Journal of Vascular Surgery, 1989. 10(6): p. 0670-0677.
68. Höjensgard, I., *Static and Dynamic Pressures in Superficial and Deep Veins of the Lower Extremity in Man*. Acta physiologica Scandinavica, 1953. 27(1): p. 49-67.
69. Stick, C., U. Hiedl, and E. Witzleb, *Venous pressure in the saphenous vein near the ankle during changes in posture and exercise at different ambient temperatures*. European journal of applied physiology and occupational physiology, 1993. 66(5): p. 434-438.
70. Alimi, Y., P. Barthelemy, and C. Juhan, *Venous pump of the calf: a study of venous and muscular pressures*. Journal of Vascular Surgery, 1994. 20(5): p. 728-735.
71. Fronek, A., et al., *Common femoral vein dimensions and hemodynamics including Valsalva response as a function*

*of sex, age, and ethnicity in a population study*. J Vasc Surg, 2001. 33(5): p. 1050-6.
72. Dickson, B. C., *Venous thrombosis: on the history of Virchow's triad*. Univ Toronto Med J, 2004. 81(3): p. 166-171.
73. Victor, R. G. and D. R. Seals, *Reflex stimulation of sympathetic outflow during rhythmic exercise in humans*. American Journal of Physiology-Heart and Circulatory Physiology, 1989. 257(6): p. H2017-H2024.
74. Wilson, N. and D. Rutt, *Repair and replacement of deep vein valves in the treatment of venous insufficiency*. British journal of surgery, 1991. 78(4): p. 388-394.
75. Savage, B., E. Saldívar, and Z. M. Ruggeri, *Initiation of platelet adhesion by arrest onto fibrinogen or translocation on von Willebrand factor*. Cell, 1996. 84(2): p. 289-297.
76. Hellums, J. D., 1993 *Whitaker Lecture: biorheology in thrombosis research*. Annals of biomedical engineering, 1994. 22(5): p. 445-455.
77. Bark, D. L., A. N. Para, and D. N. Ku, *Correlation of thrombosis growth rate to pathological wall shear rate during platelet accumulation*. Biotechnology and Bioengineering, 2012.
78. Zydney, A. L. and C. K. Colton, *Augmented solute transport in the shear flow of a concentrated suspension*. PCH, PhysicoChem. Hydrodyn, 1988. 10: p. 77.
79. Markou, C., et al., *The role of high wall shear rate on thrombus formation in stenoses*. ASME-PUBLICATIONS-BED, 1993. 26: p. 555-555.
80. Badimon, L., et al., *Influence of arterial damage and wall shear rate on platelet deposition. Ex vivo study in a swine model*. Arterioscler Thromb Vasc Biol, 1986. 6(3): p. 312-320.
81. Barstad, R. M., et al., *A perfusion chamber developed to investigate thrombus formation and shear profiles in flowing native human blood at the apex of well-defined stenoses*. Arterioscler Thromb Vasc Biol, 1994. 14(12): p. 1984-1991.
82. Barstad, R., P. Kierulf, and K. Sakariassen, *Collagen induced thrombus formation at the apex of eccentric stenoses: a time course study with non-anticoagulated human blood*. Thrombosis and haemostasis, 1996. 75(4): p. 685-692.
83. Para, A., et al., *Rapid Platelet Accumulation Leading to Thrombotic Occlusion*. Annals of biomedical engineering, 2011. 39(7): p. 1961-1971.
84. Onuki, Y., et al., *A review of the biocompatibility of implantable devices: current challenges to overcome foreign body response*. J Diabetes Sci Technol, 2008. 2(6): p. 1003-1015.
85. Ku, D. N., *New soft tissue Implants using organic elastomers*. Biomedical Engineering Systems and Technologies, 2009: p. 85-95.
86. Marascalco, P. J., et al., *Development of standard tests to examine viscoelastic properties of blood of experimental animals for pediatric mechanical support device evaluation*. ASAIO J, 2006. 52(5): p. 567-74.
87. Windberger, U., et al., *Whole blood viscosity, plasma viscosity and erythrocyte aggregation in nine mammalian species: reference values and comparison of data*. Experimental Physiology, 2003. 88(3): p. 431-440.
88. Brookshier, K. K. and J. Tarbell, *Effect of hematocrit on wall shear rate in oscillatory flow: do the elastic properties of blood play a role?* Biorheology, 1991. 28(6): p. 569.
89. Para, A. N., *Preventing rapid platelet accumulation under very high shear stress*. 2012.
90. Rachel, E. S., et al., *Percutaneous endovascular abdominal aortic aneurysm repair*. Ann Vasc Surg, 2002. 16(1): p. 43-49.
91. Ku, D. N., L. G. Braddon, and D. M. Wootton, Poly (vinyl alcohol) cryogel, 1999, U.S. Pat. No. 5,981,826.
92. Ku, D. N., Poly (vinyl alcohol) hydrogel, 2001, U.S. Pat. No. 6,231,605.
93. Weaver, J. D., *Development of a polyvinyl alcohol cryogel covered stent*. 2010.
94. Miyake, H., et al., *New small-caliber antithrombotic vascular prosthesis: Experimental study*. Microsurgery, 1984. 5(3): p. 144-150.
95. Weaver, J. D. and D. N. Ku, *Biomaterial testing for covered stent membranes: Evaluating thrombosis and restenosis potential*. Journal of Biomedical Materials Research Part B: Applied Biomaterials, 2011. 100(1): p. 103-110.
96. Nuttelman, C. R., et al., *Attachment of fibronectin to poly (vinyl alcohol) hydrogels promotes NIH3T3 cell adhesion, proliferation, and migration*. Journal of biomedical materials research, 2001. 57(2): p. 217-223.
97. Weaver, J. D. and D. N. Ku, *Mechanical Evaluation of Polyvinyl Alcohol Cryogels for Covered Stents*. Journal of Medical Devices, 2010. 4(3): p. 031002.
98. Fromageau, J., et al., *Characterization of PVA cryogel for intravascular ultrasound elasticity imaging*. Ultrasonics, Ferroelectrics and Frequency Control, IEEE Transactions on, 2003. 50(10): p. 1318-1324.
99. Fromageau, J., et al., *Estimation of polyvinyl alcohol cryogel mechanical properties with four ultrasound elastography methods and comparison with gold standard testings*. Ultrasonics, Ferroelectrics and Frequency Control, IEEE Transactions on, 2007. 54(3): p. 498-509.
100. Duboeuf, F., et al. *Static mechanical assessment of elastic Young's modulus of tissue mimicking materials used for medical imaging*. in *Engineering in Medicine and Biology Society, 2007. EMBS 2007. 29th Annual International Conference of the IEEE*. 2007. IEEE.
101. Stammen, J. A., et al., *Mechanical properties of a novel PVA hydrogel in shear and unconfined compression*. Biomaterials, 2001. 22(8): p. 799-806.
102. Williams, S., *Mechanical testing of a new biomaterial for potential use as a vascular graft and articular cartilage replacement*. MSthesis, Georgia Institute of Technology, 1998. 10.
103. Duboeuf, F. o., et al., *Investigation of PVA cryogel Young's modulus stability with time, controlled by a simple reliable technique*. Medical Physics, 2009. 36(2): p. 656.
104. Xie, L., et al., *Controlled mechanical and swelling properties of poly(vinyl alcohol)/sodium alginate blend hydrogels prepared by freeze-thaw followed by Ca2+ crosslinking*. Journal of Applied Polymer Science, 2012. 124(1): p. 823-831.
105. Holloway, J. L., A. M. Lowman, and G. R. Palmese, *Aging behavior of PVA hydrogels for soft tissue applications after in vitro swelling using osmotic pressure solutions*. Acta Biomater, 2012.
106. Cournane, S., et al., *Assessment of the accuracy of an ultrasound elastography liver scanning system using a PVA-cryogel phantom with optimal acoustic and mechanical properties*. Physics in medicine and biology, 2010. 55(19): p. 5965.
107. Gupta, S., S. Goswami, and A. Sinha, *A combined effect of freeze-thaw cycles and polymer concentration on the structure and mechanical properties of transparent PVA gels*. Biomed Mater, 2012. 7(1): p. 015006.

108. Depp, M. M. R., *PVA cryogel optimization and diffusion studies*. 1998.
109. Sollier, E., et al., *Rapid prototyping polymers for microfluidic devices and high pressure injections*. Lab on a Chip, 2011. 11(22): p. 3752-3765.
110. Dormandy, J., *Clinical significance of blood viscosity*. Annals of the Royal College of Surgeons of England, 1970. 47(4): p. 211.
111. Pedley, T. J. and X. Luo, *Fluid mechanics of large blood vessels*. 1995.
112. Berger, S. and L. Jou, *Flows in stenotic vessels*. Annual Review of Fluid Mechanics, 2003. 32(1): p. 347.
113. Cho, Y. and K. Kensey, *Effects of the non-Newtonian viscosity of blood on flows in a diseased arterial vessel. Part 1: Steady flows*. Biorheology, 1991. 28(3-4): p. 241.
114. Kundu, P. and I. Cohen, *Fluid Mechanics*. 2004, 2008, Elsevier Academic Press.
115. Johnston, B. M., et al., *Non-Newtonian blood flow in human right coronary arteries: steady state simulations*. J Biomech, 2004. 37(5): p. 709-20.
116. Lesser, A. J., *Fatigue Behavior of Polymers*. Encyclopedia Of Polymer Science and Technology, 2002.
117. Kinsel, D., *Design control requirements for medical device development*. World Journal for Pediatric and Congenital Heart Surgery, 2012. 3(1): p. 77-81.
118. Lu, W., et al., *The ovine jugular vein as a model for interventional radiology procedures*. Radiology and Oncology, 2008. 42(2): p. 59-65.
119. Lattimer, C. R., et al., *Saphenous pulsation on duplex may be a marker of severe chronic superficial venous insufficiency*. J Vasc Surg, 2012. 56(5): p. 1338-43.
120. Muhlberger, D., L. Morandini, and E. Brenner, *Venous valves and major superficial tributary veins near the saphenofemoral junction*. J Vasc Surg, 2009. 49(6): p. 1562-9.
121. Wilcoxon, F., *Individual comparisons by ranking methods*. Biometrics Bulletin, 1945. 1(6): p. 80-83.
122. Wilcoxon, F., et al., *Critical values and probability levels for the Wilcoxon rank sum test and the Wilcoxon signed rank test* 1963: Lederle Laboratories Division, American Cyanamid.
123. Faul, F., et al., *G* Power 3: A flexible statistical power analysis program for the social, behavioral, and biomedical sciences*. Behavior research methods, 2007. 39(2): p. 175-191.
124. Faul, F., et al., *Statistical power analyses using G* Power 3.1: Tests for correlation and regression analyses*. Behavior research methods, 2009. 41(4): p. 1149-1160.
125. Bia, D., et al., *In vitro model to study arterial wall dynamics through pressure-diameter relationship analysis*. Latin American applied research, 2005. 35(3): p. 217-224.
126. Beddy, P., et al., *Valsalva and gravitational variability of the internal jugular vein and common femoral vein: ultrasound assessment*. Eur J Radiol, 2006. 58(2): p. 307-9.
127. Rippey, J. C., O. Pascu, and I. Jacobs, *Abdominal compression effectively increases the size of the common femoral vein, as measured by ultrasonography*. Ann Emerg Med, 2008. 52(4): p. 446-52.
128. Hertzberg, B., et al., *Sonographic assessment of lower limb vein diameters: implications for the diagnosis and characterization of deep venous thrombosis*. American Journal of Roentgenology, 1997. 168(5): p. 1253-1257.
129. Haenen, J., et al., *Venous duplex scanning of the leg: range, variability and reproducibility*. Clinical Science, 1999. 96: p. 271-277.
130. Raju, S. and R. Fredericks, *Valve reconstruction procedures for nonobstructive venous insufficiency: Rationale, techniques, and results in 107 procedures with two-to eight-year follow-up*. Journal of Vascular Surgery, 1988. 7(2): p. 301-310.
131. Kistner, R. and M. Sparkuhl, *Surgery in acute and chronic venous disease*. Surgery, 1979. 85(1): p. 31.
132. Eriksson, I. and B. Almgren, *Surgical reconstruction of incompetent deep vein valves*. Upsala journal of medical sciences, 1988. 93(2): p. 139-143.
133. Nash, T., *Long term results of vein valve transplants placed in the popliteal vein for intractable post phlebitic venous ulcers and pre-ulcer skin changes*. J Cardiovasc Surg, 1988. 29(6): p. 712-6.
134. Sottiurai, V., *Comparison of surgical modalities in the treatment of recurrent venous ulcer*. International angiology: a journal of the International Union of Angiology, 1990. 9(4): p. 231.
135. Sottiurai, V. S., *Current surgical approaches to venous hypertension and valvular reflux*. International Journal of Angiology, 1996. 5(1): p. 49-54.
136. Delis, K. T., et al., *Lower limb venous haemodynamic impairment on dependency: quantification and implications for the "economy class" position*. THROMBOSIS AND HAEMOSTASIS-STUTTGART-, 2004. 91(5): p. 941-950.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:
1. A prosthetic venous valve comprising:
   a) a cylindrical base having a length greater than its diameter and a thin wall with a thickness less than about 2 mm,
   b) two opposed leaflets that are thinner than about 1 mm and longer than half the base diameter, wherein said leaflets extend downstream from the cylindrical base in an axial direction to an ellipsoidal opening with a luminal cross-sectional area less than a luminal cross-sectional area of the base, and
   c) a transition shoulder region thinner than about 3 mm in wall thickness that joins the base and the leaflets and circumscribe the cylindrical base;
   wherein said prosthetic venous valve is composed of a biocompatible polymer;
   wherein each valve leaflet has two major axes in the axial direction that pass through points that are maximally spaced apart on the ellipsoidal opening and two minor axes in the axial direction that pass through points that are minimally spaced apart on the ellipsoidal opening;
   wherein each valve leaflet tapers uniformly along a minor axis from a thick region at the transition that joins the base and the leaflets to the leaflet tip and has a uniform thickness along a major axis from the transition that joins the base and the leaflets to the leaflet tip;
   wherein said prosthetic venous valve has a backflow reflux under 160 mmHg and a forward flow resistance less than 20 mmHg*min/L; and
   wherein shear rates at the base wall are restricted to between 1 $S^{-1}$ and 100,000 $S^{-1}$.

2. The prosthetic venous valve of claim 1, wherein said biocompatible polymer is hydrophilic.

3. The prosthetic venous valve of claim 1, wherein hydrophilic biocompatible polymer is poly(vinyl-alcohol) (PVA) cryogel or PVA hydrogel.

4. The prosthetic venous valve of claim 1, wherein said biocompatible polymer is polyurethane or polyester.

5. The prosthetic venous valve of claim 1, wherein said base comprises a hydrogel polymer.

6. The prosthetic venous valve of claim 5, wherein said base further comprises metal parts covered partially or all by the polymer.

7. The prosthetic venous valve of claim 1, wherein said leaflets have opposed tips along the minor axis which are spaced-apart by a distance less than the base internal diameter.

8. The prosthetic venous valve of claim 7, wherein a minimum distance between the tips of the leaflets in a deployed configuration is less than the internal diameter of the base.

9. The prosthetic venous valve of claim 1, wherein said leaflets further comprise one or more slits in the tips between the leaflets along the major axis.

10. The prosthetic venous valve of claim 9, wherein said slit is about 0.1 mm wide and greater than about 1 mm long.

11. The prosthetic venous valve of claim 1, wherein said prosthetic venous valve fits into a hollow catheter with inside diameter at least 1 mm smaller than the outside diameter of the base.

12. The prosthetic venous valve of claim 11, wherein said prosthetic venous valve fits into a 16 Fr. catheter for delivery.

13. The prosthetic venous valve of claim 11, wherein said prosthetic venous valve collapses into a catheter tube less than 1 mm of outside diameter of the base and is able to re-expand after deployment.

* * * * *